US011137400B2

(12) United States Patent
Ouyang

(10) Patent No.: US 11,137,400 B2
(45) Date of Patent: Oct. 5, 2021

(54) METHODS FOR PREDICTING AND DETERMINING RESPONSIVENESS TO ACTIVATORS OF JNK KINASE

(71) Applicant: UNIVERSITY OF PITTSBURGH-OF THE COMMONWEALTH SYSTEM OF HIGHER EDUCATION, Pittsburgh, PA (US)

(72) Inventor: Hongjiao Ouyang, Plano, TX (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 93 days.

(21) Appl. No.: 16/626,488

(22) PCT Filed: Jun. 29, 2018

(86) PCT No.: PCT/US2018/040227
§ 371 (c)(1),
(2) Date: Dec. 24, 2019

(87) PCT Pub. No.: WO2019/006261
PCT Pub. Date: Jan. 3, 2019

(65) Prior Publication Data
US 2020/0116723 A1    Apr. 16, 2020

Related U.S. Application Data

(60) Provisional application No. 62/527,296, filed on Jun. 30, 2017.

(51) Int. Cl.
| | |
|---|---|
| *A61K 31/69* | (2006.01) |
| *A61K 31/56* | (2006.01) |
| *A61K 31/445* | (2006.01) |
| *A61P 35/00* | (2006.01) |
| *G01N 33/574* | (2006.01) |
| *A61K 31/454* | (2006.01) |
| *A61K 31/4965* | (2006.01) |
| *A61K 31/573* | (2006.01) |
| *A61K 45/06* | (2006.01) |
| *G01N 33/50* | (2006.01) |

(52) U.S. Cl.
CPC ..... *G01N 33/57407* (2013.01); *A61K 31/454* (2013.01); *A61K 31/4965* (2013.01); *A61K 31/573* (2013.01); *A61K 45/06* (2013.01); *A61P 35/00* (2018.01); *G01N 33/5011* (2013.01); *G01N 2440/14* (2013.01)

(58) Field of Classification Search
CPC ...... A61K 31/69; A61K 31/56; A61K 31/445; A61P 35/00
USPC .......................... 514/64, 178, 323
See application file for complete search history.

(56) References Cited

U.S. PATENT DOCUMENTS

| | | |
|---|---|---|
| 2009/0232738 A1 | 9/2009 | Glimcher et al. |
| 2014/0011748 A1 | 1/2014 | Chin et al. |

OTHER PUBLICATIONS

Adolph TE, Tomczak MF, Niederreiter L, Ko HJ, Bock J, Martinez-Naves E, Glickman JN, Tschurtschenthaler M, Hartwig J, Hosomi S, et al. Paneth cells as a site of origin for intestinal inflammation. Nature. 2013;503(7475):272-6.
Altschul, S. F., Gish, W., Miller, W., Myers, E. W., & Lipman, D. J. (1990). Basic local alignment search tool. Journal of molecular biology, 215(3), 403-410.
Altschul, S.F., Madden, T.L., Schäffer, A.A., Zhang, J., Zhang, Z., Miller, W. and Lipman, D.J., 1997. Gapped BLAST and PSI-BLAST: a new generation of protein database search programs. Nucleic acids research, 25(17), pp. 3389-3402.
Anderson, K. C. (Oct. 2005). Lenalidomide and thalidomide: mechanisms of action—similarities and differences. In Seminars in Hematology (vol. 42, pp. S3-S8). WB Saunders.
Ardley HC, and Robinson PA. E3 ubiquitin ligases. Essays Biochem. 2005;41, 15-30.
Auf, G., Jabouille, A., Guérit, S., Pineau, R., Delugin, M., Bouchecareilh, M., . . . & von Deimling, A. (2010). Inositol-requiring enzyme 1α is a key regulator of angiogenesis and invasion in malignant glioma. Proceedings of the National Academy of Sciences, 107(35), 15553-15558.
Bae, Jooeun, et al. Identification of novel myeloma-specific XBP1 peptides able to generate cytotoxic T lymphocytes: a potential therapeutic application in multiple myeloma. Leukemia 25.10 (2011): 1610-1619.
Bagratuni T, Wu P, Gonzalez de Castro D, Davenport EL, Dickens NJ, Walker BA, Boyd K, Johnson DC, Gregory W, Morgan GJ, et al. XBP1s levels are implicated in the biology and outcome of myeloma mediating different clinical outcomes to thalidomide-based treatments. Blood. 2010;116(2):250-3.
Bai QX, and Zhang XY. Curcumin enhances cytotoxic effects of bortezomib in human multiple myeloma H929 cells: potential roles of NF-kappaB/JNK. Int J Mol Sci. 2012;13(4):4831-8.
Bataille R, Chappard D, Marcelli C, Dessauw P, Baldet P, Sany J, and Alexandre C. Recruitment of new osteoblasts and osteoclasts is the earliest critical event in the pathogenesis of human multiple myeloma. J Clin Invest. 1991;88(1):62-6.

(Continued)

*Primary Examiner* — Raymond J Henley, III
(74) *Attorney, Agent, or Firm* — Meunier Carlin & Curfman LLC

(57) ABSTRACT

The present disclosure relates to methods for predicting and/or determining responsiveness to an activator of JNK kinase activity. The present disclosure further relates to improved methods for treating a cancer patient with an activator of JNK kinase activity. The present disclosure also relates to methods for screening for a modulator of XBP1s protein phosphorylation.

19 Claims, 49 Drawing Sheets
Specification includes a Sequence Listing.

(56) References Cited

OTHER PUBLICATIONS

Beaino W, Nedrow JR, and Anderson CJ. Evaluation of (68)Ga- and (177)Lu-DOTA-PEG4-LLP2A for VLA-4-Targeted PET Imaging and Treatment of Metastatic Melanoma. Mol Pharm. 2015;12(6):1929-38.

Bogoyevitch MA, and Kobe B. Uses for JNK: the many and varied substrates of the c-Jun N-terminal kinases. Microbiol Mol Biol Rev. 2006;70(4):1061-95.

Byrd AE, and Brewer JW. Intricately Regulated: A Cellular Toolbox for Fine-Tuning XBP1 Expression and Activity. Cells. 2012;1(4):738-53.

Calfon M, Zeng H, Urano F, Till JH, Hubbard SR, Harding HP, Clark SG, and Ron D. IRE1 couples endoplasmic reticulum load to secretory capacity by processing the XBP-1 mRNA. Nature. 2002;415(6867):92-6.

Cardozo T, and Pagano M. The SCF ubiquitin ligase: insights into a molecular machine. Nat Rev Mol Cell Biol. 2004;5(9):739-51.

Carrasco DR, Sukhdeo K, Protopopova M, Sinha R, Enos M, Carrasco DE, Zheng M, Mani M, Henderson J, Pinkus GS, et al. The differentiation and stress response factor XBP-1 drives multiple myeloma pathogenesis. Cancer Cell. 2007;11(4):349-60.

Cellurale C, Girnius N, Jiang F, Cavanagh-Kyros J, Lu S, Garlick DS, Mercurio AM, and Davis RJ. Role of JNK in mammary gland development and breast cancer. Cancer Res. 2012;72(2):472-81.

Chan JY, Luzuriaga J, Maxwell EL, West PK, Bensellam M, and Laybutt DR. The balance between adaptive and apoptotic unfolded protein responses regulates beta-cell death under ER stress conditions through XBP1, CHOP and JNK. Mol Cell Endocrinol. 2015;413, 189-201.

Chauhan D, Pandey P, Ogata A, Teoh G, Treon S, Urashima M, Kharbanda S, and Anderson KC. Dexamethasone induces apoptosis of multiple myeloma cells in a JNK/SAP kinase independent mechanism. Oncogene. 1997;15(7):837-43.

Chen H, and Qi L. SUMO modification regulates the transcriptional activity of XBP1. Biochem J. 2010;429(1):95-102.

Chen X, Iliopoulos D, Zhang Q, Tang Q, Greenblatt MB, Hatziapostolou M, Lim E, Tam WL, Ni M, Chen Y, et al. XBP1 promotes triple-negative breast cancer by controlling the HIF1 alpha pathway. Nature. 2014;508(7494):103-7.

Coulthard LR, White DE, Jones DL, McDermott MF, and Burchill SA. p38(MAPK): stress responses from molecular mechanisms to therapeutics. Trends Mol Med. 2009;15(8):369-79.

Cubillos-Ruiz, J. R., Silberman, P. C., Rutkowski, M. R., Chopra, S., Perales-Puchalt, A., Song, M., . . . & Ellenson, L. H. (2015). ER stress sensor XBP1 controls anti-tumor immunity by disrupting dendritic cell homeostasis. Cell, 161(7), 1527-1538.

Curran MP, and McKeage K. Bortezomib: a review of its use in patients with multiple myeloma. Drugs. 2009;69(7):859-88.

Davies MP, Barraclough DL, Stewart C, Joyce KA, Eccles RM, Barraclough R, Rudland PS, and Sibson DR. Expression and splicing of the unfolded protein response gene XBP-1 are significantly associated with clinical outcome of endocrine-treated breast cancer. Int J Cancer. 2008;123(1):85-8.

Fang Q, Inanc B, Schamus S, Wang XH, Wei L, Brown AR, Svilar D, Sugrue KF, Goellner EM, Zeng X, et al. HSP90 regulates DNA repair via the interaction between XRCC1 and DNA polymerase beta. Nat Commun. 2014;5, 5513.

Feuerbach D, and Feyen JH. Expression of the cell-adhesion molecule VCAM-1 by stromal cells is necessary for osteoclastogenesis. FEBS Lett. 1997;402(1):21-4.

Fuchs SY, Spiegelman VS, and Kumar KG. The many faces of beta-TrCP E3 ubiquitin ligases: reflections in the magic mirror of cancer. Oncogene. 2004;23(11):2028-36.

Fujimoto T, Onda M, Nagai H, Nagahata T, Ogawa K, and Emi M. Upregulation and overexpression of human X-box binding protein 1 (hXBP-1) gene in primary breast cancers. Breast Cancer. 2003;10(4):301-6.

Garrett IR, Dallas S, Radl J, and Mundy GR. A murine model of human myeloma bone disease. Bone. 1997;20(6):515-20.

Geitz, H., Handt, S., & Zwingenberger, K. (1996). Thalidomide selectively modulates the density of cell surface molecules involved in the adhesion cascade. Immunopharmacology, 31(2-3), 213-221.

Goranov SE, and Goranova-Marinova VS. Bortezomib (Velcade)—a new therapeutic strategy for patients with refractory multiple myeloma. Folia Med (Plovdiv). 2005;47(3-4):11-9. Abstract.

Gupta A, Hossain MM, Miller N, Kerin M, Callagy G, and Gupta S. NCOA3 coactivator is a transcriptional target of XBP1 and regulates PERK-eIF2alpha-ATF4 signalling in breast cancer. Oncogene. 2016;35(45):5860-71.

Gupta S, Barrett T, Whitmarsh AJ, Cavanagh J, Sluss HK, Derijard B, and Davis RJ. Selective interaction of JNK protein kinase isoforms with transcription factors. EMBO J. 1996;15(11):2760-70.

Gupta, D., Treon, S. P., Shima, Y., Hideshima, T., Podar, K., Tai, Y. T., . . . & Schlossman, R. L. (2001). Adherence of multiple myeloma cells to bone marrow stromal cells upregulates vascular endothelial growth factor secretion: therapeutic applications. Leukemia, 15(12), 1950-1961.

Hassler JR, Scheuner DL, Wang S, Han J, Kodali VK, Li P, Nguyen J, George JS, Davis C, Wu SP, et al. The IRE1alpha/XBP1s Pathway Is Essential for the Glucose Response and Protection of beta Cells. PLoS Biol. 2015;13(10):e1002277.

Hazzalin CA, Le Panse R, Cano E, and Mahadevan LC. Anisomycin selectively desensitizes signalling components involved in stress kinase activation and fos and jun induction. Mol Cell Biol. 1998;18(4):1844-54.

He Y, Sun S, Sha H, Liu Z, Yang L, Xue Z, Chen H, and Qi L. Emerging roles for XBP1, a sUPeR transcription factor. Gene Expr. 2010;15(1):13-25.

Henikoff, S., & Henikoff, J. G. (1992). Amino acid substitution matrices from protein blocks. Proceedings of the National Academy of Sciences, 89(22), 10915-10919.

Hetz C, and Glimcher LH. Fine-tuning of the unfolded protein response: Assembling the IRE1alpha interactome. Mol Cell. 2009;35(5):551-61.

Hideshima T, Catley L, Yasui H, Ishitsuka K, Raje N, Mitsiades C, Podar K, Munshi NC, Chauhan D, Richardson PG, et al. Perifosine, an oral bioactive novel alkylphospholipid, inhibits Akt and induces in vitro and in vivo cytotoxicity in human multiple myeloma cells. Blood. 2006;107(10):4053-62.

Hideshima T, Chauhan D, Hayashi T, Podar K, Akiyama M, Mitsiades C, N MI, Gong B, Bonham L, de Vries P, et al. Antitumor activity of lysophosphatidic acid acyltransferase-beta inhibitors, a novel class of agents, in multiple myeloma. Cancer Res. 2003;63(23):8428-36.

Hideshima T, Mitsiades C, Akiyama M, Hayashi T, Chauhan D, Richardson P, Schlossman R, Podar K, Munshi NC, Mitsiades N, et al. Molecular mechanisms mediating antimyeloma activity of proteasome inhibitor PS-341. Blood. 2003;101(4):1530-4.

Hideshima T, Mitsiades C, Tonon G, Richardson PG, and Anderson KC. Understanding multiple myeloma pathogenesis in the bone marrow to identify new therapeutic targets. Nat Rev Cancer. 2007;7(8):585-98.

Hideshima T, Richardson P, Chauhan D, Palombella VJ, Elliott PJ, Adams J, and Anderson KC. The proteasome inhibitor PS-341 inhibits growth, induces apoptosis, and overcomes drug resistance in human multiple myeloma cells. Cancer Res. 2001;61(7):3071-6.

Hirosumi J, Tuncman G, Chang L, Gorgun CZ, Uysal KT, Maeda K, Karin M, and Hotamisligil GS. A central role for JNK in obesity and insulin resistance. Nature. 2002;420(6913):333-6.

Hu R, Warri A, Jin L, Zwart A, Riggins RB, Fang HB, and Clarke R. NF-kappaB signaling is required for XBP1 (unspliced and spliced)-mediated effects on antiestrogen responsiveness and cell fate decisions in breast cancer. Mol Cell Biol. 2015;35(2):379-90.

Inuzuka H, Tseng A, Gao D, Zhai B, Zhang Q, Shaik S, Wan L, Ang XL, Mock C, Yin H, et al. Phosphorylation by casein kinase I promotes the turnover of the Mdm2 oncoprotein via the SCF(beta-TRCP) ubiquitin ligase. Cancer Cell. 2010;18(2):147-59.

Iwakoshi, Neal N., et al. Plasma cell differentiation and the unfolded protein response intersect at the transcription factor XBP-1. Nature immunology 4.4 (2003): 321-329.

(56) References Cited

OTHER PUBLICATIONS

Jin J, Shirogane T, Xu L, Nalepa G, Qin J, Elledge SJ, and Harper JW. SCFbeta-TRCP links Chk1 signaling to degradation of the Cdc25A protein phosphatase. Genes Dev. 2003;17(24):3062-74.
Johnson GL, and Nakamura K. The c-jun kinase/stress-activated pathway: regulation, function and role in human disease. Biochim Biophys Acta. 2007;1773(8):1341-8.
Kaneto H. The JNK pathway as a therapeutic target for diabetes. Expert Opin Ther Targets. 2005;9(3):581-92.
Karlin, S., & Altschul, S. F. (1993). Applications and statistics for multiple high-scoring segments in molecular sequences. Proceedings of the National Academy of Sciences, 90(12), 5873-5877.
Kaser A, Lee AH, Franke A, Glickman JN, Zeissig S, Tilg H, Nieuwenhuis EE, Higgins DE, Schreiber S, Glimcher LH, et al. XBP1 links ER stress to intestinal inflammation and confers genetic risk for human inflammatory bowel disease. Cell. 2008;134(5):743-56.
Lee AH, Heidtman K, Hotamisligil GS, and Glimcher LH. Dual and opposing roles of the unfolded protein response regulated by IRE1alpha and XBP1 in proinsulin processing and insulin secretion. Proc Natl Acad Sci U S A. 2011;108(21):8885-90.
Lee J, Sun C, Zhou Y, Lee J, Gokalp D, Herrema H, Park SW, Davis RJ, and Ozcan U. p38 MAPK-mediated regulation of Xbp1s is crucial for glucose homeostasis. Nat Med. 2011;17(10):1251-60.
Lei K, Nimnual A, Zong WX, Kennedy NJ, Flavell RA, Thompson CB, Bar-Sagi D, and Davis RJ. The Bax subfamily of Bcl2-related proteins is essential for apoptotic signal transduction by c-Jun NH(2)-terminal kinase. Mol Cell Biol. 2002;22(13):4929-42.
Leiba M, Jakubikova J, Klippel S, Mitsiades CS, Hideshima T, Tai YT, Leiba A, Pines M, Richardson PG, Nagler A, et al. Halofuginone inhibits multiple myeloma growth in vitro and in vivo and enhances cytotoxicity of conventional and novel agents. Br J Haematol. 2012;157(6):718-31.
Leung-Hagesteijn et al., Xbp1s-Negative Tumor B Cells and Pre-Plasmablasts Mediate Therapeutic Proteasome Inhibitor Resistance in Multiple Myeloma. Cancer Cell, 24:289-304 (2013).
Lin JH, Li H, Yasumura D, Cohen HR, Zhang C, Panning B, Shokat KM, Lavail MM, and Walter P. IRE1 signaling affects cell fate during the unfolded protein response. Science. 2007;318(5852):944-9.
Liu J, Ibi D, Taniguchi K, Lee J, Herrema H, Akosman B, Mucka P, Salazar Hernandez MA, Uyar MF, Park SW, et al. Inflammation Improves Glucose Homeostasis through IKKbeta-XBP1s Interaction. Cell. 2016;167(4):1052-66 e18.
Michigami T, Shimizu N, Williams PJ, Niewolna M, Dallas SL, Mundy GR, and Yoneda T. Cell-cell contact between marrow stromal cells and myeloma cells via VCAM-1 and alpha(4)beta(1)-integrin enhances production of osteoclast-stimulating activity. Blood. 2000;96(5):1953-60.
Miedel MT, Zeng X, Yates NA, Silverman GA, and Luke CJ. Isolation of serpin-interacting proteins in C. elegans using protein affinity purification. Methods. 2014;68(3):536-41.
Mimura, Naoya, et al. Blockade of XBP1 splicing by inhibition of IRE1α is a promising therapeutic option in multiple myeloma. Blood, The Journal of the American Society of Hematology 119.24 (2012): 5772-5781.
Ming J, Ruan S, Wang M, Ye D, Fan N, Meng Q, Tian B, and Huang T. A novel chemical, STF-083010, reverses tamoxifen-related drug resistance in breast cancer by inhibiting IRE1/XBP1. Oncotarget. 2015;6(38):40692-703.
Mitsiades CS, Mitsiades N, Munshi NC, and Anderson KC. Focus on multiple myeloma. Cancer Cell. 2004;6(5):439-44.
Miyake K, Hasunuma Y, Yagita H, and Kimoto M. Requirement for VLA-4 and VLA-5 integrins in lymphoma cells binding to and migration beneath stromal cells in culture. J Cell Biol. 1992;119(3):653-62.
Nakamura M, Gotoh T, Okuno Y, Tatetsu H, Sonoki T, Uneda S, Mori M, Mitsuya H, and Hata H. Activation of the endoplasmic reticulum stress pathway is associated with survival of myeloma cells. Leuk Lymphoma. 2006;47(3):531-9.

Oslowski et al., Measuring ER stress and the unfolded protein response using mammalian tissue culture system. Methods Enzymol., 490:71-92 (2011).
Papandreou I, Denko NC, Olson M, Van Melckebeke H, Lust S, Tam A, Solow-Cordero DE, Bouley DM, Offner F, Niwa M, et al. Identification of an Ire1alpha endonuclease specific inhibitor with cytotoxic activity against human multiple myeloma. Blood. 2011;117(4):1311-4.
Pei XY, Dai Y, and Grant S. The proteasome inhibitor bortezomib promotes mitochondrial injury and apoptosis induced by the small molecule Bcl-2 inhibitor HA14-1 in multiple myeloma cells. Leukemia. 2003;17(10):2036-45.
Piperi C, Adamopoulos C, and Papavassiliou AG. XBP1: A Pivotal Transcriptional Regulator of Glucose and Lipid Metabolism. Trends Endocrinol Metab. 2016;27(3):119-22.
Podar K, Chauhan D, and Anderson KC. Bone marrow microenvironment and the identification of new targets for myeloma therapy. Leukemia. 2009;23(1):10-24.
Rajkumar et al., Multiple Myeloma: Diagnosis and Treatment S. Mayo Clin. Proc., 91:101-119 (2016).
Reimold, Andreas M., et al. Plasma cell differentiation requires the transcription factor XBP-1. Nature 412.6844 (2001): 300-307.
Ri, Masaki, et al. Identification of Toyocamycin, an agent cytotoxic for multiple myeloma cells, as a potent inhibitor of ER stress-induced XBP1 mRNA splicing. Blood cancer journal 2.7 (2012): e79-e79.
Roccaro AM, Hideshima T, Richardson PG, Russo D, Ribatti D, Vacca A, Dammacco F, and Anderson KC. Bortezomib as an antitumor agent. Curr Pharm Biotechnol. 2006;7(6):441-8. Abstract.
Roodman GD. Pathogenesis of myeloma bone disease. Blood Cells Mol Dis. 2004;32(2):290-2.
Roodman GD. Role of the bone marrow microenvironment in multiple myeloma. J Bone Miner Res. 2002;17(11):1921-5.
Rosen HN, Moses AC, Garber J, Iloputaife ID, Ross DS, Lee SL, and Greenspan SL. Serum CTX: a new marker of bone resorption that shows treatment effect more often than other markers because of low coefficient of variability and large changes with bisphosphonate therapy. Calcif Tissue Int. 2000;66(2):100-3.
Roy PK, Rashid F, Bragg J, and Ibdah JA. Role of the JNK signal transduction pathway in inflammatory bowel disease. World J Gastroenterol. 2008;14(2):200-2.
Saha MN, Jiang H, Yang Y, Zhu X, Wang X, Schimmer AD, Qiu L, and Chang H. Targeting p53 via JNK pathway: a novel role of RITA for apoptotic signaling in multiple myeloma. PLoS One. 2012;7(1):e30215.
Sampaio, E. P., Sarno, E. N., Galilly, R., Cohn, Z. A., & Kaplan, G. (1991). Thalidomide selectively inhibits tumor necrosis factor alpha production by stimulated human monocytes. The Journal of experimental medicine, 173(3), 699-703.
Shaffer, A. L., et al. XBP1, downstream of Blimp-1, expands the secretory apparatus and other organelles, and increases protein synthesis in plasma cell differentiation. Immunity 21.1 (2004): 81-93.
Shao M, Shan B, Liu Y, Deng Y, Yan C, Wu Y, Mao T, Qiu Y, Zhou Y, Jiang S, et al. Hepatic IRE1alpha regulates fasting-induced metabolic adaptive programs through the XBP1s-PPARalpha axis signalling. Nat Commun. 2014;5, 3528.
Sharkey, Janelle, Tiffany Khong, and Andrew Spencer. PKC412 demonstrates JNK-dependent activity against human multiple myeloma cells. Blood 109.4 (2007): 1712-1719.
Shen et al., Coagulation profiles and thromboembolic events of bortezomib plus thalidomide and dexamethasone therapy in newly diagnosed multiple myelomaLeuk. Res., 35:147-151 (2011).
Shevchenko A, Tomas H, Havlis J, Olsen JV, and Mann M. In-gel digestion for mass spectrometric characterization of proteins and proteomes. Nat Protoc. 2006;1(6):2856-60.
Singh AV, Bandi M, Raje N, Richardson P, Palladino MA, Chauhan D, and Anderson KC. A novel vascular disrupting agent plinabulin triggers JNK-mediated apoptosis and inhibits angiogenesis in multiple myeloma cells. Blood. 2011;117(21):5692-700.
Soodgupta et al., Very Late Antigen-4 (a4b1 Integrin) Targeted PET Imaging of Multiple Myeloma. PLoS One, 8:e55841 (2013).

(56) References Cited

OTHER PUBLICATIONS

Soodgupta, Deepti, et al. Ex vivo and in vivo evaluation of overexpressed VLA-4 in multiple myeloma using LLP2A imaging agents. Journal of Nuclear Medicine 57.4 (2016): 640-645.

Tang, C. H. A., Ranatunga, S., Kriss, C. L., Cubitt, C. L., Tao, J., Pinilla-Ibarz, J. A., . . . & Hu, C. C. A. (2014). Inhibition of ER stress-associated IRE-1/XBP-1 pathway reduces leukemic cell survival. The Journal of clinical investigation, 124(6), 2585-2598.

Terpos E, Szydlo R, Apperley JF, Hatjiharissi E, Politou M, Meletis J, Viniou N, Yataganas X, Goldman JM, and Rahemtulla A. Soluble receptor activator of nuclear factor kappaB ligand-osteoprotegerin ratio predicts survival in multiple myeloma: proposal for a novel prognostic index. Blood. 2003;102(3):1064-9.

Uemura A, Taniguchi M, Matsuo Y, Oku M, Wakabayashi S, and Yoshida H. UBC9 regulates the stability of XBP1, a key transcription factor controlling the ER stress response. Cell Struct Funct. 2013;38(1):67-79.

Urano F, Wang X, Bertolotti A, Zhang Y, Chung P, Harding HP, and Ron D. Coupling of stress in the ER to activation of JNK protein kinases by transmembrane protein kinase IRE1 Science. 2000;287(5453):664-6.

Usmani, Saad Z., and Sagar Lonial. Novel drug combinations for the management of relapsed/refractory multiple myeloma. Clinical Lymphoma Myeloma and Leukemia 14 (2014): S71-S77.

Wang FM, Chen YJ, and Ouyang HJ. Regulation of unfolded protein response modulator XBP1s by acetylation and deacetylation. Biochem J. 2011;433(1):245-52.

Wang, Feng-Ming, et al. Resveratrol triggers the pro-apoptotic endoplasmic reticulum stress response and represses pro-survival XBP1 signaling in human multiple myeloma cells. Experimental hematology 39.10 (2011): 999-1006.

Williams KW, Liu T, Kong X, Fukuda M, Deng Y, Berglund ED, Deng Z, Gao Y, Liu T, Sohn JW, et al. Xbp1s in Pomc neurons connects ER stress with energy balance and glucose homeostasis. Cell Metab. 2014;20(3):471-82.

Wong WL, Brostrom MA, Kuznetsov G, Gmitter-Yellen D, and Brostrom CO. Inhibition of protein synthesis and early protein processing by thapsigargin in cultured cells. Biochem J. 1993;289 71-79.

Xu FH, Sharma S, Gardner A, Tu Y, Raitano A, Sawyers C, and Lichtenstein A. Interleukin-6-induced inhibition of multiple myeloma cell apoptosis: support for the hypothesis that protection is mediated via inhibition of the JNK/SAPK pathway. Blood. 1998;92(1):241-51.

Xu G, Liu K, Anderson J, Patrene K, Lentzsch S, Roodman GD, and Ouyang H. Expression of XBP1s in bone marrow stromal cells is critical for myeloma cell growth and osteoclast formation. Blood. 2012;119(18):4205-14.

Yang Y, Ikezoe T, Saito T, Kobayashi M, Koeffler HP, and Taguchi H. Proteasome inhibitor PS-341 induces growth arrest and apoptosis of non-small cell lung cancer cells via the JNK/c-Jun/AP-1 signaling. Cancer Sci. 2004;95(2):176-80.

Yasuda H, Shima N, Nakagawa N, Yamaguchi K, Kinosaki M, Mochizuki S, Tomoyasu A, Yano K, Goto M, Murakami A, et al. Osteoclast differentiation factor is a ligand for osteoprotegerin/osteoclastogenesis-inhibitory factor and is identical to TRANCE/RANKL. Proc Natl Acad Sci U S A. 1998;95(7):3597-602.

Yoshida H, Matsui T, Yamamoto A, Okada T, and Mori K. XBP1 mRNA is induced by ATF6 and spliced by IRE1 in response to ER stress to produce a highly active transcription factor. Cell. 2001;107(7):881-91.

Yoshida H, Oku M, Suzuki M, and Mori K. pXBP1(U) encoded in XBP1 pre-mRNA negatively regulates unfolded protein response activator pXBP1(S) in mammalian ER stress response. J Cell Biol. 2006;172(4):565-75.

International Search Report and Written Opinion dated Oct. 12, 2018, from International Application No. PCT/US2018/040227, 13 pages.

Ming et al. "A novel chemical, STF-083010, reverses tamoxifen-related drug resistance in breast cancer by inhibiting IRE1/XBP1", Oncotarget, vol. 6, No. 38, 2015, 12 pages.

Chae et al. "Criticical role of XBP1 in cancer signalling is regulated by PIN1", Biochem. J. (2016) 473, 2603-2610.

```
181 DSGGIDSSDSESDILLGILDNLDPVMFFKCPSPEPASLEELPEVYPEGPSSLPASLSLSV 240
    000000000000000000000000000000 ++++++++++++++++++++++++++++++
                                                   P1
241 GTSSAKLEAINELIRFQHIYTKPLVLEIPSETESQANVVVKIEEAPLSPSENDHPEFIVS 300
    +++++                         000000000000000 ++++++++++++
                                                        P2
301 VKEEPVEDQLVPELGISNLLSSSHCPKPSSCLLDAYSDCGYGGSLSPFFSDMSSLLGVNHS 360
    0000000000000000000000000000 000000000000000000000000000000 0

361 WEDTFANELFPQLISV 376
    0000000000000000

Symbols   PEST Motifa
+++++++   Potenital
0000000   poor
```

FIG. 11A

```
                                                                    p2
239 SVGTSSAKLEAINELIRFDHIYTKPLVLEIPSETESQANVVVKIEEAPLSPSENDHPEFIVSVKEEPVEDDLVPELGISN 318
234 SVGTSSAKLEAINELIRFDHVYTKPLVLEIPSETESQTNVVVKIEEAPLSSSEEDHPEFIVSVKKEPLEDDFIPELGISN 313
```

FIG. 15A

METHODS FOR PREDICTING AND DETERMINING RESPONSIVENESS TO ACTIVATORS OF JNK KINASE

CROSS REFERENCE TO RELATED APPLICATIONS

This application claims priority to PCT International Application No. PCT/US2018/040198, filed Jun. 29, 2018, which claims the benefit of U.S. Provisional Patent Application Ser. No. 62/527,296, filed Jun. 30, 2017, the disclosures of which are expressly incorporated herein by reference.

STATEMENT REGARDING FEDERALLY SPONSORED RESEARCH

This invention was made with government support under Grant Nos. CA182418, DE017439, and CA161150 awarded by the National Institutes of Health. The government has certain rights in the invention.

FIELD

The present disclosure relates to methods for predicting and/or determining responsiveness to an activator of JNK kinase activity. The present disclosure further relates to improved methods for treating a cancer patient with an activator of JNK kinase activity. The present disclosure also relates to methods for screening for a modulator of XBP1s protein phosphorylation.

BACKGROUND

Multiple myeloma (MM) is an incurable neoplastic disease of B cell origin and the most frequent cancer to involve the skeleton. MM induces MM bone disease (MMBD), which is characterized by purely osteolytic lesions that rarely heal even after the eradication of tumor cells by chemo-radiation treatment (Mitsiades et al., *Cancer Cell*, 6:439-444 (2004); Roodman et al., *Blood Cells Mol. Dis.*, 32:290-292 (2004)). The bone marrow microenvironment plays a critical role in supporting both tumor growth and bone destruction in MMBD (Hideshima et al., *Nat. Rev. Cancer*, 7:585-598 (2007)). Bone marrow stromal cells (BMSCs) are a key player in microenvironmental support of MM cell growth and bone destruction. BMSCs produce multiple growth factors and inflammatory cytokines, such as IL-6, RANKL and VCAM-1, to enhance MM cell growth and activate osteoclasts, the bone resorbing cells, to induce osteolytic lesions (Michigami et al., *Blood*, 96:1953-1960 (2000); Bataille et al., *J. Clin. Invest.*, 88:62-66 (1991); Roodman et al., *J. Bone Miner. Res.*, 17:1921-1925 (2002)). Further, drugs that target both MM cells and overcome stromal support of MM cells display superior clinical efficacy than those that only target MM cells (see Hideshima supra; Podar et al., *Leukemia*, 23:10-24 (2009)). Therefore, understanding the molecular mechanisms underlying bone marrow support of MMBD is crucial in order to identify novel drug targets for the prevention and/or reversal of MMBD as a means to improve the quality of life and enhance survival of MM patients (Roodman et al., *J. Bone Miner. Res.*, 17:1921-1925 (2002)).

It was previously reported that the human X-box binding protein 1 (hXBP1s) is a stromal-intrinsic oncogenic factor that enables BMSC support of MM cell growth and MM-induced bone destruction (Xu et al., *Blood*, 119:4205-4214 (2012)). XBP1s is a basic-region leucine zipper (bzip) transcription factor of the CREB-ATF protein family and a major proximal effector of the unfolded protein response (UPR) signaling. Xbp1 mRNA is spliced via an ER-localized endoribonuclease/kinase IRE1α to generate spliced Xbp1 mRNA, termed Xbp1s (Yoshida et al., *Cell*, 107:881-891 (2001); Calfon et al., *Nature*, 415:92-96 (2002)). Xbp1s encodes an active transcription factor (XBP1s) that drives the expression of a wide range of genes involved in the maintenance of intracellular protein homeostasis (He et al., *Gene Expr.*, 15:13-25 (2010); Byrd et al., *Cells*, 1:738-753 (2012)). While it was previously reported that MM patient BMSCs have increased levels of hXBP1s protein compared with normal donor BMSCs, the mechanisms and post-translational modifications are not understood.

JNKs kinase (c-Jun N-terminal kinases) is a stress activated protein kinase (SAPKs) kinase, belonging to the MAPK (mitogen activated protein kinases) family. JNKs can be activated in response to genotoxic environmental stress, e.g., ER stress (Johnson et al., *Biochim. Biophys. Acta.*, 1773:1341-1348 (2007)). ER stress induction of Xbp1s mRNA and activation of JNKs are both induced by IRE1, via its endoribonuclease and kinase activities, respectively (Urano et al., *Science*, 287:664-666 (2000)). However, it is unknown whether there is a biochemical and/or functional linkage between hXBP1s and JNKs and whether this linkage has pathological and clinical significance in mediating the therapeutic effects of MM drugs on disrupting BMSC support of MMBD.

The compounds, compositions, and methods disclosed herein address these and other needs.

SUMMARY

For the first time, the inventors have demonstrated that the XBP1s protein is a direct and physiological substrate of JNKs, which phosphorylates XBP1s protein at serine 288 (Ser288). In addition, the inventors have demonstrated that compounds which activate JNKs can increase the amount of XBP1s phosphorylated at Ser288 (occasionally referred to herein as p-XBP1$^{S288}$ or, in the case of humans, p-hXBP1s$^{S288}$) in human MM bone marrow, which correlates with a favorable clinical response to such compounds. Non-limiting examples of compounds which activate JNKs include bortezomib, dexamethasone, thalidomide, or any combination thereof. The identification of this protein modification provides a biomarker for predicting and determining the responsiveness of a patient to therapeutics that are activators of JNK kinase activity.

In one aspect, disclosed herein is a method for predicting responsiveness of a subject with a cancer to an activator of JNK kinase activity, the method comprising:
 a) obtaining a sample from the subject with cancer;
 b) determining in the sample the level of phosphorylation of XBP1s at position Ser288 of the amino acid sequence; wherein the level of phosphorylation is determined using an antibody that specifically binds to XBP1s phosphorylated at position Ser288 of the amino acid sequence; and
 c) comparing the level of a phosphorylation of XBP1s at position Ser288 of the amino acid sequence in the sample to a control sample, wherein an increase in the level of a phosphorylation of XBP1s at position Ser288 of the amino acid sequence as compared to the control sample indicates the responsiveness of a subject with cancer to an activator of JNK kinase activity.

In some embodiments, the cancer is multiple myeloma. In some embodiments, the control sample is from a healthy subject or a subject without cancer. In some embodiments, the method further comprising administering to the subject an activator of JNK kinase activity. In some embodiments, the activator of JNK kinase activity comprises bortezomib, dexamethasone, thalidomide, or any combination thereof.

In one aspect, disclosed herein is a method of monitoring the effectiveness of an activator of JNK kinase activity, the method comprising:
a) administering to a subject a compound that is an activator of JNK kinase activity.
b) obtaining a sample from the subject;
c) determining in the sample the level of phosphorylation of XBP1s at position Ser288 of the amino acid sequence; wherein the level of a phosphorylation is determined using an antibody that specifically binds to XBP1s phosphorylated at position 288 of the amino acid sequence; and
d) comparing the level of a phosphorylation of XBP1s at position 288 of the amino acid sequence in the sample to a control sample, wherein an increase in the level of a phosphorylation of XBP1s at position 288 of the amino acid sequence as compared to the control sample indicates the effectiveness of the activator of JNK kinase activity.

In some embodiments, the subject has cancer (e.g., is suffering from a cancer). In some embodiments, the cancer is multiple myeloma. In some embodiments, the control sample is from the subject prior to administration of the activator of JNK kinase activity. In some embodiments, the method further comprising administering one or more additional doses of the activator of JNK kinase activity to the subject if the method indicates the activator of JNK kinase activity is effective. In some embodiments, the activator of JNK kinase activity comprises bortezomib, dexamethasone, thalidomide, or any combination thereof.

In another aspect, disclosed herein is a method for treating a subject with a cancer, the method comprising:
a) obtaining a sample from the subject with a cancer;
b) determining in the sample the level of phosphorylation of XBP1s at position Ser288 of the amino acid sequence; wherein the level of phosphorylation is determined using an antibody that specifically binds to XBP1s phosphorylated at position Ser288 of the amino acid sequence; and
c) comparing the level of a phosphorylation of XBP1s at position Ser288 of the amino acid sequence in the sample to a control sample, wherein an increase in the level of a phosphorylation of XBP1s at position Ser288 of the amino acid sequence as compared to the control sample indicates the responsiveness of a subject with cancer to an activator of JNK kinase activity;
d) administering to the subject a therapeutically effective amount of an activator of JNK kinase activity if an increase in the level of a phosphorylation of XBP1s at position Ser288 of the amino acid sequence is detected.

In some embodiments, the cancer is multiple myeloma. In some embodiments, the control sample is from a healthy subject or a subject without cancer. In some embodiments, the activator of JNK kinase activity comprises bortezomib, dexamethasone, thalidomide, or any combination thereof. In some embodiments, the method further comprising administering to the subject an additional therapeutic agent.

In a further aspect, disclosed herein is a method for screening for a modulator of phosphorylation of XBP1s at position Ser288 of the amino acid sequence, the method comprising:
a) contacting a cell with at least one candidate therapeutic agent;
b) determining in the cell the level of phosphorylation of XBP1s at position Ser288 of the amino acid sequence, wherein the level of phosphorylation is determined using an antibody that specifically binds to XBP1s phosphorylated at position Ser288 of the amino acid sequence; and
c) comparing the level of a phosphorylation of XBP1s at position Ser288 of the amino acid sequence in the cell to a control cell;
d) wherein an increase or decrease in the level of a phosphorylation of XBP1s at position Ser288 of the amino acid sequence as compared to a control cell indicates the at least one candidate therapeutic agent is a modulator of phosphorylation of XBP1s at position Ser288 of the amino acid sequence.

In some embodiments, the control cell is a cell that has not treated with the candidate therapeutic agent. In some embodiments, the method is performed in a 96-well microtiter plate or 384-well microtiter plate.

BRIEF DESCRIPTION OF THE DRAWINGS

The accompanying figures, which are incorporated in and constitute a part of this specification, illustrate several aspects described below.

FIG. 1(A-G) shows JNKs regulate hXBP1s protein stability. FIG. 1B) for 30 minutes, then DTT was washed away (time point: 0), and the cells harvested at various time points after the DTT removal. At the indicated time points, whole cell lysates were subjected to Western blotting with the indicated antibodies. The band intensity was quantified by software Image J. The expression of both hXBP1s and p-JNKs at all the time points were normalized to the loading control β-actin and presented as the fold change over the zero time point.

FIG. 2(A-H) shows E3 ubiquitin ligase β-TrCP targets hXBP1s protein for JNK-dependent degradation.

FIG. 3(A-D) shows hXBP1s is a physiological substrate of JNK phosphorylation. FIG. 3C: p-hXBP1s$^{S288}$ could not be detected in hXBP1s S288A mutant overexpressing HEK293T cells. hXBP1s-WT or S288A mutant was co-transfected with a mixture of MKK7-JNKs, and the transfected cells were then lysed and analyzed by Western blotting with the anti-phospho-hXBP1s$^{S288}$ antibody. FIG. 3D: p-hXBP1s$^{S288}$ was upregulated with increasing amount of introduced mixture of MKK7-JNKs in hXBP1s-WT overexpressing HEK293T cells. hXBP1s-WT was co-transfected with increased amounts of a mixture of MKK7-JNKs constructs into HEK293T cells. The transfected cells were then lysed and analyzed by Western blotting with anti-phospho-hXBP1s S288 antibody. MG132 was used to treat transfected cells in C and D to increase the abundance of phospho-hXBP1s$^{S288}$ protein.

FIG. 4(A-G) shows JNKs phosphorylate hXBP1 on Ser288 to trigger its degradation.

FIG. 5(A-F) shows deregulation of phosphorylation of hXBP1 at Ser288 in BMSCs facilitates the stromal support of MM growth and osteoclastogenesis in vitro. FIG. 5A: KM101 cells that stably overexpress either hXBP1s WT or hXBP1s S288A mutant were treated with 10 ng/ml of TNFα for different periods of time (upper panel) or different doses of TNFα for 24 hrs (lower panel). The expression of VCAM-1 protein was analyzed by Western blotting. FIG. 5B: The same cell lines as described in FIG. 5A were treated with TNFα for 24 hrs. The expression of both mRNA and protein of IL-6 were measured by real-time RT-PCR (upper panel) and ELISA (lower panel), respectively. The mRNA expression of IL-6 in hXBP1s S288A-overexpressing KM101 cells was normalized to that in hXBP1s WT-overexpressing cells. FIG. 5C: The same cell lines under same treatment as described in panel FIG. 5B were subjected to real-time RT-PCR analysis of both OPG and RANKL expression. The expression of either OPG or RANKL mRNA in hXBP1s S288A-overexpressing KM101 cells were normalized to that in hXBP1s WT-overexpressing cells (upper panel). The same set of data was also presented as the ratio of RNAKL vs OPG, a critical indicator for the stromal capacity to support osteoclastogenesis, and then shown in lower panel. FIG. 5D: KM101 cells expressing either XBP1s WT or S288A mutant were grown to form monolayer and then treated with TNFα for 24 hrs. Different types of cells were added to the KM101 monolayer and the cell-cell adhesion was measured. FIG. 5E: The engineered KM101 cells as described in FIG. 5D were co-cultured with either ABNL-6 (upper panel) or 5-TGM (lower panel). The myeloma cell growth was measured. FIG. 5F: The engineered KM101 cells as described in FIG. 5D were co-cultured with primary mouse monocytes. The formation of OCL was visualized by TRAP staining (left panel) and further quantified (right panel). The results were produced in three independent experiments, each with three replicates. The scale bars from graphs in FIGS. 5B, 5C, 5D, 5E and 5F indicate ±SD. *P<0.05; **P<0.01 are produced by 2-tailed Student t-test.

FIG. 6(A-H) shows deregulation of phosphorylation of hXBP1 on Ser288 in BMSCs facilitates the stromal support of MM growth and osteoclastogenesis in vivo.

FIG. 7(A-F) shows S288 phosphorylation of hXBP1s mediates JNKs' inhibition of the stromal inflammatory signature and affects the therapeutic effects of MM drugs targeting JNKs.

FIG. 9(A-F) shows hXBP1s is an unstable protein and its mRNA expression is not affected by JNKs' activities.

FIG. 10(A-C) shows mRNA expression of hXBP1s was not affected by alteration of β-TrCP and JNKs.

FIG. 11(A-D) shows disruption of predicted phosphorylation sites of hXBP1s other than S288 or DSG-like motif did not affect JNKs-mediated phosphorylation or protein degradation of hXBP1s. FIG. 11A: Illustration of two PEST sequences in hXBP1s protein predicted by PESTfinder program.

FIG. 12(A-C) shows hXBP1s S288A mutant is resistant to JNK activity-induced alteration in protein turnover. In FIGS. 12B and 12C, the expression of either hXBP1s WT or S288A mutant protein at all the time points was quantified by band densitometry, normalized to loading control and presented as fold change over the zero-time point. The results were produced in three independent experiments, each with three replicates. The scale bars from FIGS. 12B and 12C indicate ±SD.

FIG. 15(A-B) shows Mouse ortholog of human XBP1s is resistant to protein degradation mediated by β-TrCP and JNK. FIG. 15A: Alignment of the protein sequences of XBP1s from human and mouse organism. The region containing PEST-2 sequence was shown. S/TP site does not exist in PEST-2 sequence of mouse XBP1s protein.

DETAILED DESCRIPTION

Figure 1A:
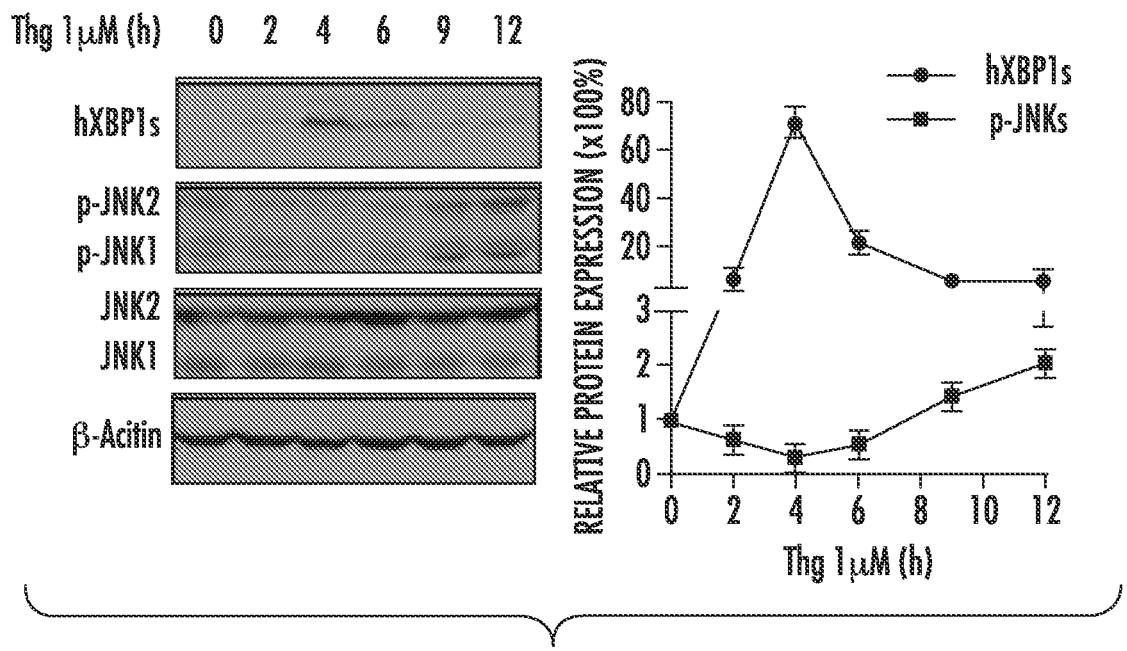
FIG. 1A and FIG. 1B: The protein expression of endogenous hXBP1s reversely correlated with those of p-JNKs during ER stress. HEK293T cells were treated with ER stress inducer thapsigargin (Thg) and were harvested at the indicated time points, or were treated with dithiothreitol (DTT.

As disclosed herein, the inventors have demonstrated that the XBP1s protein is a direct and physiological substrate of JNKs, which phosphorylates XBP1s protein at serine 288 (Ser288). In addition, the inventors have demonstrated that compounds which activate JNKs can increase the amount of XBP1s phosphorylated at Ser288 (occasionally referred to herein as p-XBP1s$^2$ or, in the case of humans, p-hXBP1s$^{S288}$) in human MM bone marrow, which correlates with a favorable clinical response to such compounds. Non-limiting examples of compounds which activate JNKs include bortezomib, dexamethasone, thalidomide, or any combination thereof. The identification of this protein modification provides a biomarker for predicting and determining the responsiveness of a patient to therapeutics that are activators of JNK kinase activity.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "a cell" includes a plurality of cells, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

Grammatical variations of "administer," "administration," and "administering" to a subject include any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

For oral administration, oral compositions such as tablets and capsules may be in unit dose form, and may contain excipients such as binding agents, for example syrup, acacia, gelatin, sorbitol, tragacanth, or polyvinyl-pyrrolidone: fillers for example lactose, sugar, maize-starch, calcium phosphate, sorbitol or glycine; tableting lubricant, for example magnesium stearate, talc, polyethylene glycol or silica: disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia: non-aqueous vehicles (which may include edible oils), for example almond oil, fractionated coconut oil, oily esters such as glycerine, propylene glycol, or ethyl alcohol; preservatives, for example methyl or propyl phydroxybenzoate or sorbic acid, and if desired conventional flavoring or coloring agents.

As used here, the terms "beneficial agent" and "active agent" are used interchangeably herein to refer to a chemical compound or composition that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage. In some embodiments, treating includes reducing the size of a tumor or reducing the number of tumors. In some embodiments, treating can include increasing the overall anti-tumor inflammatory response, for example as measured by markers of inflammation such as cytokines or infiltration of anti-tumor immunological cells, as understood by one of skill in the art. In some embodiments, treating includes remission of a cancer disorder.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts. An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "mixture" can include solutions in which the components of the mixture are completely miscible, as well as suspensions and emulsions, in which the components of the mixture are not completely miscible.

As used herein, the term "subject" or "host" or "patient" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

The terms "specific binding" or "specifically binds", as used herein, in reference to the interaction of an antibody, a protein, or a peptide with a second chemical species, mean that the interaction is dependent upon the presence of a particular structure (e.g., an "antigenic determinant" or "epitope" as defined below) on the chemical species, for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. Thus, under designated conditions (e.g. immunoassay conditions), a specified ligand or antibody "specifically binds" to its particular target (e.g. an antibody specifically binds to an antigen) when it does not bind in a significant amount to other proteins present in the sample or to other proteins to which the ligand or antibody may come in contact with. Generally, a first molecule that "specifically binds" a second molecule has an affinity constant (Ka) greater than about $10^5$ $M^{-1}$ (e.g., $10^6$ $M^{-1}$, $10^8$ $M^{-1}$, $10^9$ $M^{-1}$, $10^9$ $M^{-1}$, $10^{10}$ $M^{-1}$, $10^{11}$ $M^{-1}$, and $10^{12}$ $M^{-1}$ or more) with that second molecule.

"XBP1" refers to X-Box Binding Protein 1 polypeptide or a polynucleotide which encodes such a polypeptide. XBP1 is also known as Tax-Responsive Element-Binding Protein 5, TREG-5, TREB5, and XBP-1 and, in humans, is encoded by the XBP1 gene. The human XBP1 polypeptide can be referred to as hXBP1. Spliced mRNA encoding XBP1 can be referred to as Xbp1s and hence, the encoded polypeptide can also be referred to as XBP1s, as occasionally used herein. In some embodiments, the XBP1 polypeptide or polynucleotide is that identified in one or more publicly available databases as follows: HGNC: 12801 Entrez Gene: 7494 Ensembl: ENSG00000100219 OMIM: 194355 UniProtKB: P17861. In some embodiments, the XBP1s polypeptide is human XBP1s (hXBP1s). In some embodiments, the XBP1 polypeptide has an amino acid sequence which is at least 70%, at least 80%, at least 90%, at least 95%, or at least 99% identical to SEQ ID NO: 1. In some embodiments, the XBP1 polypeptide has an amino acid sequence comprising SEQ ID NO: 1.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains at least some portion of the epitope binding features of an Ig molecule (for example, allowing it to specifically bind to phosphorylated XBP1s). An antibody is said to be "capable of binding" a molecule if it is capable of specifically reacting with the molecule to thereby bind the molecule to the antibody.

Methods

In one aspect, disclosed herein is a method for predicting responsiveness of a subject with a cancer to an activator of JNK kinase activity, the method comprising:
  a) obtaining a sample from the subject with cancer;
  b) determining in the sample the level of phosphorylation of XBP1s at position Ser288 of the amino acid sequence; wherein the level of phosphorylation is determined using an antibody that specifically binds to XBP1s phosphorylated at position Ser288 of the amino acid sequence; and
  c) comparing the level of a phosphorylation of XBP1s at position Ser288 of the amino acid sequence in the sample to a control sample, wherein an increase in the level of a phosphorylation of XBP1s at position Ser288 of the amino acid sequence as compared to the control sample indicates the responsiveness of a subject with cancer to an activator of JNK kinase activity.

By "predicting responsiveness" it is meant that the method can predict whether a subject will benefit therapeutically from administration of a compound (e.g., an activator of JNK kinase activity) to the subject. In some embodiments, the degree of responsiveness can be directly associated with the level of phosphorylation detected in the methods.

In some embodiments, the control sample is from a healthy subject or a subject without cancer.

In some embodiments, the method further comprises administering to the subject an activator of JNK kinase activity. In some embodiments, the activator of JNK kinase activity comprises bortezomib, dexamethasone, thalidomide, or any combination thereof.

In one aspect, disclosed herein is a method of monitoring the effectiveness of an activator of JNK kinase activity, the method comprising:
  a) administering to a subject a compound that is an activator of JNK kinase activity;
  b) obtaining a sample from the subject;
  c) determining in the sample the level of phosphorylation of XBP1s at position Ser288 of the amino acid sequence; wherein the level of a phosphorylation is determined using an antibody that specifically binds to XBP1s phosphorylated at position 288 of the amino acid sequence; and
  d) comparing the level of a phosphorylation of XBP1s at position 288 of the amino acid sequence in the sample to a control sample, wherein an increase in the level of a phosphorylation of XBP1s at position 288 of the amino acid sequence as compared to the control sample indicates the effectiveness of the activator of JNK kinase activity.

In some embodiments, the subject has cancer (e.g., is suffering from a cancer). In some embodiments, the cancer is multiple myeloma. In some embodiments, the control sample is from the subject prior to administration of the activator of JNK kinase activity. In some embodiments, the method further comprising administering one or more additional doses of the activator of JNK kinase activity to the subject if the method indicates the activator of JNK kinase activity is effective. In some embodiments, the activator of JNK kinase activity comprises bortezomib, dexamethasone, thalidomide, or any combination thereof.

In another aspect, disclosed herein is a method for treating a subject with a cancer, the method comprising:
  a) obtaining a sample from the subject with a cancer;
  b) determining in the sample the level of phosphorylation of XBP1s at position Ser288 of the amino acid sequence; wherein the level of phosphorylation is determined using an antibody that specifically binds to XBP1s phosphorylated at position Ser288 of the amino acid sequence;
  c) comparing the level of phosphorylation of XBP1s at position Ser288 of the amino acid sequence in the sample to a control sample; and
  d) administering to the subject a therapeutically effective amount of an activator of JNK kinase activity if an increase in the level of phosphorylation of XBP1s at position Ser288 of the amino acid sequence is detected.

In another aspect, disclosed herein is a method for treating a subject with a cancer, the method comprising:
  a) obtaining a sample from the subject with a cancer;
  b) determining in the sample the level of phosphorylation of XBP1s at position Ser288 of the amino acid sequence; wherein the level of phosphorylation is determined using an antibody that specifically binds to XBP1s phosphorylated at position Ser288 of the amino acid sequence;
  c) comparing the level of phosphorylation of XBP1s at position Ser288 of the amino acid sequence in the sample to a control sample, wherein an increase in the level of phosphorylation of XBP1s at position Ser288 of the amino acid sequence as compared to the control sample indicates the responsiveness of a subject with cancer to an activator of JNK kinase activity: and
  d) administering to the subject a therapeutically effective amount of an activator of INK kinase activity if an increase in the level of phosphorylation of XBP1s at position Ser288 of the amino acid sequence is detected.

In some embodiments, the cancer is multiple myeloma. In some embodiments, the control sample is from a healthy subject or a subject without cancer. In some embodiments, the activator of JNK kinase activity comprises bortezomib, dexamethasone, thalidomide, or any combination thereof. In some embodiments, the method further comprising administering to the subject an additional therapeutic agent.

A sample can be obtained from a subject by standard medical, clinical, surgical, and/or phlebotomy techniques, and the sample can be further processed as required (e.g., purification, culture, storage) in preparation for or in accompaniment with performing measurements thereon (e.g., determining a level of phosphorylation). In some embodiments, the sample comprises a portion of a tumor or a suspected tumor. In some embodiments, the sample comprises a bodily fluid (e.g., blood, lymph or plasma) containing or suspected of containing cancerous cells.

The level of phosphorylation of a protein such as XBP1s can be measured or determined by any means known in the art for determining protein phosphorylation status or levels. For example, a level of phosphorylation can be determined by detecting a radiolabel (e.g., incorporated $^{32}$P-labeled phosphate), by detection of kinase reaction byproducts such as adenosine diphosphate, or by phosphospecific antibody techniques. In the latter technique, an antibody is used which specifically binds a phosphorylated form of the target protein but does not bind the target protein in the unphosphorylated form. The amount of antibody bound to the phosphorylated form of the target protein can then be determined by numerous methods known in the art, including but not limited to immunodetection (secondary antibody detection in e.g., a Western blot or ELISA), detection of a conjugated fluorophore, measurement of a conjugated catalytic domain (e.g., horse-radish peroxidase), or other methods of quantifying amounts of specifically-bound antibodies.

In some embodiments, the level of phosphorylation is determined using an antibody that specifically binds to phosphorylated XBP1s but not to unphosphorylated XBP s. In some embodiments, the site of phosphorylation of XBP1s is a serine residue. In some embodiments, the antibody binds phosphorylated XBP1s at the serine at position 288 (referred to as Ser288) of the XBP1s amino acid sequence. As used herein, the amino acid sequence, when used in reference to XPB1s, refers to any herein disclosed XPB1s amino acid sequence. It is expressly understood and contemplated herein that the serine at position 288 of the consensus human XPB1s amino acid sequence (e.g., SEQ ID NO:1) may be at a different position in different subjects. This may be the case for two subjects of different species, or even for two separate subjects of the same species (e.g., two separate humans). As such, it is expressly understood and contemplated that the term "position Ser288 of the amino acid sequence" refers to the homologous or orthologous serine of an XBP1 polypeptide having an amino acid sequence which is at least 70%, at least 80%, at least 90%, at least 95%, or at least 99% identical to SEQ ID NO: 1. Thus, the serine residue which is homologous or orthologous to the serine at position 288 of, for example SEQ ID NO:1, may or may not be at position 288 in the homologous or orthologous polypeptide sequence.

"Identical" or percent "identity," in the context of two or more polynucleotide or polypeptide sequences, refer to two or more sequences or subsequences that are the same or have a specified percentage of amino acid residues or nucleotides that are the same (e.g., at least 70%, at least 80%, at least 90%, at least 95%, or at least 99% identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence (e.g., SEQ ID NO: 1), to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues: always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The level of phosphorylation of XBP1s (for example, at position Ser288 of the amino acid sequence) in the sample can be compared to a control sample. Such a comparison can be used to determine whether the level of phosphorylation is increased, decreased, or substantially unchanged. The control can comprise a biological sample, or alternatively, a collection of values used as a standard applied to one or more subjects (e.g., a general number or average that is known and not identified in the method). In some embodiments, the control comprises a biological sample from a healthy subject or a subject without cancer. Alternatively, the control can comprise a biological sample of the subject, for instance a tissue or collection of cells from the subject which are known or suspected to be non-cancerous. In embodiments in which the effectiveness of an activator of JNK kinase activity is monitored, the control sample can be from the subject prior to administration of the activator of JNK kinase activity, whereas the sample can be from the subject after administration of the activator of JNK kinase activity. In such embodiments, the control and the sample can be from the same tissue (e.g., a cancerous or tumorous tissue).

The comparison between the level of phosphorylation of XBP1s in the sample and the control can indicate numerous outcomes. In some embodiments, the comparison an increase in the level of a phosphorylation of XBP1s at position Ser288 compared to the control indicates responsiveness of a subject to an activator of INK kinase activity. Alternatively, such an increase can indicate effectiveness of the activator of JNK kinase activity. In other embodiments, such an increase can indicate a candidate therapeutic agent is a modulator of phosphorylation of XBP1s at position Ser288.

The degree of increased phosphorylation of XBP1s in the sample compared to a control required to determine a particular outcome can vary depending on the outcome the measurement is used to indicate. For instance, the amount of increased phosphorylation in a sample compared to a control which indicates responsiveness of a subject to an activator of JNK kinase activity can be the same or different amount than that which indicates effectiveness of the activator of JNK kinase activity. In some embodiments, the level of phosphorylation of XBP1s in the sample is increased by at least 10% compared to a control. In some embodiments, the level of phosphorylation of XBP1s in the sample is increased by at least 20%, at least 30%, at least 40%, at least 50%, at least 60%, at least 70%, at least 80%, at least 90%, at least 100%, at least 200%, at least 500%, or at least 1,000% compared to a control.

The methods can include administering to the subject one or more activators of JNK kinase activity. Such administrations can include at least one, at least two, at least three, at least four, at least five, at least six, at least seven, at least eight, at least nine, or at least ten dosages. An activator of JNK kinase activity and/or other therapeutic compound can be administered before the subject exhibits disease symptoms (e.g., prophylactically), or during or after disease symptoms occur. The administering step can be performed prior to, concurrent with, or subsequent to administration of other agents to the subject. In some embodiments, the administering step is performed prior to, concurrent with, or subsequent to the administration of one or more additional diagnostic or therapeutic agents.

In some embodiments, a subsequent administration is provided at least one day after a prior administration, or at least two days, at least three days, at least four days, at least five days, or at least six days after a prior administration. In some embodiments, a subsequent administration is provided at least one week after a prior administration, or at least two weeks, at least three weeks, or at least four weeks after a prior administration. In some embodiments, a subsequent administration is provided at least one month, at least two months, at least three months, at least six months, or at least twelve months after a prior administration.

The amount of the disclosed compositions administered to a subject will vary from subject to subject, depending on the nature of the disclosed compositions and/or formulations, the species, gender, age, weight and general condition of the subject, the mode of administration, and the like. Effective dosages and schedules for administering the compositions may be determined empirically, and making such determinations is within the skill in the art. The dosage ranges for the administration of the disclosed compositions are those large enough to produce the desired effect (e.g., to reduce tumor size). The dosage should not be so large as to outweigh benefits by causing adverse side effects, such as unwanted cross-reactions, anaphylactic reactions, and the like. The dosage can be adjusted by the individual clinician in the event of any counterindications. Generally, the disclosed compositions and/or formulations are administered to the subject at a dosage of active component(s) ranging from 0.1 pig/kg body weight to 100 g/kg body weight. In some embodiments, the disclosed compositions and/or formulations are administered to the subject at a dosage of active component(s) ranging from 1 µg/kg to 10 g/kg, from 10 µg/kg to 1 g/kg, from 10 µg/kg to 500 mg/kg, from 10 µg/kg to 100 mg/kg, from 10 µg/kg to 10 mg/kg, from 10 µg/kg to 1 mg/kg, from 10 µg/kg to 500 µg/kg, or from 10 µg/kg to 100 µg/kg body weight. Dosages above or below the range cited above may be administered to the individual subject if desired.

In a further aspect, disclosed herein is a method for screening for a modulator of phosphorylation of XBP1s at position Ser288 of the amino acid sequence, the method comprising:

a) contacting a cell with at least one candidate therapeutic agent;

b) determining in the cell the level of phosphorylation of XBP1s at position Ser288 of the amino acid sequence; wherein the level of phosphorylation is determined using an antibody that specifically binds to XBP1s phosphorylated at position Ser288 of the amino acid sequence; and c) comparing the level of a phosphorylation of XBP1s at position Ser288 of the amino acid sequence in the cell to a control cell;

d) wherein an increase or decrease in the level of a phosphorylation of XBP1s at position Ser288 of the amino acid sequence as compared to a control cell indicates the at least one candidate therapeutic agent is a modulator of phosphorylation of XBP1s at position Ser288 of the amino acid sequence.

The cell contacted with at least one candidate therapeutic can be referred to as an experimental group. In some embodiments, the experimental cell and the control cell are the same cell type or are progeny of the same cell culture. In such embodiments, the control cell and the experimental cell generally differ in how each are treated. In some embodiments, the control cell is a cell that has not been treated with the candidate therapeutic agent. In some embodiments, the control cell is a cell that has been treated with a different agent. In some embodiments, the control cell is a cell that has been treated with a buffer that is the same as that used to treat the experimental cell except for the absence of the candidate therapeutic agent. Alternatively, the value used for the control cell can be a value used as a standard (e.g., a general number or average that is known or previously identified and not identified in each iteration of the method).

The cell can be any cell for which a therapeutic agent capable modulating phosphorylation of XBP1s at position Ser288 is sought. In some embodiments, the cell is a non-cancerous cell or, alternatively, is known or suspected to be a cancerous or tumor cell. In some embodiments, the cell is from a multiple myeloma. In some embodiments, the cell comprises a polypeptide having JNK kinase activity.

In some embodiments, the method is performed in a multi-well assay plate or microtiter plate (e.g., 6-well, 8-well, 12-well, 24-well, 36-well, 48-well, 96-well, or 384-well plate or microtiter plate).

In some embodiments, the level of phosphorylation of XBP1s at position Ser288 in the cell (the experimental cell) is increased or decreased by at least 10% compared to the control cell. In some embodiments, the level of phosphorylation of XBP1s in the cell is increased or decreased by at least 20%, at least 30%, at least 40%, at least 50%, at least 60%, at least 70%, at least 80%, at least 90%, at least 100%, at least 200%, at least 500%, or at least 1,000% compared to the control cell. An increase in the level of phosphorylation of XBP1s in the cell compared to the control cell indicates the candidate therapeutic agent (or combination of candidate therapeutics) is a positive modulator of XBP1s phosphorylation. A decrease in the level of phosphorylation of XBP1s in the cell compared to the control cell indicates the candidate therapeutic agent (or combination of candidate therapeutics) is a negative modulator of XBP1s phosphorylation. In some embodiments, the methods further comprise measuring the amount of ubiquitination or the amount of degradation of XBP1s after contacting the cell with the at least one candidate therapeutic agent. In such embodiments, an increase in the amount of ubiquitination or the amount of degradation of XBP1s can confirm that positive modulation of XBP1s phosphorylation by the candidate therapeutic agent results in increased ubiquitination or degradation of XBP1s. In some embodiments, the methods further comprise measuring cell survival after contacting the cell with the at least one candidate therapeutic agent. In such embodiments, an increase in cell survival can confirm that positive modulation of XBP1s phosphorylation by the candidate therapeutic agent results in increased cell survival.

The candidate therapeutic agent can be any agent capable of being screened in the methods disclosed herein, and include but are not limited to small molecules, compounds, biological compounds such as polypeptides (e.g., antibody), polynucleotides (e.g., siRNA), lipids, and polysaccharides, synthetic compounds or polymers, or any combination thereof. A positive therapeutic agent control can be included in the method, to which results of a candidate therapeutic agent can be compared. Positive therapeutic agent controls can include any agent disclosed herein to be an activator of JNK kinase activity (e.g., bortezomib, dexamethasone, thalidomide).

Also disclosed herein are methods for predicting responsiveness of a subject with a cancer to an activator of JNK kinase activity, the method comprising:
a) obtaining a sample from the subject with cancer, and
b) determining in the sample a presence of a serine at position 288 of a XBP1s amino acid sequence, wherein the presence of a serine at position 288 of the XBP1s amino acid sequence indicates the responsiveness of a subject to an activator of JNK kinase activity.

In some embodiments, the methods further comprise administering, if a serine is present at position 288 of the XBP1s amino acid sequence, one or more activators of JNK kinase activity, and not administering, if a serine is not present at position 288 of the XBP1s amino acid sequence, one or more activators of JNK kinase activity.

In some embodiments, the presence of a serine at position 288 of a XBP1s amino acid sequence can be determined by detecting the serine on a polypeptide present in the sample (e.g., by immunodetection). In some embodiments, the presence of a serine at position 288 of a XBP1s amino acid sequence can be determined by detecting a codon encoding the serine on a polynucleotide (e.g., DNA or mRNA) present in the sample (e.g., by polymerase chain reaction).

Also disclosed herein are methods for treating a subject with a cancer, the method comprising:
a) obtaining a sample from the subject;
b) determining in the sample a presence of a serine at position 288 of a XBP1s amino acid sequence: and
c) administering to the subject an activator of JNK kinase activity if a serine is present at position 288 of the XBP1s amino acid sequence.

In some embodiments, the methods comprise not administering to the subject an activator of JNK kinase activity if a serine is not present at position 288 of the XBP1s amino acid sequence.

In some embodiments, the presence of a serine at position 288 of a XBP1s amino acid sequence can be determined by detecting the serine on a polypeptide present in the sample (e.g., by immunodetection). In some embodiments, the presence of a serine at position 288 of a XBP1s amino acid sequence can be determined by detecting a codon encoding the serine on a polynucleotide (e.g., DNA or mRNA) present in the sample (e.g., by polymerase chain reaction).

Activators of JNK Kinase Activity

JNKs kinase (c-Jun N-terminal kinases) is a stress activated protein kinase (SAPKs) kinase, belonging to MAPK (mitogen activated protein kinases) family, the activation of which occurs in response to genotoxic, environmental stress, e.g ER stress. In the face of the latter, induction of Xbp1s mRNA and activation of JNKs are both induced by IRE1, respectively via its endoribonuclease and kinase activities. JNK kinase activation is induced by many multiple myeloma (MM) drugs' and potential therapeutic agents' treatment, such as dexamethasone, bortezomib, thalidomide, halofuginone, LPAAT-beta inhibitor, perifosine, and plinabulin, and activation of JNK is responsible for drug-induced apoptosis of multiple myeloma cells, demonstrating that JNKs are a major force responsible for the therapeutic effects of the drug.

The methods disclosed herein can be used with any agent that is an activator of JNK kinase activity. As disclosed herein, the term "activator of JNK kinase activity" refers to any agent (e.g., compound) activating or enhancing the catalytic activity of JNK compared to the level of said catalytic activity in the absence of said agent. In some embodiments, the catalytic activity of a JNK protein includes phosphorylation of a target (e.g., a protein comprising an amino acid capable of being phosphorylated), as compared to substantially similar conditions in which the agent is not present or is otherwise incapable of affecting JNK kinase activity (e.g., due to sequestration, degradation, presence of inhibitory factors, etc.). Non-limiting examples of activators of JNK kinase activity include, but are not limited to, bortezomib, dexamethasone, thalidomide, or any combination thereof.

In some embodiments, the activator of JNK kinase activity can include any small molecule, compound, biological agent, peptide, antibody, single or double stranded nucleic acid, or siRNA. In some embodiments, the activator of INK kinase activity comprises an agent which can be administered to a subject (e.g., a human).

In some embodiments, the activator of JNK kinase activity can comprise dexamethasone, bortezomib, thalidomide, halofuginone, LPAAT-beta inhibitor, perifosine, plinabulin, or any combination thereof. In some embodiments, the activator of JNK kinase activity is bortezomib. In some embodiments, the activator of JNK kinase activity is dexamethasone. In some embodiments, the activator of JNK kinase activity is thalidomide. In some embodiments, the activator of JNK kinase activity is halofuginone. In some embodiments, the activator of JNK kinase activity is LPAAT-beta inhibitor. In some embodiments, the activator of JNK kinase activity is perifosine. In some embodiments, the activator of JNK kinase activity is plinabulin. In some embodiments, the activator of INK kinase activity is BAY 11-7085 or anisomycin. In some embodiments, the activator of JNK kinase activity is BAY 11-7085 or anisomycin is MG132. In some embodiments, the activator of JNK kinase activity is Azaspiracid, AEBSF hydrochloride (Santa Cruz). In some embodiments, the activator of JNK kinase activity is Diallyl tetrasulfide (Abeam). In some embodiments, the activator of JNK kinase activity comprises one of the following combinations: bortezomib and dexamethasone; bortezomib and thalidomide; dexamethasone and thalidomide; or bortezomib, dexamethasone, and thalidomide.

Combination Therapies—Additional Chemotherapeutics

In some embodiments, the activator of JNK kinase activity is administered in combination with an additional therapeutic agent. In some embodiments, the additional therapeutic agent is an additional chemotherapeutic agent. In some embodiments, the additional chemotherapeutic agent is selected from cytarabine, daunorubicin, idarubicin, mitoxantrone, vincristine, Cladribine (Leustatin®, 2-CdA), Fludarabine (Fludara®). Topotecan, Etoposide (VP-16), 6-thioguanine (6-TG), Hydroxyurea (Hydrea®), Corticosteroid drugs, such as prednisone or dexamethasone (Decadron®), Methotrexate (MTX), 6-mercaptopurine (6-MP), Azacitidine (Vidaza®), or Decitabine (Dacogen®).

Cancers

In some embodiments, the subject has cancer (e.g., is suffering from a cancer). The cancer can be any cancer, including tumorous and non-tumorous cancers. In some embodiments, the cancer is a hematologic malignancy. In some embodiments, the cancer can include, but is not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others.

In some embodiments, the cancer is multiple myeloma (MM). In some embodiments, the cancer is acute myeloid leukemia (AML). In some embodiments, the acute myclogenous leukemia (AML) is cytogenetically normal acute myelogenous leukemia (CN-AML). In some embodiments, the leukemia is acute lymphoblastic leukemia (ALL).

In one embodiment, methods described herein are used for cancers or tumors or proliferative disorder such as, but not limited to: multiple myeloma; Diffuse large B cell lymphoma; Follicular lymphoma: Mucosa-Associated Lymphatic Tissue lymphoma (MALT); Small cell lymphocytic lymphoma; Mediastinal large B cell lymphoma; Nodal marginal zone B cell lymphoma (NMZL): Splenic marginal zone lymphoma (SMZL); Intravascular large B-cell lymphoma; Primary effusion lymphoma: or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+DLBCL of the elderly; Primary mediastinal (thymic) large B-cell lymphoma; Primary cutaneous DLBCL, leg type; ALK+large B-cell lymphoma; Plasmablastic lymphoma; Large B-cell lymphoma arising in HHV8-associated multicentric; Castleman disease, B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

As contemplated herein, the cancer can be a primary tumor or a metastatic tumor, or can be a non-solid cancer. In one aspect, the methods described herein can be used to treat a solid tumor, for example but not limited to, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma): breast cancer (including ductal carcinoma, lobular carcinoma, inflammatory breast cancer, clear cell carcinoma, mucinous carcinoma, serosal cavities breast carcinoma): colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer: prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor): liver and bile duct carcinoma (including hepatocellular carcinoma, cholangiocarcinoma, hemangioma); esophageal carcinoma (including esophageal adenocarcinoma and squamous cell carcinoma): oral and oropharyngeal squamous cell carcinoma: salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma Wilm's tumor): cancer of the head and neck (including squamous cell carcinomas); cancer of the stomach (gastric cancers, stomach adenocarcinoma, gastrointestinal stromal tumor): testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adrenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma renal cell carcinoma, hypemephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma. Islet cell carcinoma, malignant carcinoid, malignant paraganglioma, melanoma, Merkel cell neoplasm, cystosarcoma phylloide, salivary cancers, thymic carcinomas, and cancers of the vagina among others.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. JNKs-Mediated Phosphorylation of Human XBP1s in Bone Marrow Stromal Cells is Crucial for Myeloma Cell Growth and Osteoclast Formation While the transcriptional regulation and mRNA splicing of Xbp1 has been extensively studied, little is known about the posttranslational regulation of hXBP1s. Recently, it was reported that hXBP1s is subjected to acetylation and deacetylation by P300 and SIRT1 (member of the sirtuin family), respectively. Such modifications in turn control hXBP1s' transcriptional activity (Wang et al., Biochem. J., 433:245-252 (2011)). In addition, the hXBP1s transcriptional activity is reportedly regulated by SUMOylation (Chen et al., Biochem. J., 429:95-102 (2010)). Furthermore, murine XBP1s (mXBP1s) was found to be phosphorylated by murine p38 MAPK, a member of the family of serine (S)/threonine(T) protein kinases that play important roles in cellular stress responses (Coulthard et al., Trends Mol. Med., 15:369-379 (2009)). Phosphorylation of mXBP1s enhances its nuclear translocation in hepatocytes, regulating glucose homeostasis in hepatocytes of obese mice (Lee et al., Nat. Med., 17:1251-1260 (2011)). In addition, IκB kinase beta (IKKβ) can phosphorylate mXBP1s to increase the stability of the mXBP1s protein, and thus, reduce ER stress and improve insulin sensitivity and hepatic glucose homeostasis in the development of inflammation-induced insulin resistance (Liu et al., Cell, 167:1052-1066 (2016)). Thus, there is a pathophysiological significance of post-translational modifications of XBP1s in regulating XBP1s protein functions and numerous biological and pathological events, in which XBP1s is implicated.

JNKs kinase (c-Jun N-terminal kinases) is a stress activated protein kinase (SAPKs) kinase, belonging to the MAPK (mitogen activated protein kinases) family. JNKs can be activated in response to genotoxic environmental stress, e.g., ER stress (Johnson et al., Biochim. Biophys. Acta., 1773:1341-1348 (2007)). ER stress induction of Xbp1s mRNA and activation of JNKs are both induced by IRE1, via its endoribonuclease and kinase activities, respectively (Urano et al., Science, 287:664-666 (2000)). Interestingly, as noted in FIG. 1A and FIG. 1B, a decrease in hXBP1s protein levels coincides with an increase in the activity of JNKs in the ER stress response. This reverse relationship between XBP1s protein levels and activation of JNK suggests a possible regulation of hXBP1s by JNKs. JNKs are activated by many therapeutic agents for MM. including dexamethasone (Chauhan et al., Oncogene, 15:837-843 (1997)), bortezomib (Goranov et al., Folia. Med., 47:11-19 (2005): Hideshima et al., Blood, 101:1530-1534 (2003): Yang et al., Cancer Sci., 95:176-180 (2004): Roccaro et al., Curr. Pharm. Biotechnol., 7:441-448 (2006)), thalidomide (Anderson et al., Semin. Hematol., 42:S3-8 (2005)), Halofuginon (Leiba et al., Br. J. Haematol., 157: 718-731 (2012)), LPAAT-beta inhibitor (Hideshima et al., Cancer Res., 63:8428-8436 (2003)), Perifosine (Hideshima et al., Blood, 107:4053-4062 (2006)), and Plinabulin (Singh et al., Blood, 117:5692-5700 (2011)). The induction of JNK activity in MM cells induces apoptosis, contributing to the therapeutic effects of JNK-activating agents on MM (Singh et al., Blood, 117:5692-5700 (2011). Saha et al., PLoS One, 7:e30215 (2012); Xu et al., Blood, 92:241-251 (1998)). However, it is unknown whether there is a biochemical and/or functional linkage between hXBP1s and JNKs and whether this linkage has pathological and clinical significance in mediating the therapeutic effects of MM drugs on disrupting BMSC support of MMBD.

It is disclosed herein for the first time that hXBP1s is a direct and physiological substrate of JNKs. JNKs directly phosphorylates hXBP1s protein at serine 288 (Ser288). This phosphorylation promotes hXBP1s' physical interaction with the ubiquitin E3 ligase, β-TrCP, which in turn catalyzes the ubiquitination and protein degradation of hXBP1s. Moreover, in the context of MMBD, the de-phosphorylation of hXBP1s at Ser288 enhanced BMSC support of MM cell growth and OCL formation both in vitro and in vivo. Furthermore, it was observed that the combination of the JNKs-activating MM drugs, e.g., bortezomib, thalidomide, and/or dexamethasone, strongly induced the expression of p-hXBP1s$^{S288}$ protein in human MM patient BM specimens. Intriguingly, such phosphorylation positively correlates with favorable therapeutic responses to the MM drugs. Finally, it was found that the JNKs-activating reagents, including the MM drugs, repressed the stromal signature and/or BMSC support of MM cell growth. Such inhibition, however, was compromised in BMSCs expressing the JNKs-resistant mutant of hXBP1s. Taken together, these studies reveal that the JNKs-mediated phosphorylation is a novel molecular mechanism in regulating hXBP1s protein stability and mediating the therapeutic effects of the JNKs-activating MM drugs on the MM bone microenvironment. Thus, Ser288 phosphorylation of hXBP1s is as a valid biomarker for predicting the therapeutic outcomes of MM patients in response to JNKs-activating drugs.

Results

JNK Regulates XBP1 Protein Stability.

Figure 9A:
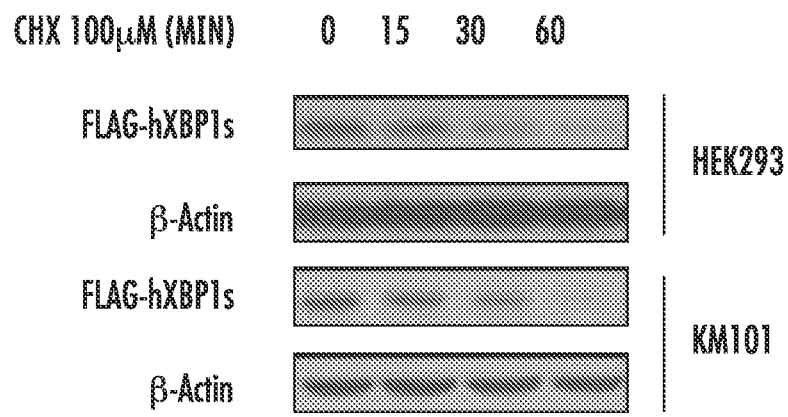
FIG. 9A: hXBP1s has a fast turnover rate. FLAG-hXBP1s-transfected HEK293T or overexpressing KM101 cells were treated with CHX. The protein expression of FLAG-hXBP1s at various time points of CHX treatment was determined by Western blotting.
Figure 9B:
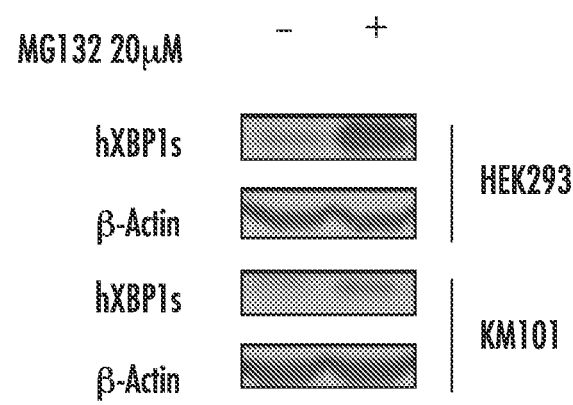
FIGS. 9B and 9C: MG 132 treatment caused the accumulation of both endogenous (FIG. 9B) and FLAG-tagged (FIG. 9C) hXBP1s protein in both HEK293T and KM101 cells.
Figure 9C:
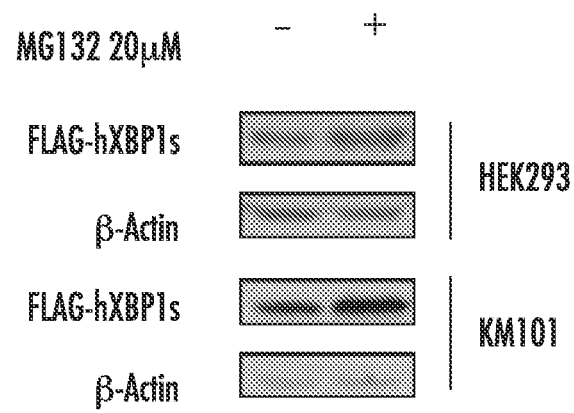
Figure 9D:
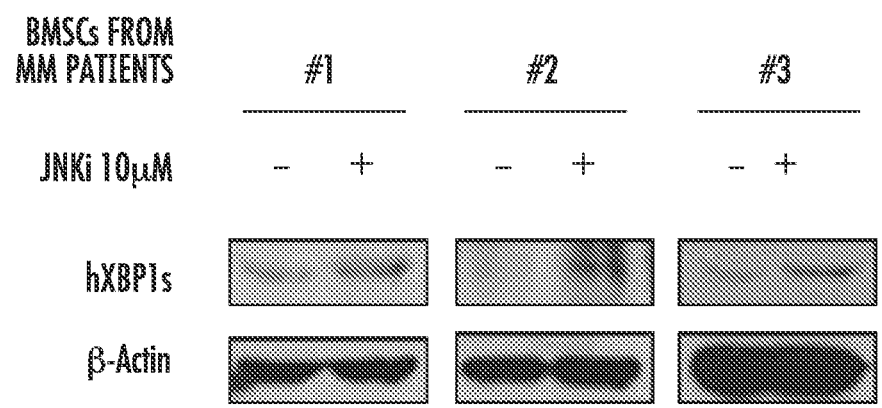
FIG. 9D: Treatment with JNK inhibitor, SP600125, caused an increase in endogenous hXBP1s protein expression in primary BMSCs derived from three multiple myeloma (MM) patients.

FIG. 9A shows that hXBP1s is a short-lived protein with a half-life of approximately 25 minutes, which is consistent with a previous report (Calfon et al., Nature, 415:92-96 (2002)). It was also found that treatment with the proteasome inhibitor MG132 promptly and greatly elevated the steady-state level of both the endogenous (FIG. 9B) and overexpressed hXBP1s (FIG. 9C) in both HEK293T and KM101 cells. Since MG132 specifically reduces proteasomal degradation of ubiquitin-conjugated proteins, these results suggested that hXBP1s protein is degraded by the proteasome complex. However, the molecular mechanism (s) controlling XBP1s protein stability were largely unknown.

hXBP1s plays an essential role in regulating BMSC support of MM cell growth. In an effort to understand the regulatory mechanisms underlying hXBP1s protein expression in MM patient BMSC, it was found that 2-hr treatment of BMSCs derived from three individual MM patients with SP600125, a pharmacological inhibitor of JNKs, resulted in a consistent increase in the steady-state protein levels of endogenous hXBP1s in all three patients (FIG. 9D). These results suggested that JNK might act as an inhibitor of hXBP1s in BMSCs. Further, JNKs and XBP1s are induced by ER stress and have opposite functions during ER stress (Hetz et al., *Mol. Cell.* 35:551-561 (2009)), suggesting that JNKs may negatively regulate hXBP1s protein expression and/or activity. To test this hypothesis, the time-dependent protein expression patterns of hXBP1s and phosphorylated JNKs (p-JNKs) was determined in cells that were challenged with either a persistent or transient ER stress, induced by either thapsigargin (Thg) or dithiothrietol (DTT), respectively. Western blot analysis demonstrated that Thg, a pharmacological agent disrupting the ER intraluminal calcium homeostasis (Wong et al., *Biochem. J.*, 289:71-79 (1993); Oslowski et al., *Methods Enzymol.*, 490:71-92 (2011)), induced a time-dependent up-regulation of endogenous hXBP1s, which was first detected at 2-hr of treatment and peaked at 4-hr. The protein level of hXBP1s started to decline at 6-hrs, and the reduction continued till 12-hr, the end of Thg treatment. In contrast, Thg induced the phosphorylation of JNKs from 6 to 12-hrs of Thg treatment. This activation of JNKs coincided with the decrease in hXBP1s protein levels within the same time frame of Thg treatment (FIG. 1A).

Figure 1B:
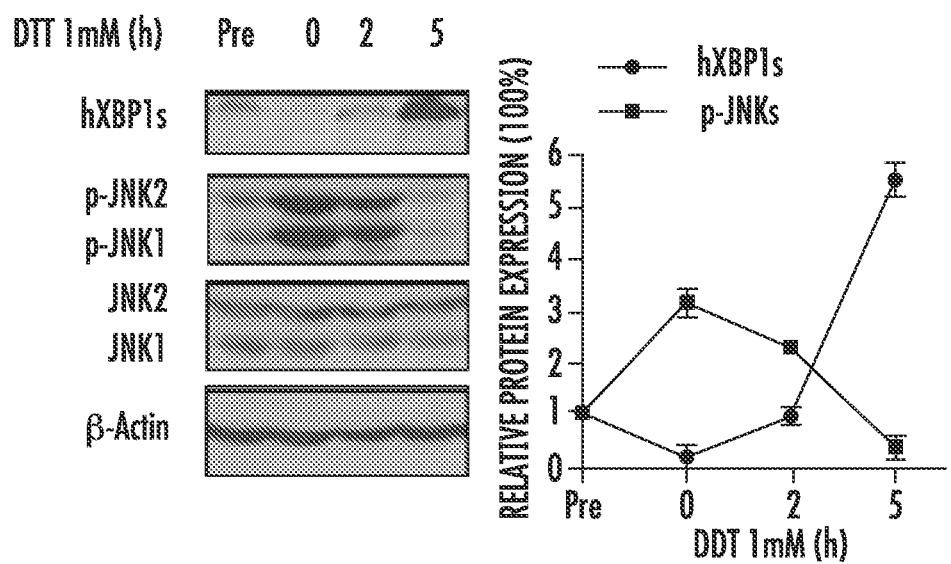

DTT is a reducing agent that disrupts oxidative protein folding in the ER. Since the effects of DTT are rapidly reversible, and DTT can be readily removed by washing, it was used to mimic intermittent ER stress on cells. HEK293T cells were treated with DTT for 30 minutes, then DTT was washed away, and the cells were harvested at various time points after DTT removal. Western blot analysis showed that 30-minute treatment of DTT quickly diminished basal hXBP1s protein expression, whereas it simultaneously and strongly induced phosphorylation of JNKs. In addition, the cells recovered and further increased hXBP is protein expression at 2- and 5-hr post DTT removal. This process coincided with a drastic reduction in JNKs' phosphorylation (FIG. 1B).

Figure 1C:
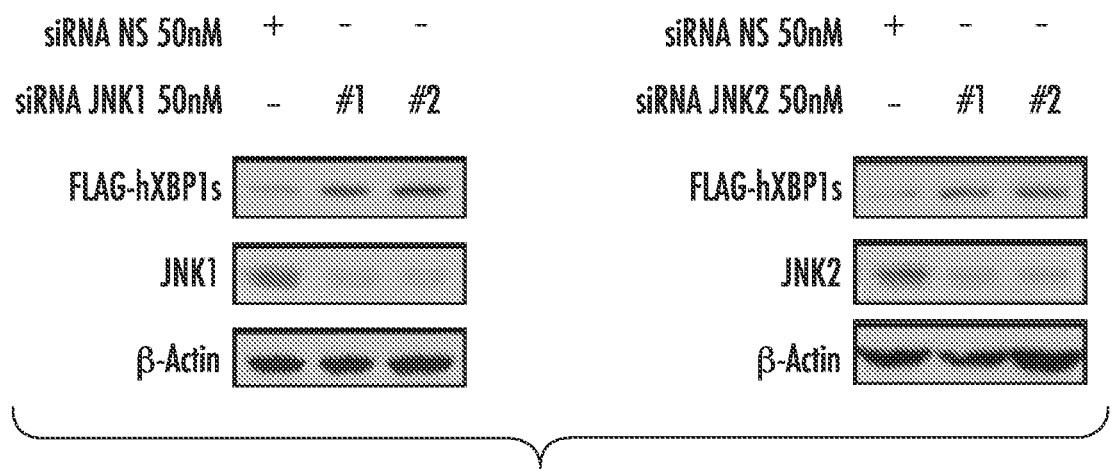
FIG. 1C: JNKs' knockdown caused an increase in FLAG-hXBP1s expression. BMSC line KM101 cells stably expressing FLAG-hXBP1s were transfected with two different siRNAs targeting JNK1 (left panel) or JNK2 (right panel). Nonsense siRNA served as control. Since JNK3 is not expressed in HEK293T 85, its role in hXBP1s protein regulation in HEK293T cells was not investigated here.
Figure 1D:
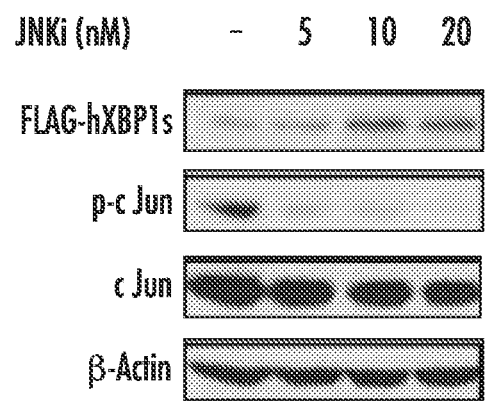
FIG. 1D: Treatment of KM101 cells with a pharmaceutical inhibitor for JNKs, JNKi VIII (JNKi), led to a dose-dependent upregulation of FLAG-hXBP1s. The decrease of c-Jun phosphorylation indicates JNK inhibition.
Figure 1E:
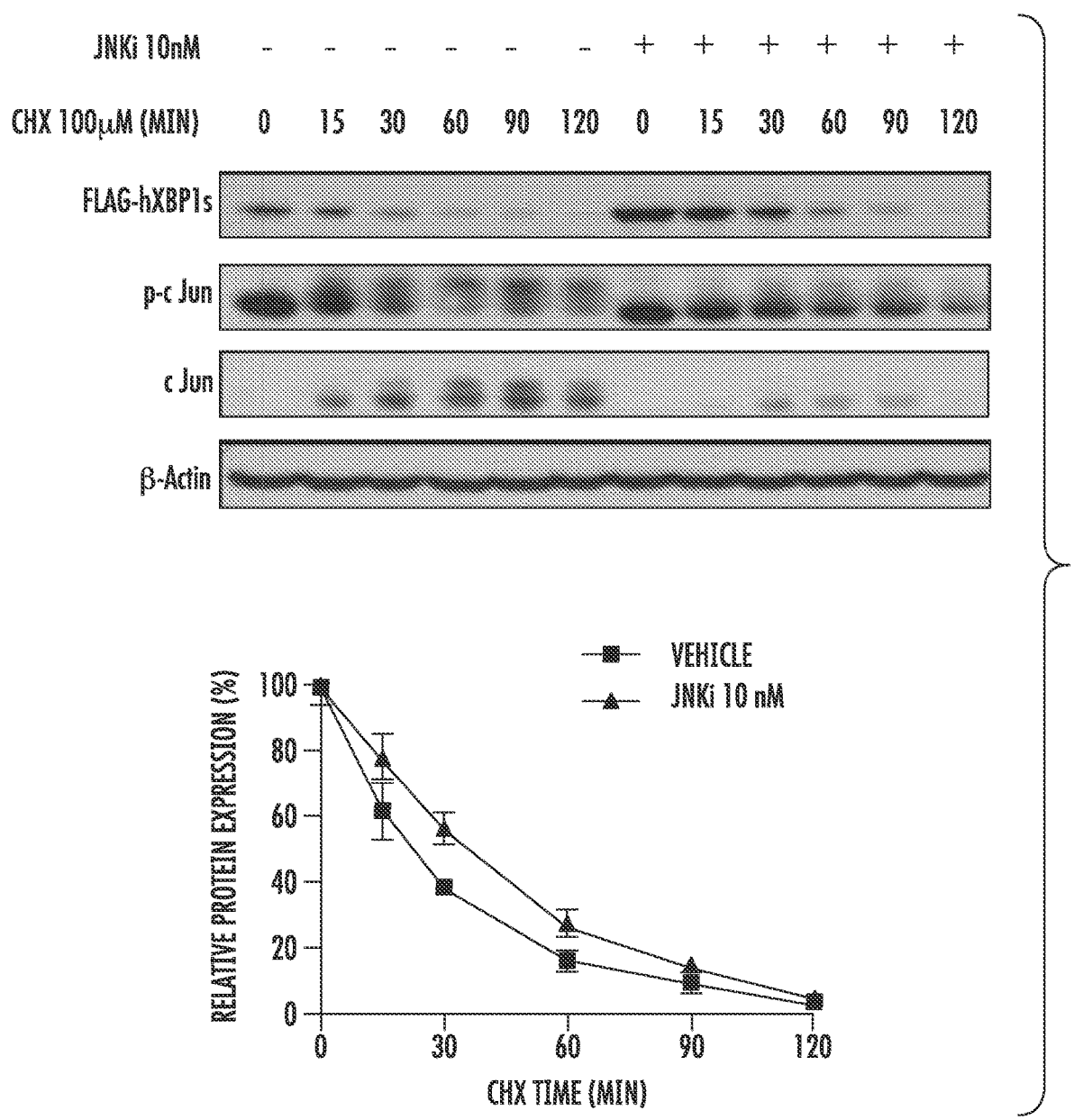
FIG. 1E: Treatment with JNKi stabilized FLAG-hXBP1s in KM101 cells. The cells were pre-treated JNKi and then treated with cycloheximide (CHX). The expression of FLAG-hXBP1s at various treatment time points was quantified by band densitometry, normalized to β-Actin and presented as fold change over the zero time point.
Figure 1F:
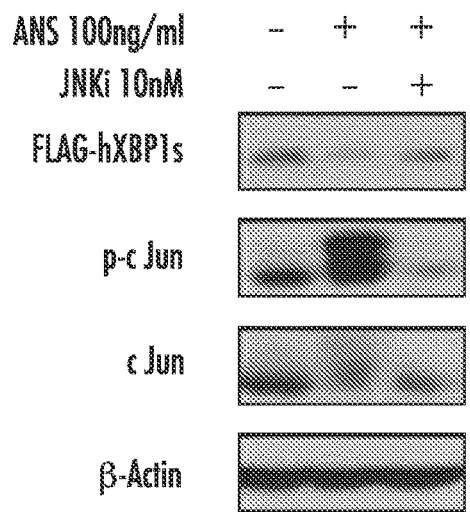
FIG. 1F: JNKi prevented anisomycin (ANS)-induced inhibition of FLAG-hXBP1s expression in KM101 cells. ANS is a MAPK kinase activator. FLAG-hXBP1s-overexpression KM101 cells were pre-treated with JNKi and then stimulated with 100 ng/ml of ANS.
Figure 1G:
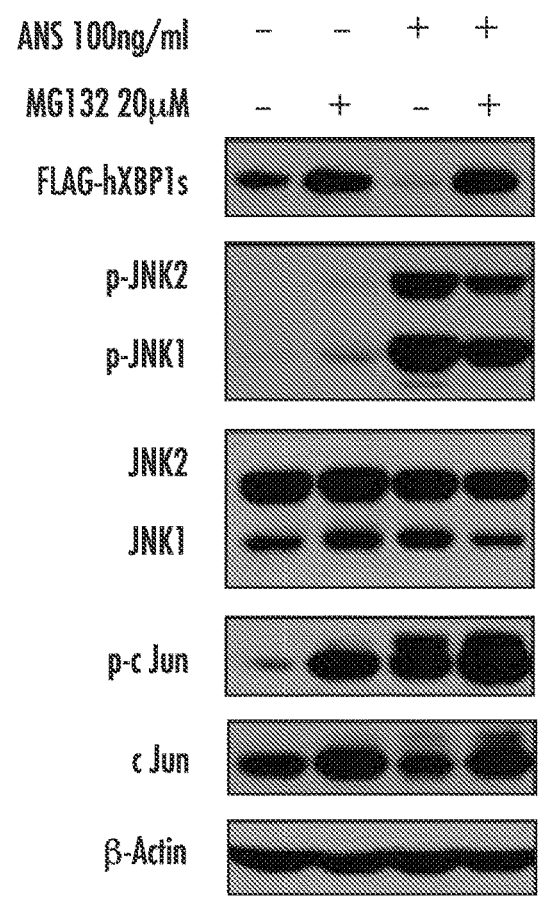
FIG. 1G: MG132 abolished ANS-induced downregulation of FLAG-hXBP1s in KM101 cells. FLAG-hXBP1s-overexpression KM101 cells were pre-treated with MG132, and then stimulated with ANS for 0.5 h. The results were produced in three independent experiments, each with three replicates. The scale bars from graphs in FIGS. 1A, 1B and 1E indicate ±SD.
Figures 2A, 2B:
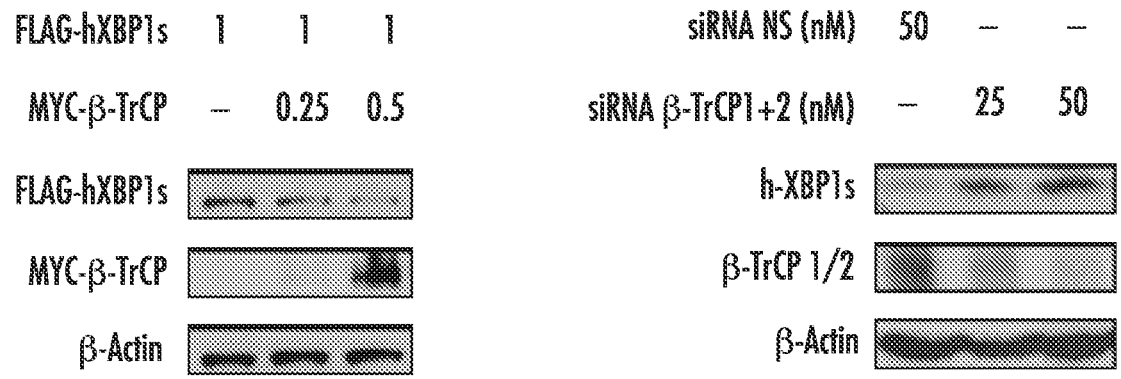
FIG. 2A: Overexpression of MYC-β-TrCP induced a dose-dependent decrease of FLAG-hXBP1s protein expression. HEK293T cells were co-transfected with FLAG-hXBP1s and an increased amount of MYC-β-TrCP constructs. The expression of FLAG-hXBP1s and MYC-β-TrCP protein were determined by Western blotting using the antibodies to FLAG and MYC tags.
FIG. 2B: Knocking down both endogenous β-TrCP1 and β-TrCP2 caused a dose-dependent increase of hXBP1s protein expression. HEK293T cells were transfected with increased amount of siRNA targeting both β-TrCP and β-TrCP2. The expressions of both hXBP1s and β-TrCP protein were determined by Western blotting.
Figure 2C:
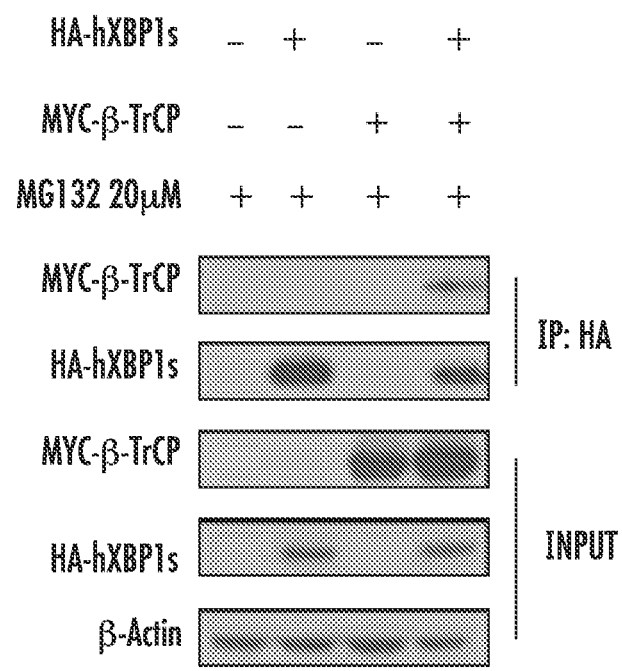
FIG. 2C: MYC-β-TrCP1 interacts with HA-hXBP1s. HEK293T cells transfected with MYC-β-TrCP1 and HA-hXBP1s constructs were treated with 10 µM MG132 for 4 hrs and then subjected to immunoprecipitation assay with HA tag antibody. The resulting immunoprecipitates were probed with MYC tag antibody for the expression of MYC-β-TrCP.
Figure 2D:
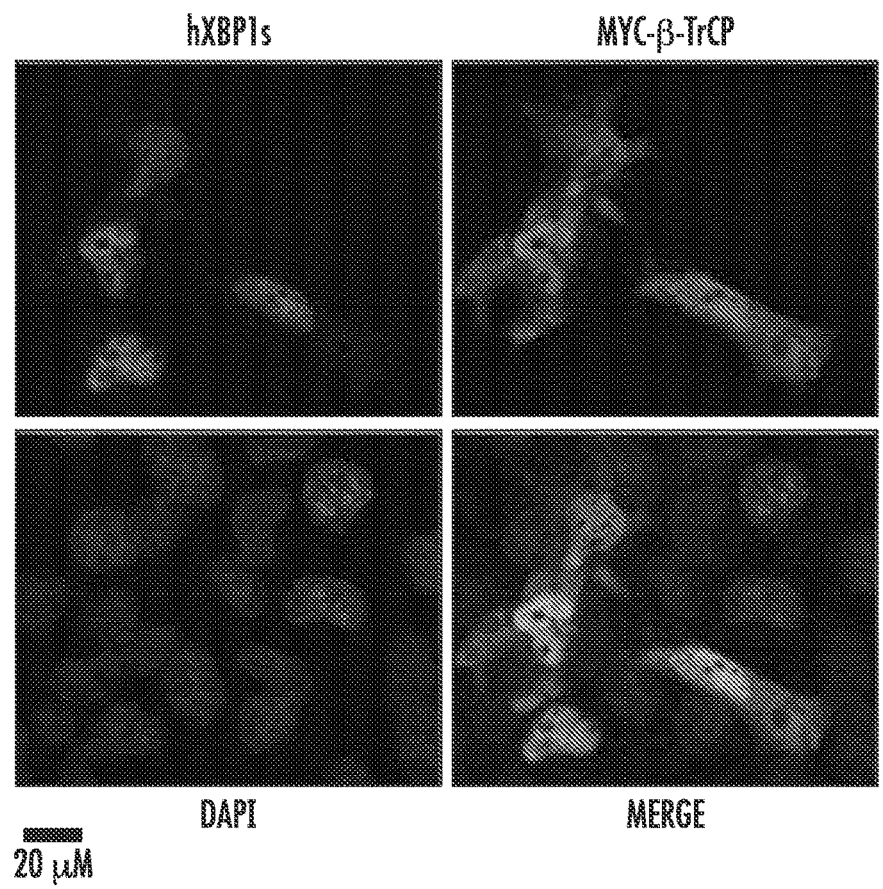
FIG. 2D: MYC-β-TrCP1 co-localizes with EGFP-hXBP1s. HEK293T cells transfected with HA-β-TrCP1 and EGFP-hXBP1s were sequentially stained with anti-HA and Cy3-conjugated secondary antibody and then imaged by co-focal microscopy. The nuclei were stained with DAPI.
Figure 2E:
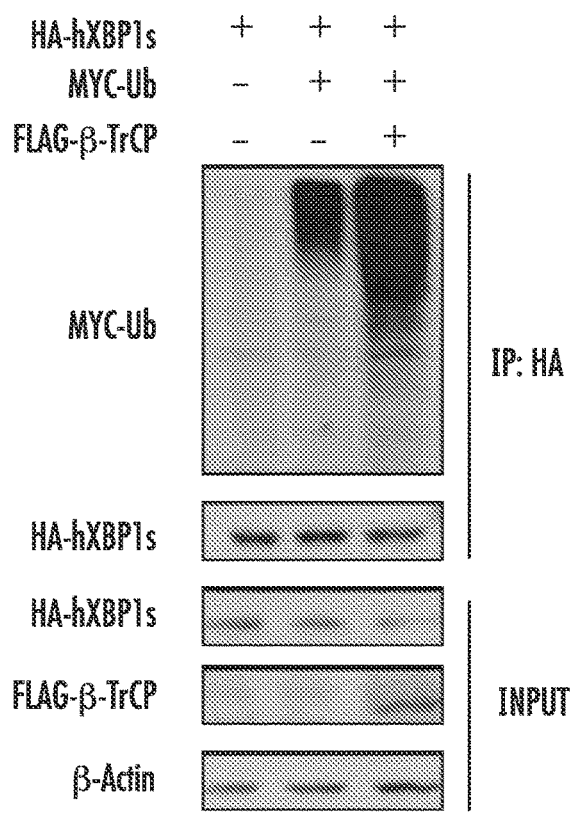
FIG. 2E: Overexpression of FLAG-f-TrCP promoted the conjugation of ubiquitin to HA-hXBP1s. HEK293T cells were co-transfected with HA-XBP1s. MYC-Ub and FLAG-β-TrCP1 constructs, treated with MG132 and then lysed for immunoprecipitation assay with anti-HA antibody. The resulting immunoprecipitates were probed with anti-MYC antibody for the expression of Ub-conjugate of HA-hXBP1s.
Figure 2F:
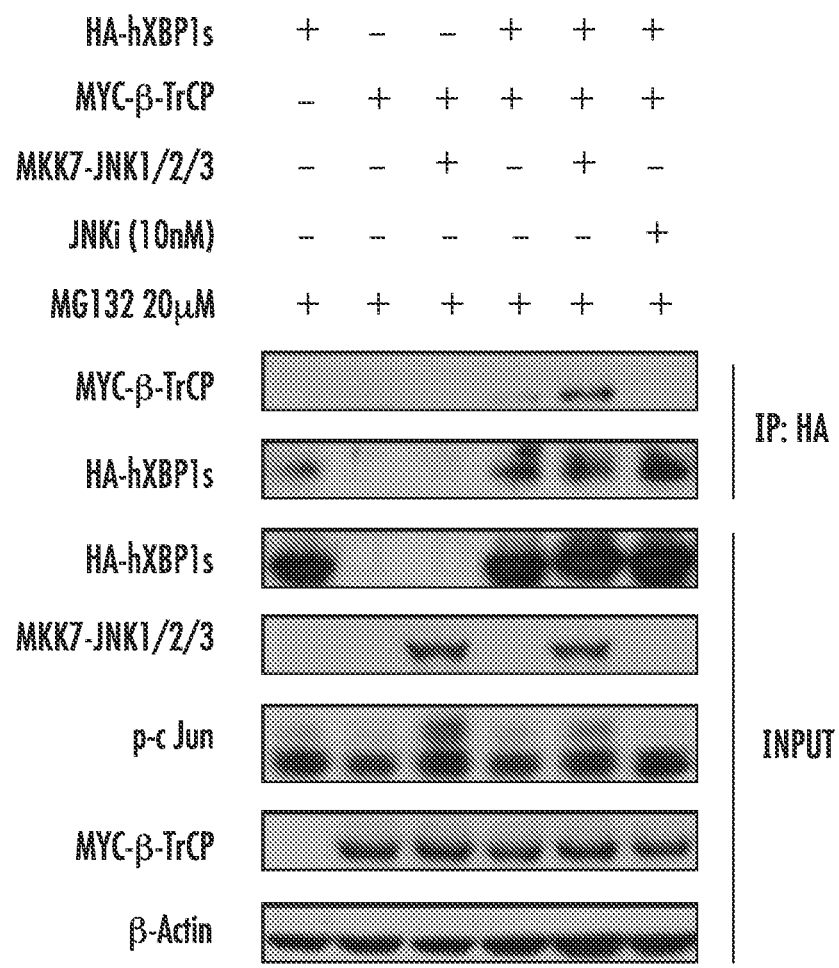
FIG. 2F: β-TrCP interaction with hXBP1s is regulated by JNK kinase activity. HEK293T cells transfected with HA-hXBP1s and MYC-β-TrCP1 were either co-transfected with a mixture of constitutively active JNK constructs, MKK7-JNK1, 2 and 3, and then treated with MG132, or directly treated with 10 nM JNKi for 4 hrs. Transfected cells under various treatment were finally subjected to immunoprecipitation assays.
Figure 2G:
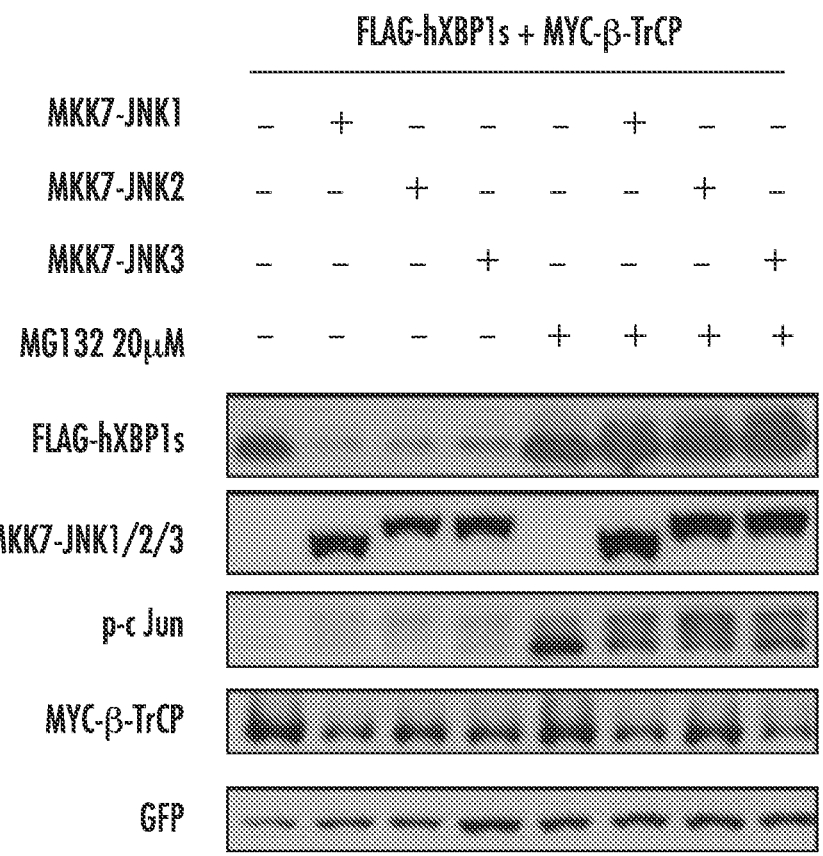
FIG. 2G: JNK activation promoted β-TrCP-dependent hXBP1s degradation. HEK293T cells were co-transfected with FLAG-hXBP1s, MYC-β-TrCP and any of three constitutively active JNKs. The transfected cells were then treated with or without MG132 and lysed for Western blotting. GFP served as a control for the transfection efficiency.
Figure 9E:
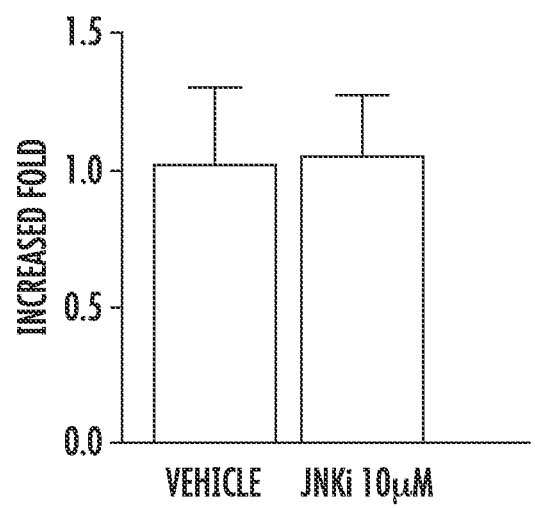
FIG. 9E: JNKi treatment did not affect the mRNA expression of hXBP1s. FLAG-hXBP1s-overexpressing KM101 cells were treated with JNKi and then lysed for Real-time PCR analysis.
Figure 9F:
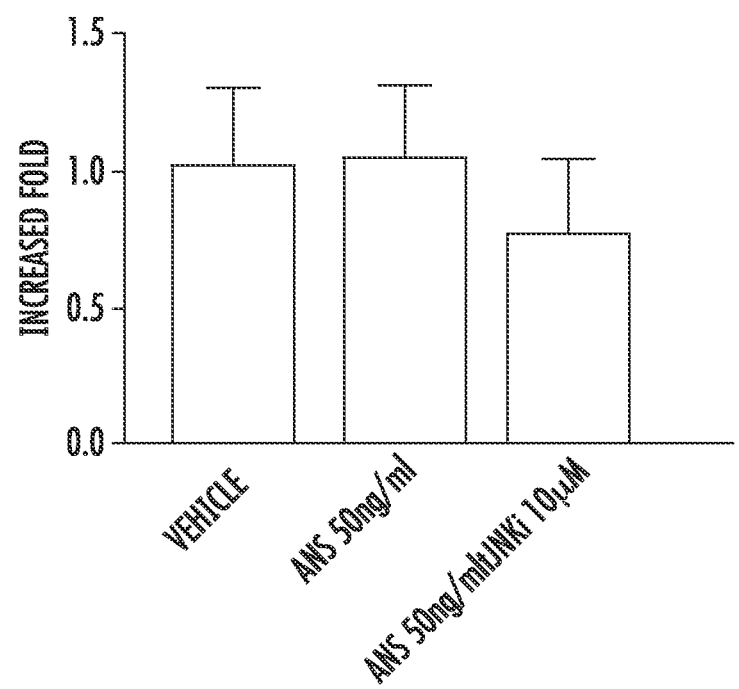
FIG. 9F: The mRNA expression of hXBP1s was not affected by the treatment with either ANS alone or ANS combined with JNKi. FLAG-hXBP1s-overexpressing KM101 cells were used. The results were produced in three independent experiments, each with three replicates. The scale bars from FIGS. 9E and 9F indicate SD.

Taken together, the negative association between protein expression of hXBP1s and p-JNKs during ER stress suggested a possible negative regulation by p-JNK of hXBP1s steady-state protein levels. In supporting this notion, it was found that siRNA downregulation of either JNK1 or JNK2 in KM101 cells led to an increased basal expression of overexpressed FLAG-hXBP1s in human bone stromal cell line KM101 cells (FIG. 1C). These results showed that both JNK1 and JNK2 can repress hXBP1s protein expression, and this inhibition is functionally redundant. In addition, pharmacologic inhibition of INKs by using the JNK inhibitor VIII (JNKi VIII) also resulted in a dose-dependent up-regulation of FLAG-hXBP1s in KM101 cells (FIG. 1D), thereby confirming the inhibitory effect of JNKs on the steady-state protein level of FLAG-hXBP1s. The inhibitor had no effect on mRNA expression of hXbp1s (FIG. 9E). Further, it was determined whether JNKs regulate the stability of FLAG-hXBP1s. For this purpose, KM101 cells were pretreated with JNKi VIII and the half-life of the FLAG-hXBP1s protein was measured. Cycloheximide (CHX) chase experiments demonstrated that the half-life of FLAG-hXBP1s protein was approximately 25 minutes and 40 minutes in the absence or presence of the JNK inhibitor, respectively (FIG. 1E). These results demonstrated that inhibition of JNKs stabilizes FLAG-hXBP1s. Conversely, anisomycin (ANS), a potent activator of JNKs and p38 (Hazzalin et al., *Mol. Cell. Biol.*, 18:1844-1854 (1998)), drastically decreased overexpressed FLAG-hXBP1s protein expression in KM101 cells (FIG. 1F). Importantly, since pretreating the cells with JNKi VIII largely prevented anisomycin-induced repression of FLAG-hXBP1s protein level (FIG. 1F), it was concluded that JNKs rather than p38 was responsible for anisomycin's inhibitory effect on the steady-state protein level of FLAG-hXBP1s. Moreover, it was found that anisomycin had no effect on hXbp1s mRNA levels (FIG. 9F), and that anisomycin-responsive reduction of FLAG-hXBP1s protein expression was completely blocked by MG132 (FIG. 1G). Finally, overexpression of the constitutively activated JNKs, e.g., MKK7-fused JNKs, markedly reduced the steady-state protein levels of FLAG-hXBP1s (FIG. 2G). Taken together, these results indicated that JNKs destabilize hXBP1s to decrease hXBP1s protein levels, and it does so via promoting hXBPs proteasomal degradation (Andley et al., *Essays Biochem.*, 41:15-30 (2005)).

E3 Ubiquitin Ligase β-TrCP Targets hXBP1s Protein for JNKs-Dependent Degradation.

Figure 10C:
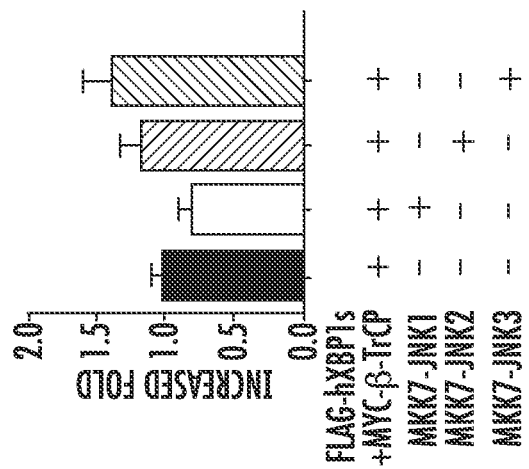
FIG. 10C: Co-expression of hXBP1s with either one of three constitutively active JNKs did not reduce hXBP1s mRNA expression. Results were produced in three independent experiments, each with three replicates. Scale bars from FIGS. 10B and 10C indicate SD.
Figure 10B:
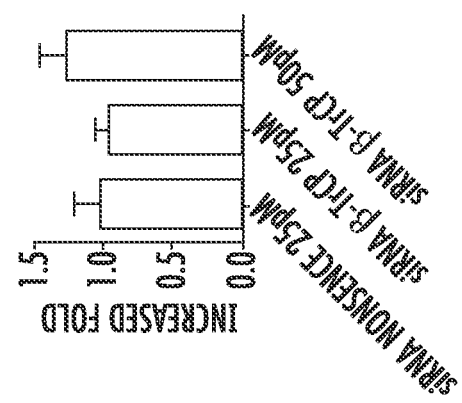
FIG. 10B: β-TrCP knockdown did not cause change of hXBP1s mRNA expression.
Figure 10A:
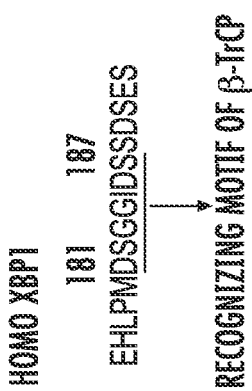
FIG. 10A: Illustration of β-TrCP recognizing motif within hXBP1s protein, predicted by the motif search program.

The Ubiquitin/Proteasome System (UPS) is a selectively proteolytic system that targets the ubiquitylation and turnover of short-lived proteins (see Ardley et al., supra). The selectivity of the UPS for a particular substrate protein relies on the interaction between ubiquitin-conjugating enzymes E2 and E3 ligases (see Ardley et al., supra). While the E2 is more universal. E3 is more substrate-specific. To identify the E3 ubiquitin ligase that is involved in the JNKs-dependent degradation of hXBP1s, the amino acid sequence of hXBP1s protein was analyzed and found to contain a DSG (DpSGΦXpS, where Φ represents a hydrophobic amino acid and X represents any amino acid)-like motif located in the central region of hXBP1s from amino acid position 181 to 187 (FIG. 10A). The DSG motif is often, but not always, a binding domain for β-TrCP, an F-box protein that belongs to the SCF$^{\beta\text{-}TrCP}$ E3 ubiquitin ligase complex (Fuchs et al., *Oncogene*, 23:2028-2036 (2004)). Thus, it was hypothesized that SCF$^{\beta\text{-}TrCP}$ was the E3 ubiquitin ligase responsible for hXBP1s degradation by promoting its ubiquitination. To test this hypothesis, HA tagged hXBP1s (HA-hXBP1s) was overexpressed in the presence or absence of a MYC-tagged β-TrCP (MYC-β-TrCP) construct in HEK293T cells. Western blot analysis showed that overexpression of MYC-β-TrCP induced a dose-dependent decrease of HA-hXBP1s protein levels in HEK293T cells (FIG. 2A). Conversely, siRNA knock-down of endogenous β-TrCP1 and β-TrCP2 resulted in a dose-dependent increase in the protein level of endogenous hXBP1s (FIG. 2B). The β-TrCP's siRNA had no effect on the mRNA expression of hXbp1s (FIG. 10B). Since hXBP1s harbors a DSG-like motif, a DP-TrCP binding domain (FIG. 10A), it was next determined whether hXBP1s and β-TrCP physically interact. Co-immunoprecipitation assays demonstrated that MYC-β-TrCP binds HA-hXBP1s (FIG. 2C). Consistent with these results, confocal imaging showed that MYC-β-TrCP co-localized with EGFP-hXBP1s in the nuclear compartments of the HEK293T cells (FIG. 2D). Finally, ubiquitination assays showed that ectopically expressed β-TrCP greatly promoted the conjugation of ubiquitin to HA-hXBP1s (FIG. 2E), indicating that f-TrCP targets hXBP1 to ubiquitin-proteasome pathway for degradation. Taken together, these results demonstrated that hXBP1s is a physiological substrate for the SCF$^{\beta\text{-}TrCP}$ E3 ubiquitin ligase.

Figure 2H:
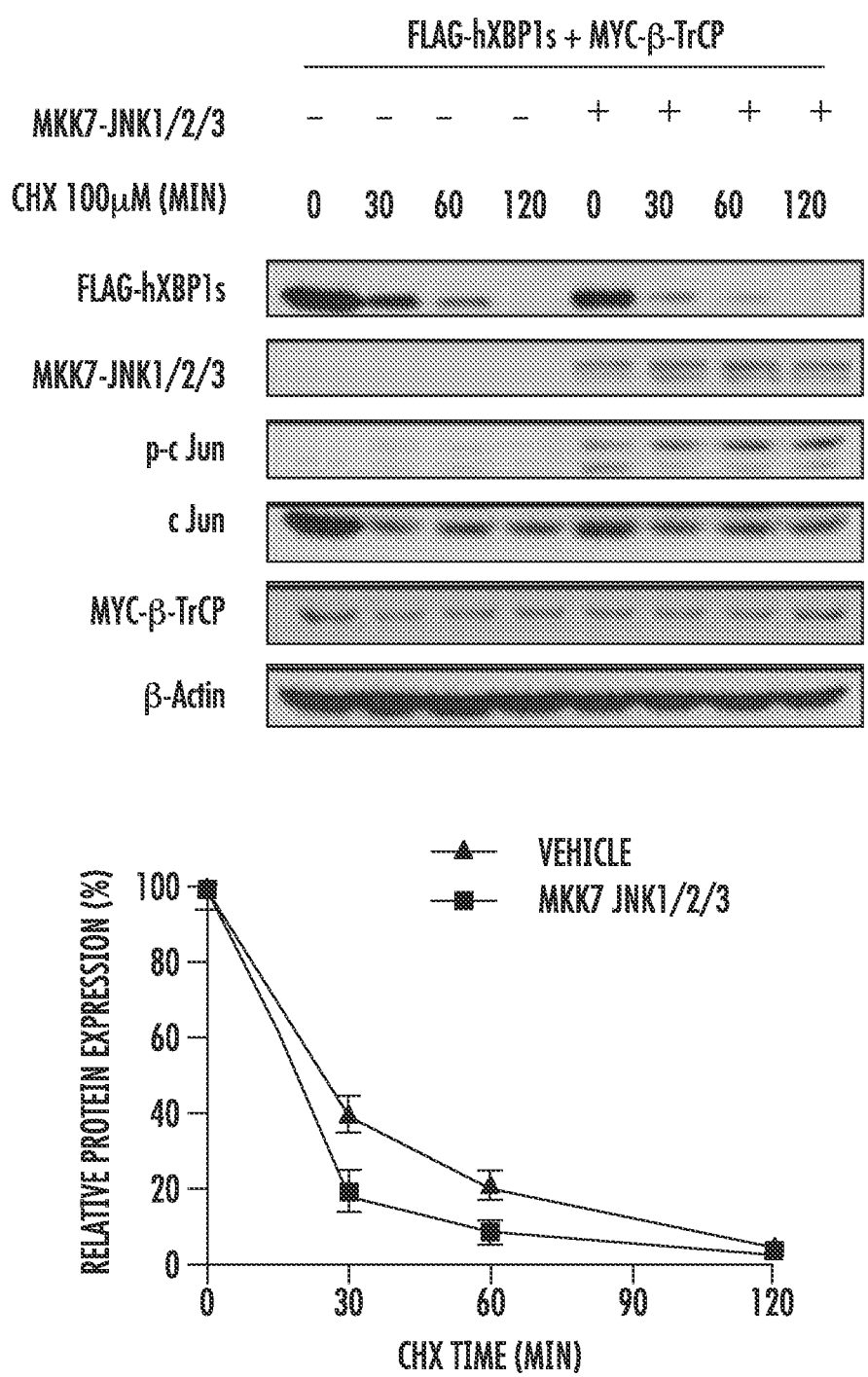
FIG. 2H: JNK activation destabilized hXBP1s. HEK293T cells were co-transfected with FLAG-hXBP1s, MYC-β-TrCP and a mixture of three constitutively active JNKs. The transfected cells were then treated with cycloheximide (CHX) and lysed at indicated time points for Western blotting analysis. The expression of hXBP1s protein was quantified by band densitometry. The results were produced in three independent experiments, each with three replicates. The scale bars indicate ±SD.

Since JNKs repress hXBP1s protein expression, it was hypothesized that JNKs promote its β-TrCP binding and consequent degradation via the UPS-26S proteasome machinery. In supporting this notion, co-immunoprecipitation assays and Western blot analysis demonstrated that pharmacological inhibition of JNKs activity by JNKi III abolished the basal level binding of HA-hXBP1s with MYC-β-TrCP (FIG. 2F). In contrast, overexpression of constitutively activated JNKs, MKK7-JNKs fusion constructs (Lei et al., *Mol. Cell. Biol.*, 22:4929-4942 (2002)), greatly enhanced the physical interaction between HA-hXBP1s and MYC-β-TrCP (FIG. 2F). To determine the functional consequence of JNKs' potentiation of the physical interactions between MYC-β-TrCP and HA-hXBP1s. FLAG-XBP1s was overexpressed with a small/moderate amount of MYC-β-TrCP either in the presence or absence of MKK7-JNKs. It was found that FLAG-hXBP1s expression was dramatically repressed in the presence of MKK7-JNKs (FIG. 2G), whereas under the identical experimental conditions, overexpressed MKK7-JNKs did not affect the mRNA levels of hXbp1s (FIG. 10C). Further, JNKs and MYC-β-TrCP's inhibition of FLAG-hXBP1s was abolished by pretreatment of cells with MG 132 (FIG. 2G). Consistent with the latter observation. CHX chase assays demonstrated that overexpression of the MKK7-JNKs shortened the half-life of FLAG-hXBP1s from its basal level 22 minutes to 12 minutes (FIG. 2H). Taking these observations together, it was concluded that JNKs promote the physical interactions between hXBP1s and D-TrCP, leading to the ubiquitination and consequent protein degradation of hXBP1s that results in a decrease in the steady-state levels of hXBP1s.

hXBP1s is a Novel, Physiological and Direct Substrate of JNKs' Phosphorylation.

Figure 3A:
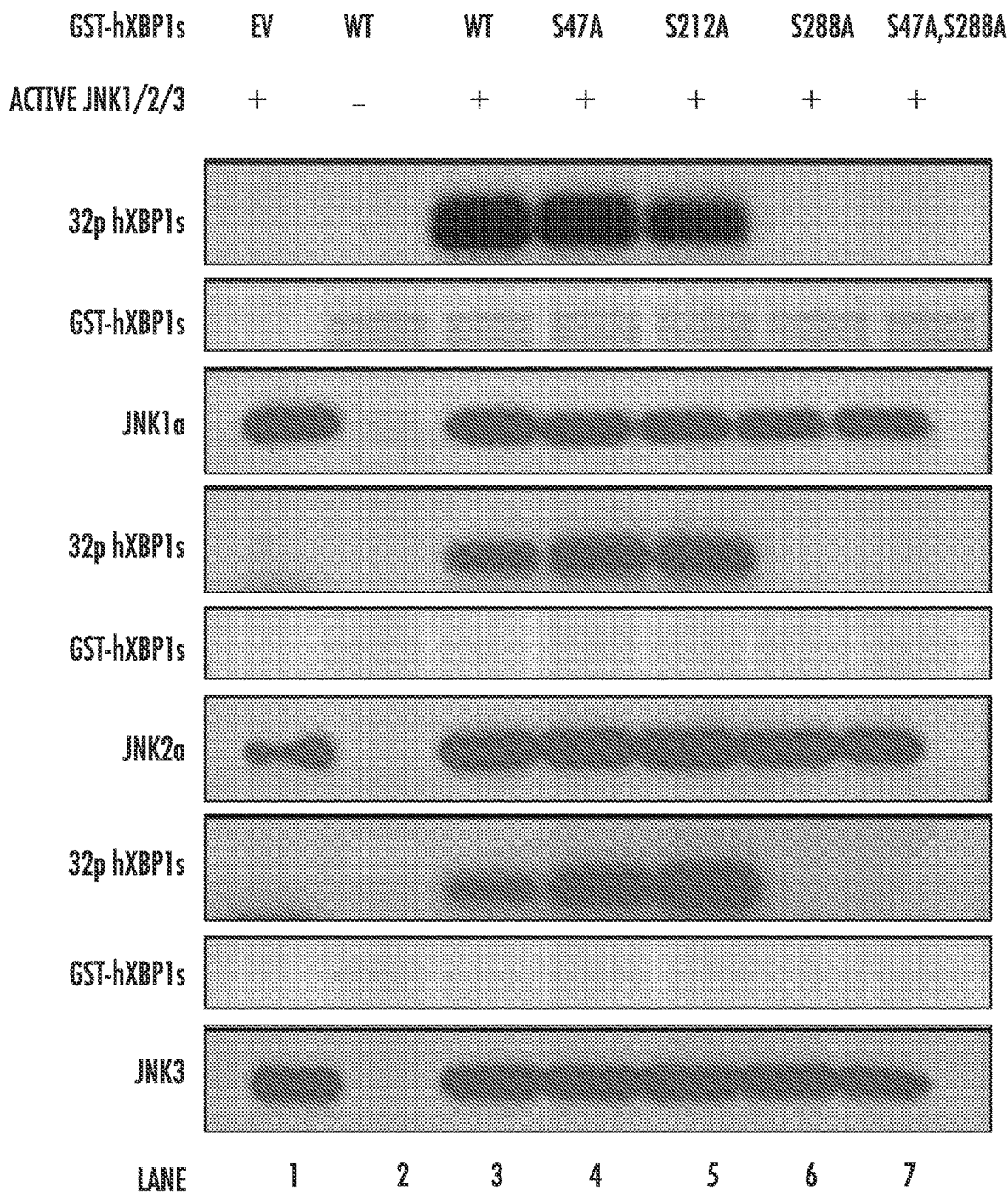
FIG. 3A: JNKs phosphorylated hXBP1s at S288 in an in vitro kinase assay. Affinity-purified GST-tagged hXBP1s wide-type (WT) or mutant was incubated with a mixture of three constitutively active recombinant JNKs in the presence of $^{32}P$. The reaction mixture was separated on SDS-PAGE and visualized by autoradiography. The purified GST-tagged hXBP1s proteins were visualized by Coomassie blue staining. Mutation of S288 to Ala caused phosphorylation loss, while mutation of other sites had no effect on JNK-dependent phosphorylation.

The SCF$^{\beta\text{-}TrCP}$ complex recognizes its substrates in a phosphorylation dependent manner (Fuchs et al., *Oncogene*, 23:2028-2036 (2004)). Having demonstrated that JNKs promote the physical interactions between hXBP1s and P-TrCP (FIG. 2F), it was next determined whether JNKs-induced phosphorylation of XBP is can increase its binding affinity to β-TrCP. To test this hypothesis, it was initially determined whether hXBP1s was a physiological and direct substrate of JNKs' phosphorylation. Western blot analysis showed that in the presence of MG132, overexpressed JNKs induced an upward shift of FLAG-hXBP1s in SDS-page gels (FIG. 2G), suggesting post-translational modification of hXBP1s, possibly its phosphorylation. To test this notion, in vitro kinase assays were performed by incubating affinity-purified GST-tagged wild type (WT) hXBP1s with or without MKK7-JNK1, JNK2 or JNK3 recombinant proteins in the presence of $^{32}$P. It was found that JNK1, JNK2 or JNK3 was sufficient to directly phosphorylate hXBP1s (FIG. 3A, lane 3), and this phosphorylation did not occur when there was only kinases or substrates in the system (FIG. 3A, lanes 1 and 2). These results demonstrated that hXBPs is a novel, direct phosphorylation substrate of JNKs.

Figure 11B:
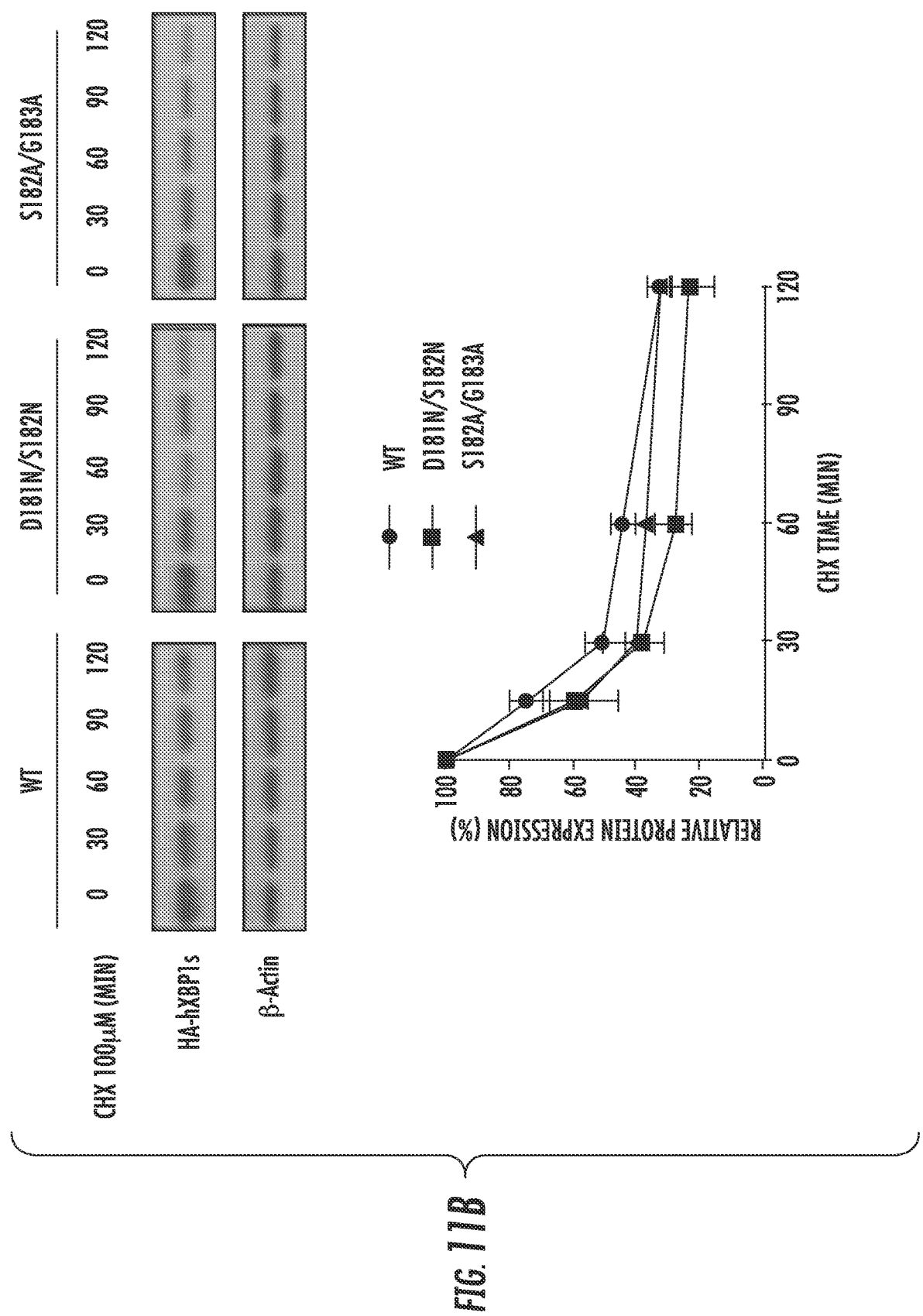
FIG. 11B: Mutations of the DSG-like motif at either D181, S182 and G183 failed to increase hXBP1s protein turnover. HEK293T cells were transfected with either hXBP1s-WT or mutants and then treated with CHX. Cells were lysed at various time points of CHX treatment for Western blotting analysis of HA-tagged hXBP1s expression. To facilitate observing degradation of WT and mutant hXBP1s proteins, Western blotting films with different exposure times were selected for data presentation for showing the similar basal levels of WT and mutant hXBP1s.
Figure 11C:
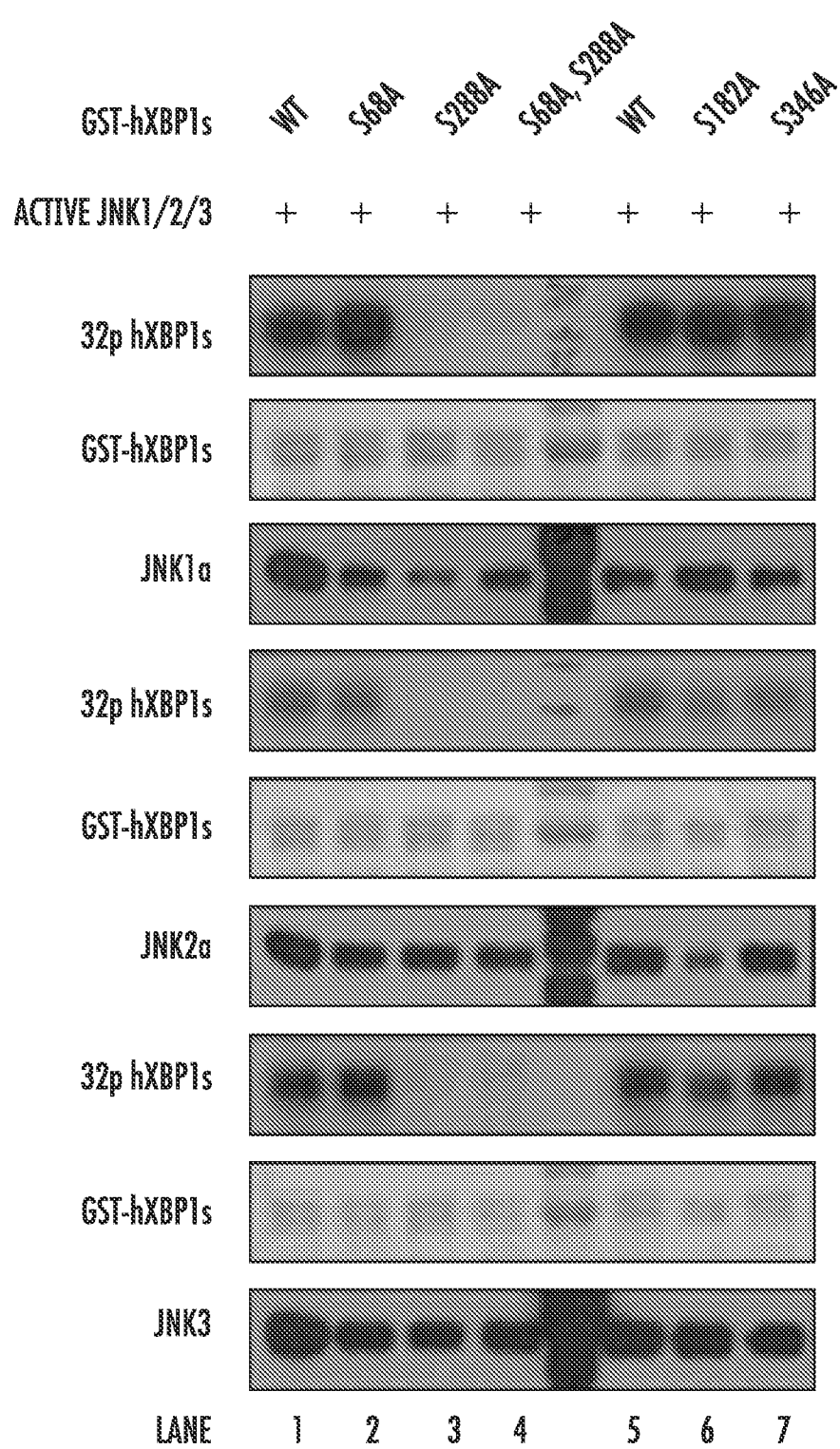
FIG. 11C: Phosphorylation sites S68 identified by MS as shown in FIG. 11D lower panel, the highly possible S/TP sites located outside PEST domain including S346P, and S182G in DSG-like motif, were not involved in hXBP1s phosphorylation by JNKs, as shown by in vitro kinase assays.

The JNK phosphorylation site(s) of hXBP1s were then determined. Previous studies showed that in addition to a DSG-like motif, a PEST sequence, a peptide sequence that is rich in proline (P), glutamic acid (E), serine (S), and threonine (T), also acts as the peptide for SCF$^{\beta\text{-}TrCP}$-mediated protein degradation (Inuzuka et al., *Cancer Cell*, 18:147-159 (2010)). Inspection of the amino acid sequence revealed that hXBP1s possesses both the DSG-like motif and two PEST sequences at amino acid position 210-245 and 282-293, respectively identified as P1 and P2 (FIG. 11A). JNKs target at either S or T residues following prolines (S/TP) for phosphorylation (Bogoyevitch et al., *Microbiol. Mol. Biol. Rev.*, 70:1061-1095 (2006)). Since JNKs regulate hXBP1s protein stability, it was hypothesized that the tentative JNKs' phosphorylation sites in hXBP1s are localized either within or in the close proximity to either the DSG-like motif or PEST sequences. Using the GPS 3.0 program, it was found that the DSG-like motif does not harbor a JNKs' phosphorylation consensus site. In supporting this notion, hXBP1s mutants that carry the point mutations within the DSG-like motif, e.g. D181N/S182N and S182A/G183A, displayed either no change or a decrease in protein stability, respectively (FIG. 11B). These results excluded the role of the DSG-like motif in mediating JNKs' action in promoting hXBP1s protein degradation. Instead, the GPS 3.0 program predicted that the S47, S68, S212, S288 and S346 matched with the reported JNKs' phosphorylation consensus sites (S/T/P). Among them, only Ser288 and its adjacent amino acid sequences match with the optimal phosphorylation sequence of JNKs, (Pro)-X-Ser/Thr-Pro [(P)—X—S/T-P] (see Bogoyevitch et al., supra). However, both Ser212 and Ser288 localize within the P1 and P2 PEST domains, respectively. To distinguish which of the amino acid(s) is/are direct phosphorylation site(s) of JNKs, either single or double mutants of hXBP1s were engineered which harbor serine (S) to alanine (A) mutations at these sites. In vitro kinase assay showed that mutation of Ser288 to A abolished JNKs-mediated phosphorylation of hXBP1s (FIG. 3A). In contrast, S to A mutation at all other potential JNK sites failed to block or reduce JNKs-mediated phosphorylation of hXBP1s in vitro (FIG. 3A and FIG. 11C). As an additional negative control, S to A mutation of S182, an amino acid that is not predicted to be a classic JNKs' phosphorylation site by the GPS 3.0 program but localizes in DSG-like motif (FIG. 11A), also failed to compromise JNKs-mediated phosphorylation of hXBP1s in vitro (FIG. 11C). Taken together, these results indicated that Ser288 is the only residue that mediates JNKs' direct phosphorylation of hXBP1s, and the P2 domain is the one that mediates JNKs' regulation of hXBP1s protein stability.

Figure 3B:
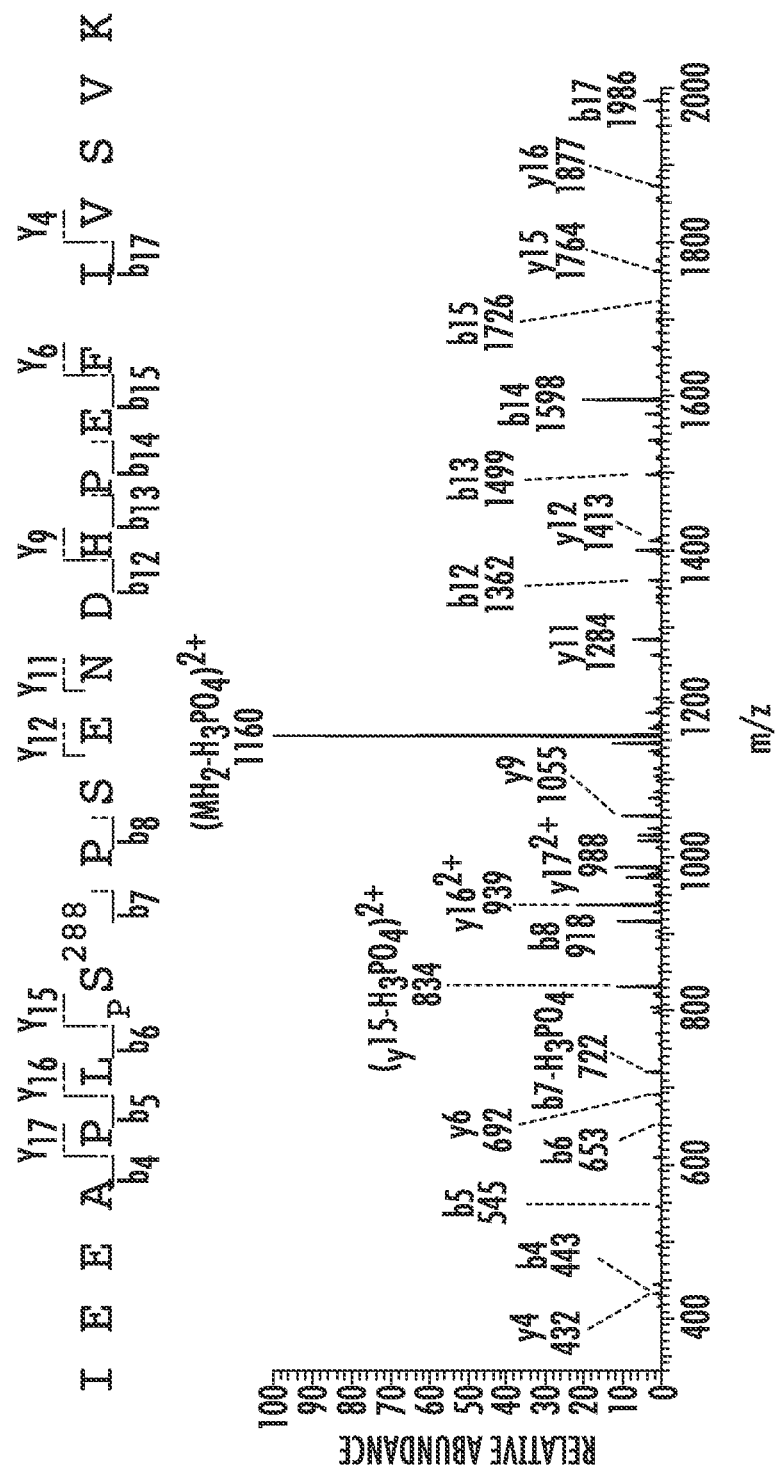
FIG. 3B: Representative tandem mass spectrum of hXBP1s-derived tryptic peptide demonstrating phosphorylation at S288. HA-hXBP1s was co-transfected with a mixture of MKK7-JNK1, 2 and 3 constructs into HEK293T cells. hXBP1s was then affinity-purified, in-gel digested with trypsin and subjected to LC-MS/MS analysis. Peaks matching expected singly- and doubly-charged (++) b- and y-ions are labelled.
Figure 11D:
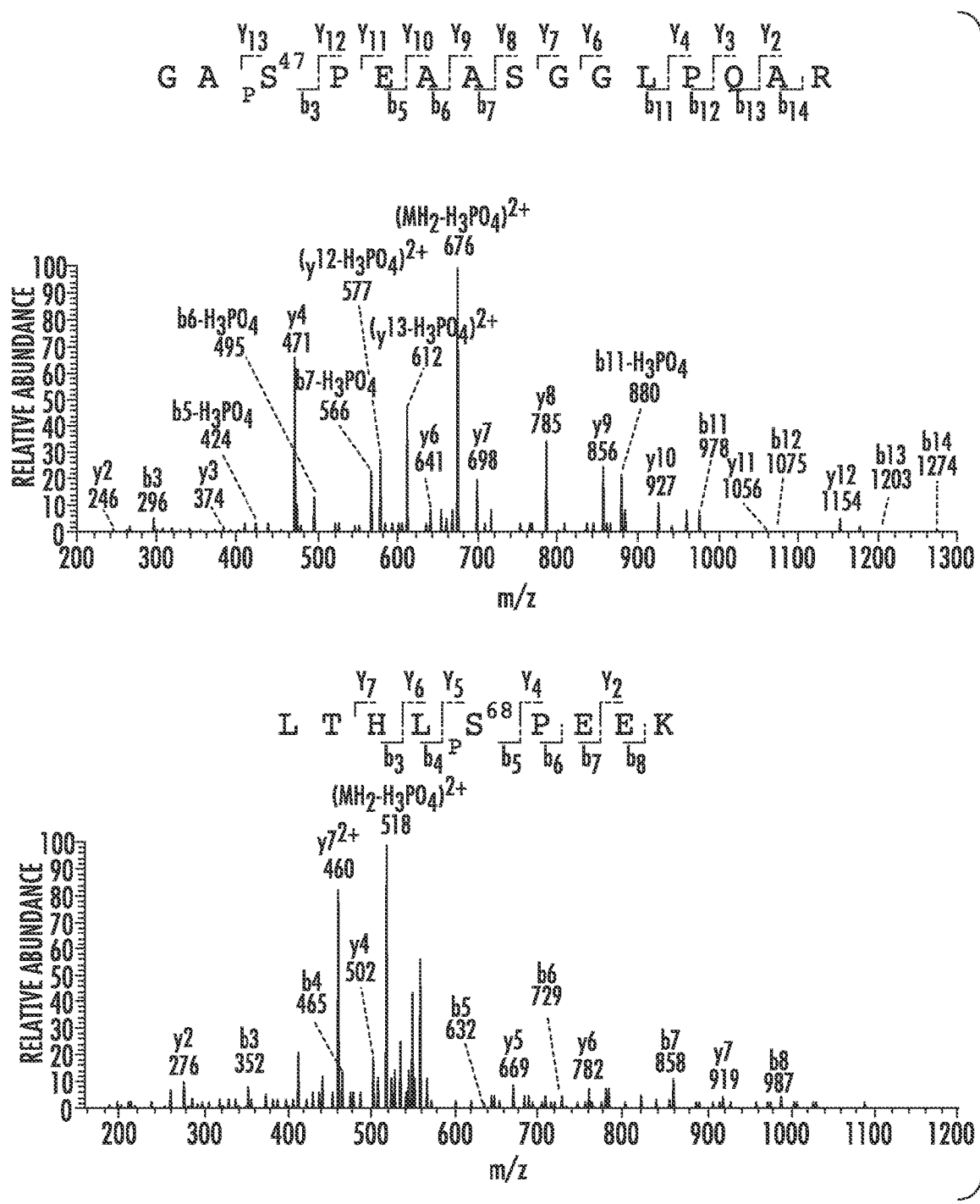
FIG. 11D: Tandem mass spectra of hXBP1s-derived tryptic peptides demonstrate the phosphorylation at S47 (left panel) and S68 (right panel) sites. These sites are S/TP sites, which are the classic consensus MAPK kinase-dependent phosphorylation sites. Results were produced in three independent experiments, each with three replicates. The scale bars from FIG. 11B indicate ±SD.

It was then determined whether hXBP1s is a physiological phosphorylation target of JNKs. For this purpose, tandem mass spectrometry (MS/MS) was employed. HEK293T cells were transfected with a HA-hXBP1s mixture of MKK7-JNK1, 2, and 3. The HA-tagged hXBP1s proteins were immunopurified in the presence of MG132, electrophoresed and visualized by Coomassie blue staining. The gel region containing hXBP1s was excised and digested with trypsin, and the resulting complex mixture of tryptic peptides was analyzed by nanoflow liquid chromatography tandem mass spectrometry (nLC-MS/MS). In total, 10 tryptic peptides with unique amino acid sequences covering 41% of the hXBP1s protein sequence were identified by MS, including three singly phosphorylated peptides containing Ser47. Ser68, and Ser288 (FIG. 3B and FIG. 11D). These results indicated that JNKs could phosphorylate hXBP1s at S47, S68 and S288 in vivo. Since S to A mutation at S47 or S68 did not affect JNKs-mediated phosphorylation in the in vitro (FIG. 3A, lane 4 and FIG. 11C, lane 2), it was concluded that JNKs cannot directly phosphorylate hXBP1s at S47 and S68 in vivo either. In contrast, JNKs-mediated phosphorylation at the S288 position was identified by both in vitro kinase assay (FIG. 3A, lane 6 and FIG. 11C, lane 3) and by MS analysis (FIG. 3B), underscoring the physiological significance of S288 in JNKs-mediated phosphorylation of hXBP1s in vivo.

Figure 3C:
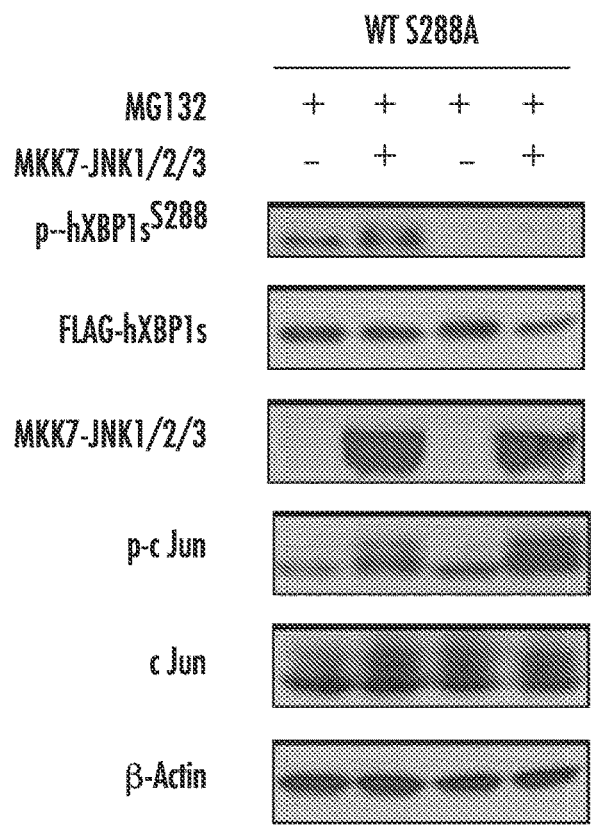
FIGS. 3C and 3D: Characterization of a novel hXBP1s$^{S288}$ phospho-specific antibody.
Figure 3D:
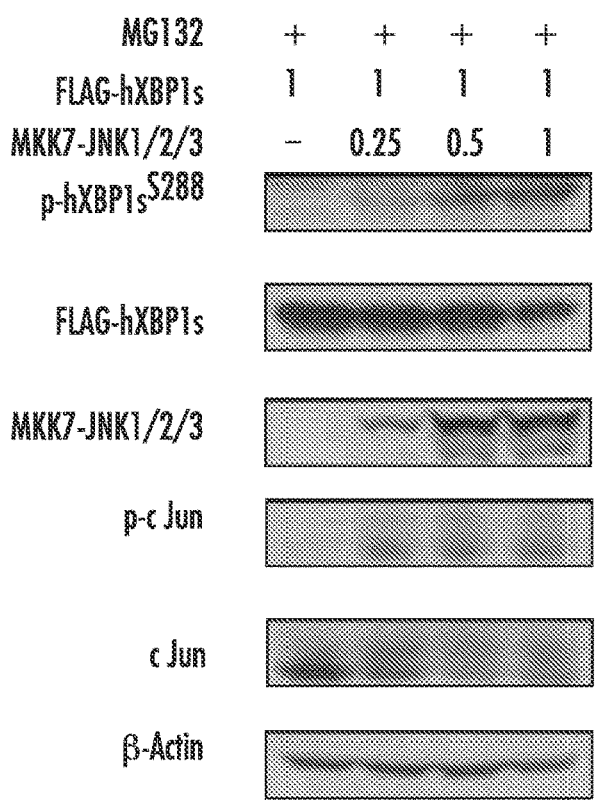

Finally, to better characterize the JNKs' phosphorylation at S288 in vivo, a custom-made antibody was developed that recognized phosphorylation at S288, p-hXBP1s$^{S288}$. Western blot analysis demonstrated that the antibody recognized JNKs-mediated phosphorylation of wild-type (WT) hXBP1s but not the mutant, which carries a S to A mutation at Ser288 (FIG. 3C), indicating the specificity of the p-hXBP1s$^{S288}$ antibody. In addition, the antibody recognized JNKs-dose dependent phosphorylation of hXBP1s (FIG. 3D), further indicating its specificity for the p-hXBP1s$^{S288}$. These results confirmed that Ser288 was phosphorylated by JNKs in vivo.

Figure 15B:
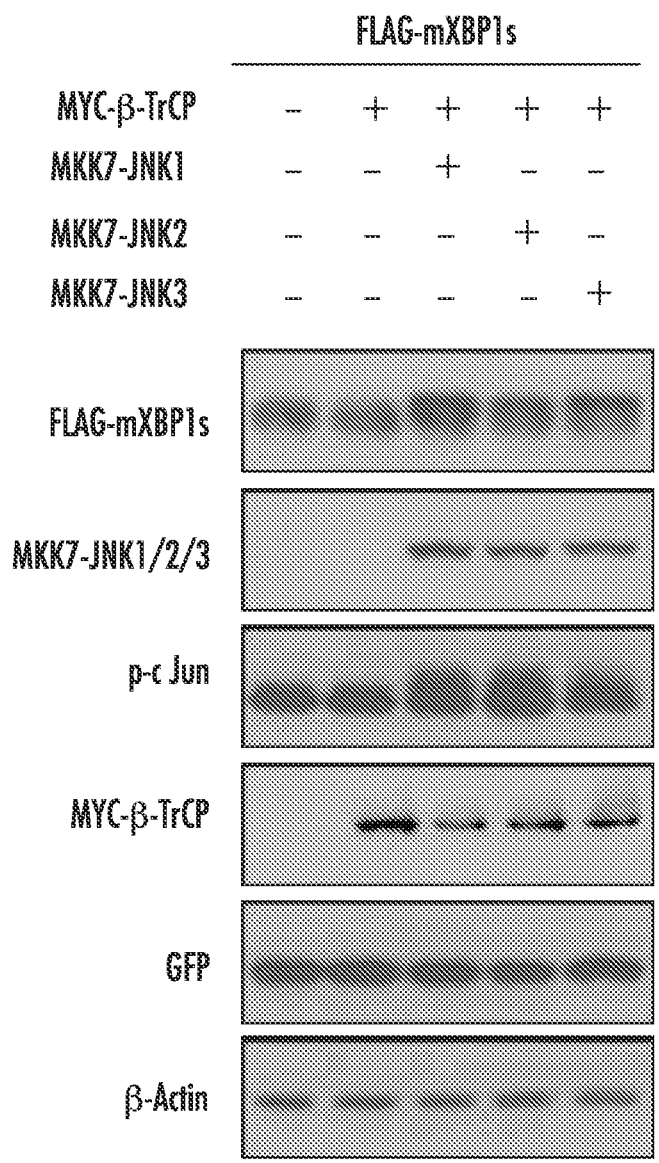
FIG. 15B: Over-expression of β-TrCP and constitutively active JNK1, 2, or 3 did not affect the expression of mXBP1s protein. HEK293 cells were co-transfected with mXBP1s, β-TrCP and MKK7-JNK1, 2, or 3. Expression of mXBP1s protein was determined by Western blotting. GFP served as a control for transfection efficiency.

Taken together, these findings demonstrate that hXBP1s is a novel, direct and physiological phosphorylation substrate of JNKs, and that S288 is the only amino acid that mediates JNKs' direct phosphorylation of hXBP1s. It is worth noting that the S288 residue is only present in hXBP1s and not in mXBP1s (FIG. 15A) nor in human unspliced XBP1 (hXBP1u) (data not shown). Thus, S288 was the focus of subsequent studies.

JNKs Phosphorylate hXBP1s on Ser288 to Trigger its Degradation.

Figure 4A:
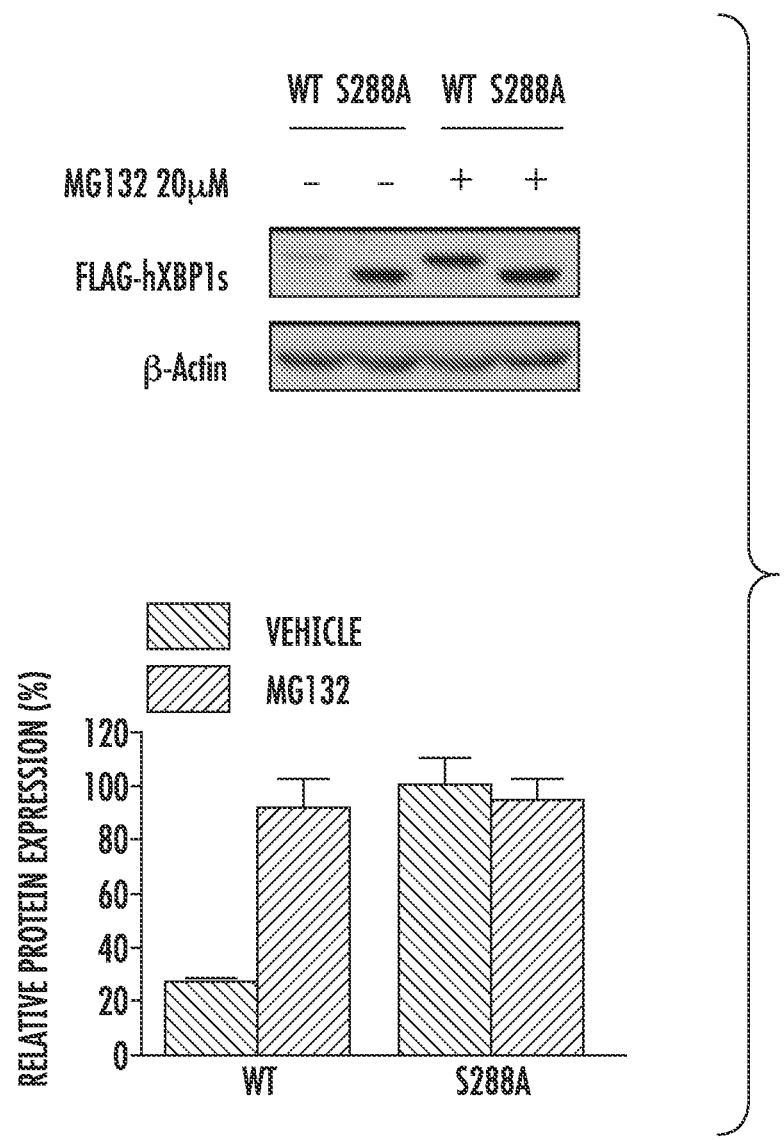
FIG. 4A: The phosphorylation-deficient mutant, hXBP1s S288A, shows a decreased molecular weight and increased steady-state protein expression as compared with WT counterpart in KM101 cells, and the latter difference was abolished by MG132 treatment. Human stromal line KM101 cells that stably overexpress hXBP1s WT or S288A mutant were treated with MG132 and lysed for Western blotting analysis.
Figure 4B:
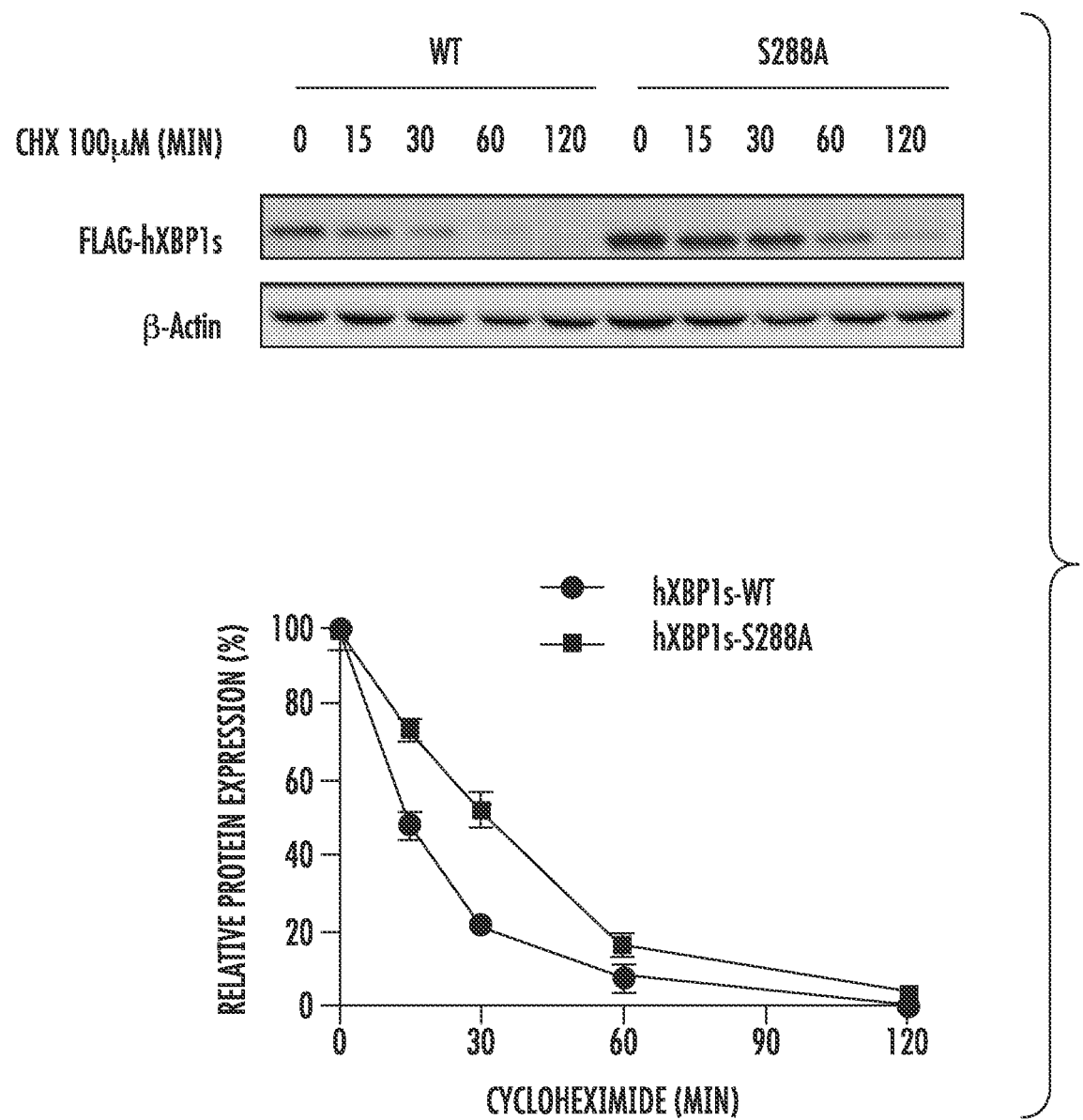
FIG. 4B: hXBP1s S288A mutant has a slower protein turnover rate than WT counterpart. hXBP1s-WT or -S288A overexpressing KM101 cells were treated with CHX and lysed for Western blotting analysis. The expression of either hXBP1s WT or S288A mutant protein at all the time points was quantified by band densitometry, normalized to loading control and presented as fold change over zero time point.
Figure 12A:
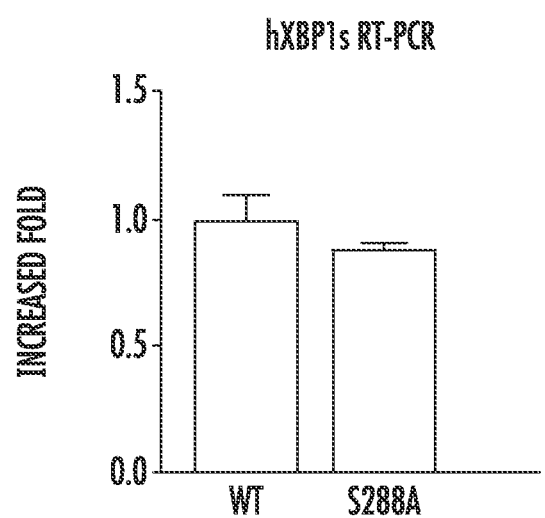
FIG. 12A: hXBP1s S288A mutant doesn't cause change of mRNA expression as compared with its WT counterpart.

Having demonstrated that JNKs phosphorylates hXBP1s protein to promote its degradation and that S288 is required for JNKs' phosphorylation of hXBP1s, it was determined whether JNKs phosphorylation of hXBP1s at Ser288 was required for JNKs-induced protein degradation of hXBP1s. A human BMSC line KM101 cells was engineered that stably overexpressed either the phosphorylation-deficient hXBP1s mutant S288A or its WT counterpart. Western blot analysis demonstrated that, compared with the WT control, the mutant protein displayed greater hXBP1s protein levels and molecular motility, due to the lack of JNKs-mediated phosphorylation (FIG. 4A), but no change on its mRNA expression (FIG. 12A). The discrepancy in protein expression of the mutant and WT hXBP1s was not caused by an increase in mRNA expression of the mutant (FIG. 12A) and was abolished by MG132 treatment (FIG. 4A). These results indicated the enhanced protein stability of the mutant protein was a driving force for the increased steady-state protein level of the mutant. Consistent with this notion. CHX chase assays demonstrated that the mutant hXBP1s protein had a half-life of 45 minutes, compared with 20 minutes for WT proteins (FIG. 4B). Taken together, these results demonstrated that the phosphorylation of hXBP1s at Ser288 plays an important role in regulating hXBP1s protein stability and consequently the steady-state levels of hXBP1s protein level. Consistent with Ser288 being specific to hXBP1s and not mXBP1s (FIG. 15A), overexpression of JNKs only affected the protein expression of hXBP1s but not that of mXBP1s (FIG. 15B), which is consistent with a previously report (Lee et al., *Nat. Med.*, 17:1251-1260 (2011)).

Figure 4C:
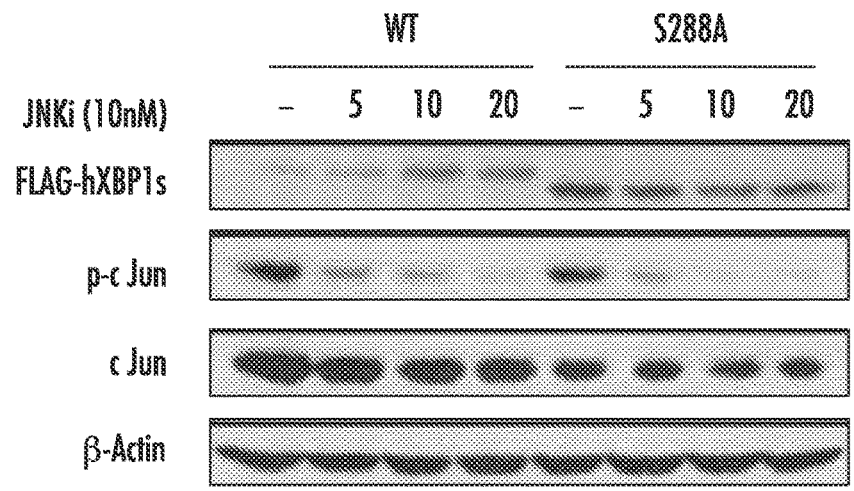
FIG. 4C: Mutating S288 to Ala blocked the dose-dependent increase of hXBP1s protein expression in response to JNKi treatment.
Figure 4D:
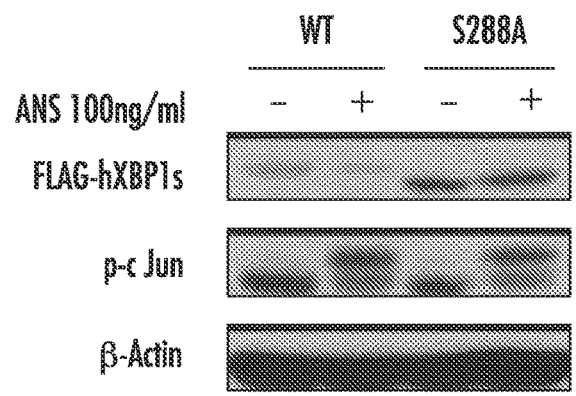
FIG. 4D: Mutating S288 to Ala prevented hXBP1s degradation by JNK, which was activated by ANS. The same cell lines as described in FIGS. 4A, 4B and 4C were used.
Figure 4E:
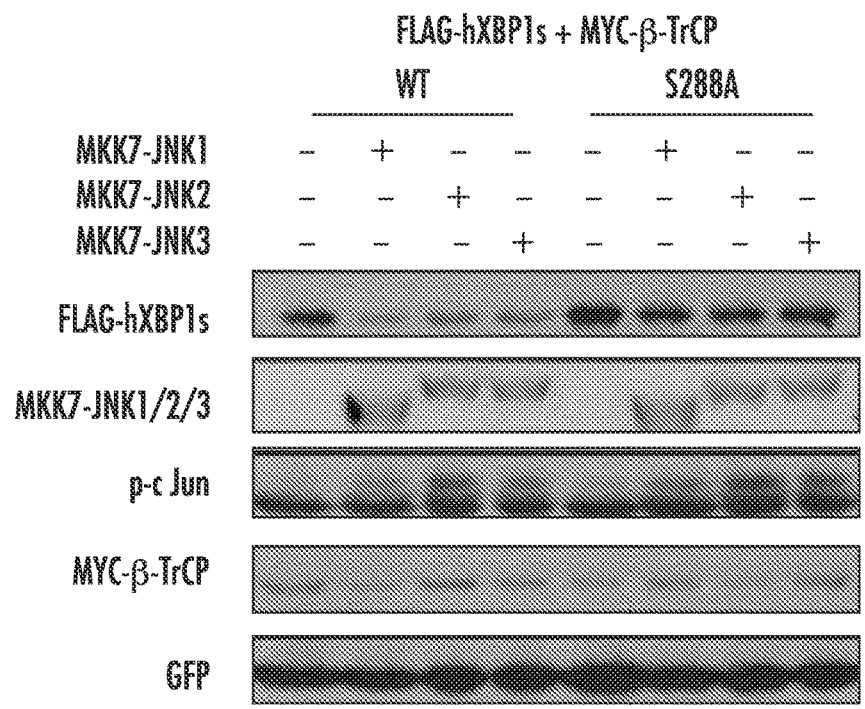
FIG. 4E: Mutating S288 to Ala prevented hXBP1s degradation by either MKK7-JNK1, or 2, or 3. HEK293T cells were co-transfected with either hXBP1s WT or S288A mutant, β-TrCP and any of MKK7-JNK1, 2 and 3. The transfected cells were lysed for Western blotting analysis. GFP served as a control for the transfection efficiency.
Figure 4F:
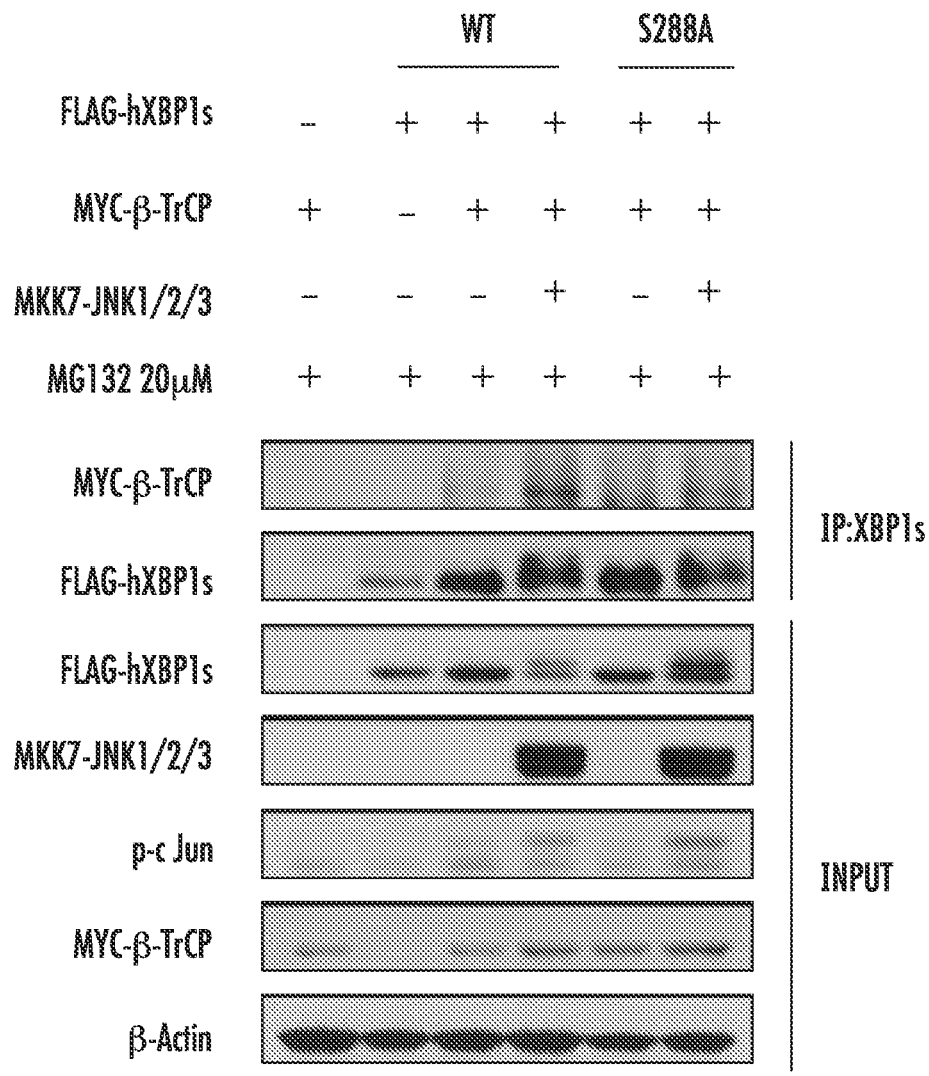
FIG. 4F: hXBP is S288A mutant showed less binding to β-TrCP1 than WT counterpart. HEK293T were co-transfected with either hXBP1s WT or S288A mutant, β-TrCP and a mixture of MKK7-JNKs. hXBP1s was then immunoprecipitated from transfected cells and analyzed by Western blotting.
Figure 12B:
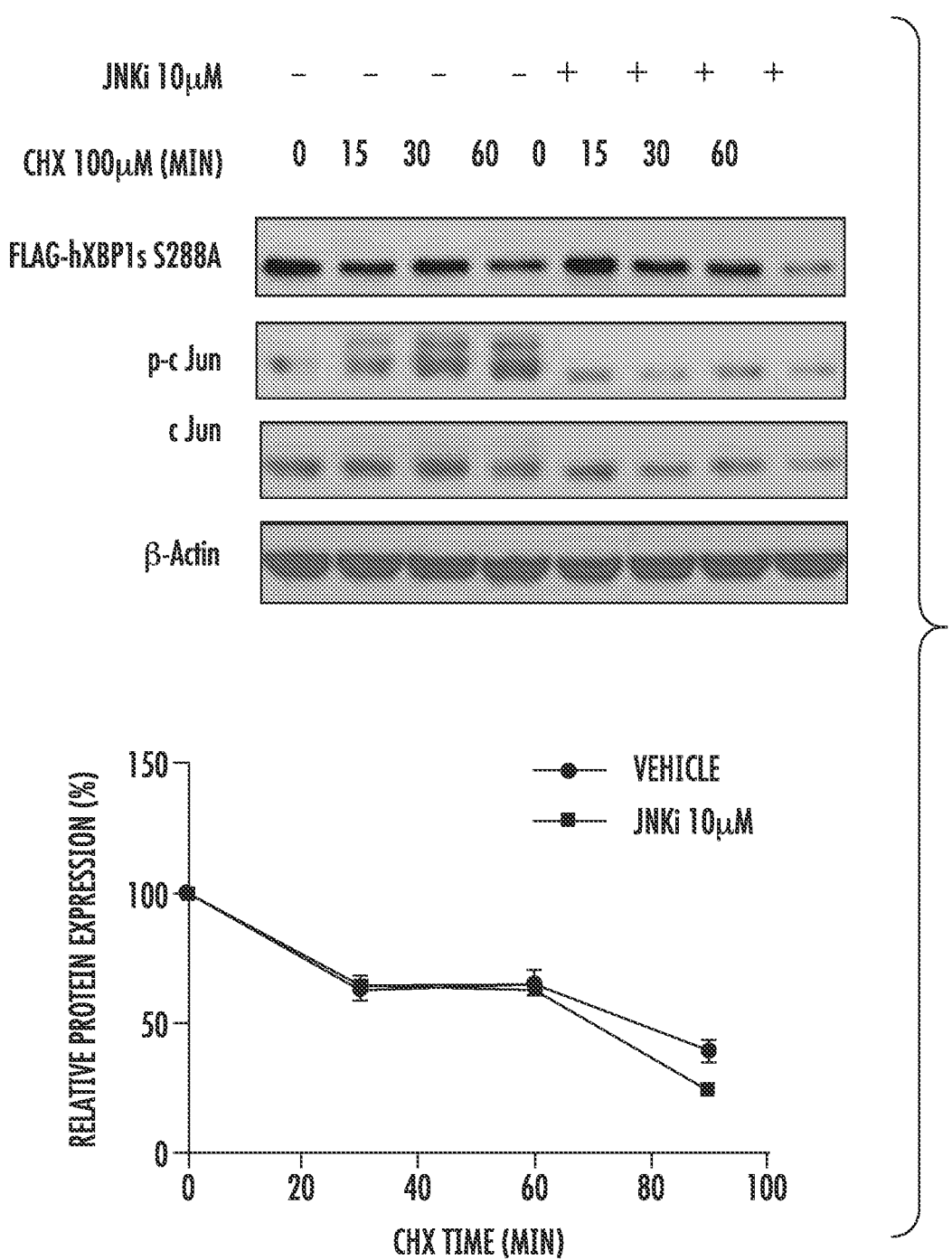
FIG. 12B: hXBP1s S288A mutant did not show slower protein turnover after JNK inhibition by JNKi. HEK293T cells transfected with hXBP1s S288A mutant were pre-treated with JNKi and then treated with CHX. Protein expression of hXBP1s S288A mutant at different time points were analyzed by Western blotting.
Figure 12C:
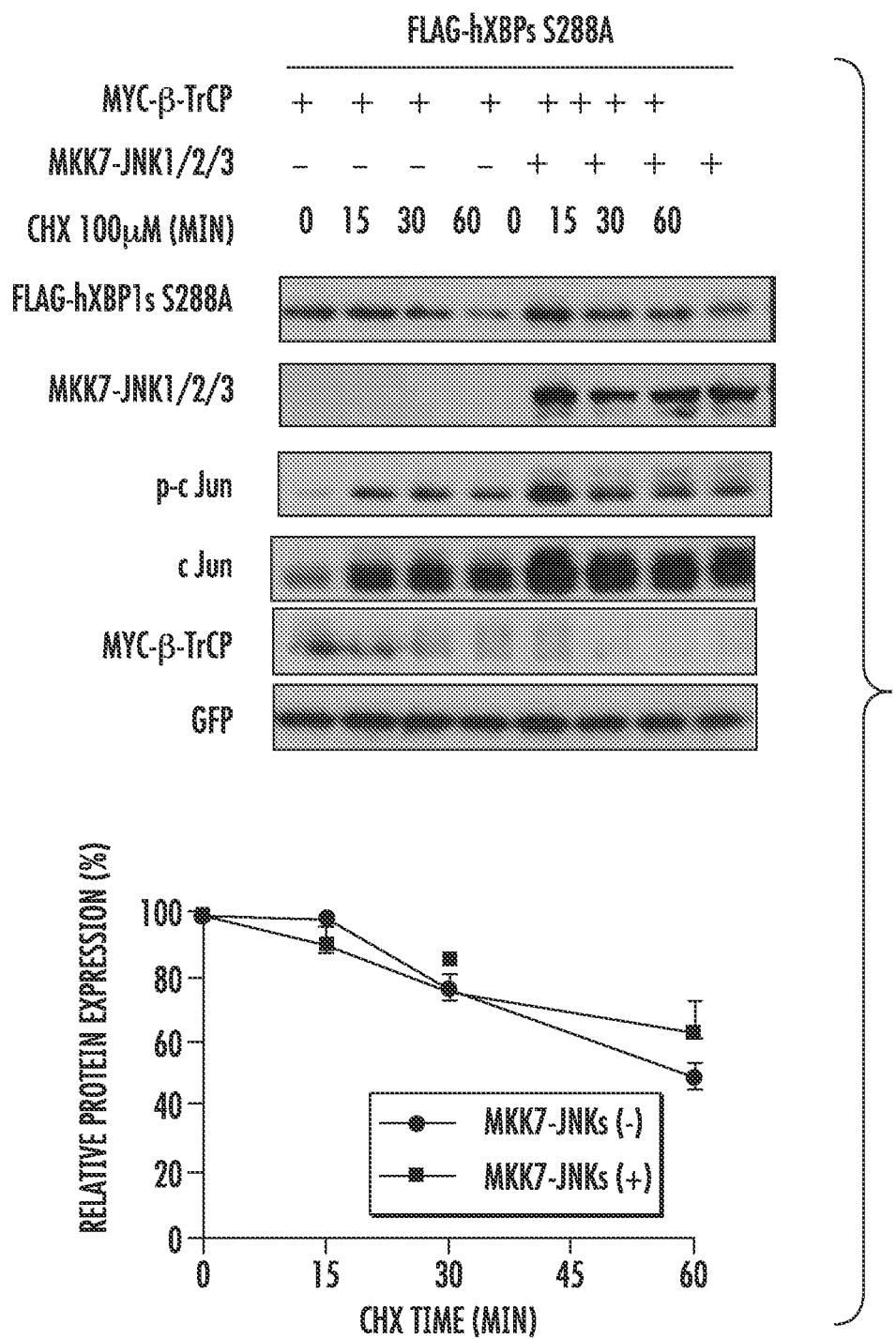
FIG. 12C: hXBP1s S288A mutant did not show faster protein turnover after JNK activation by fusion to MKK7. HEK293T cell were co-transfected with hXBPs S288A mutant, β-TrCP and a mixture of MKK7-JNKs. The transfected cells were then treated with CHX. The protein expression of hXBP1s S288A mutant at different time points were analyzed by Western blotting. GFP served as a control for the transfection efficiency.

Next, it was determined whether phosphorylation at Ser288 is required for JNKs' enhancement of the protein degradation of hXBP1s. Western blot analysis demonstrated that the JNKi dose-dependently increased the steady-state protein levels of overexpressed WT FLAG-hXBP1s, whereas the stimulatory effect was completely abolished in the S288A mutant expressing KM101 cells (FIG. 4C). In addition, pharmacological activation of JNKs by anisomycin greatly reduced the steady-state protein levels of WT FLAG-hXBP1s in KM101 cells, whereas it completely lost its inhibitory effect on the protein level of the S288A mutant (FIG. 4D). Moreover, it was found that S to A mutation at S288 largely prevented the inhibitory effect of overexpressed MKK7-JNK1, JNK2, or JNK3 on protein expression of FLAG-hXBP1s (FIG. 4E). These results demonstrated that three JNKs all act through the Ser288 site to regulate the steady-state protein level of FLAG-hXBP1s. Further, in contrast to the notion that either inhibition (FIG. 1E) or activation (FIG. 2H) of JNKs' activity destabilized or stabilized hXBP1s, respectively, the same changes in JNKs' activity failed to impact the protein stability of the S288A mutant (FIGS. 12B and 12C). These observations demonstrated that phosphorylation of Ser288 was required for JNKs' regulation of hXBP1s protein stability. Finally, co-immunoprecipitation analysis showed that MKK7-JNKs induced MYC-f-TrCP's binding with WT FLAG-hXBP1 but not with the mutant protein (FIG. 4F). This result demonstrated that JNKs phosphorylation of hXBP1s at Ser288 promotes hXBP1s' binding with β-TrCP and consequently its proteolysis.

Finally, it was determined whether phosphorylation at S288 played a role in regulating protein expression of endogenous hXBP1s. For this purpose, immunohistochemistry (IHC) staining was performed for total hXBP1s, p-hXBP1s$^{S288}$ and p-JNKs in thirty-six paraffin-embedded human bone marrow (hBM) specimens. The total hXBP1s commercial antibody was designed by the peptide sequence far away from the Ser288 site according to manufacturer's information, and the numbers on the axis refer to the scores of semi-quantification of IHC staining, described in Table 3 and the methods.

Figure 4G:
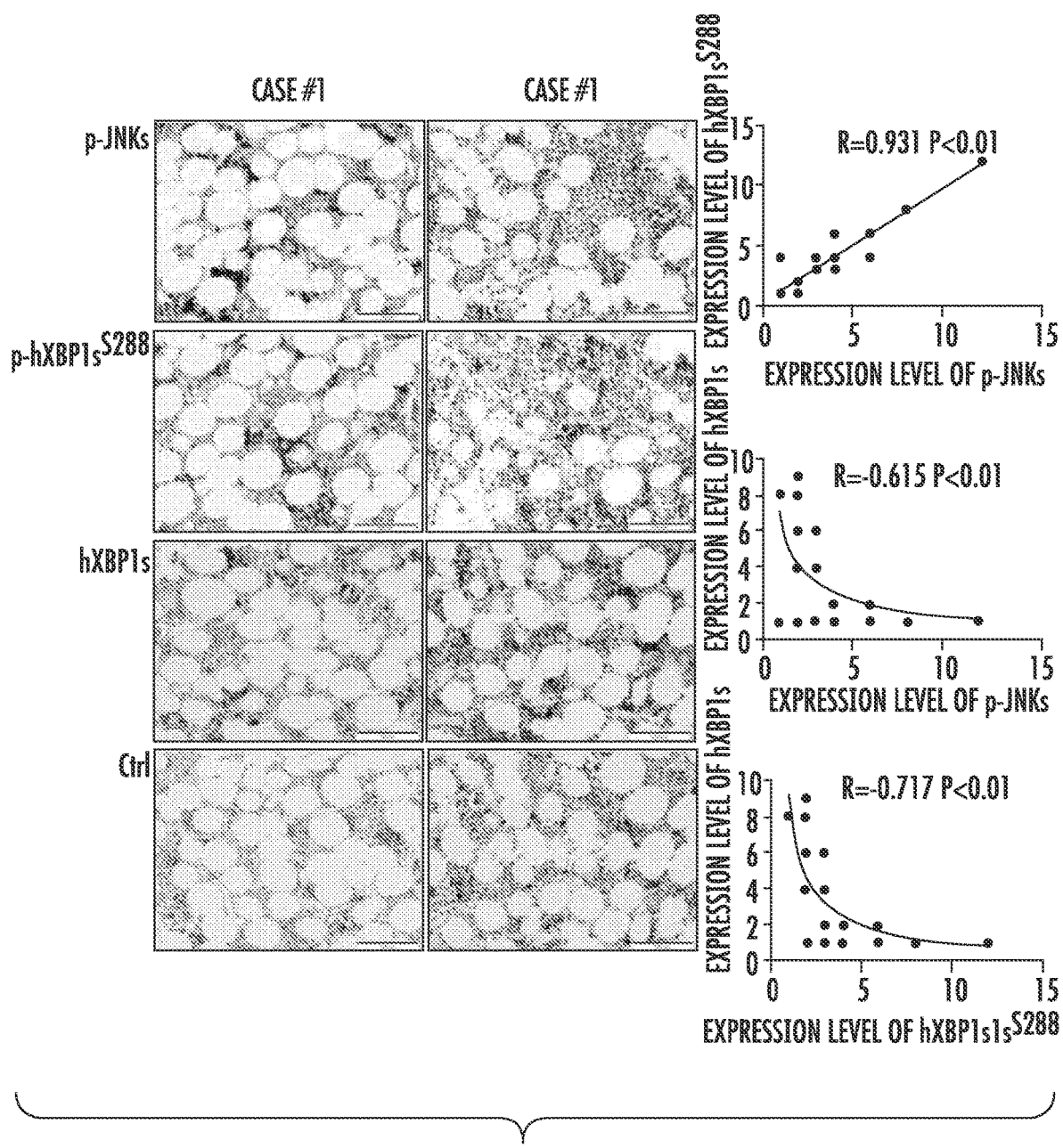
FIG. 4G: Immunohistochemistry (IHC) analysis of human bone marrow (BM) specimens for the expression of three proteins including total hXBP1s. p-hXBP1s$^{S288}$ and p-JNK. The representative two cases of images of IHC staining are shown in left panel. The IHC staining was scored (Table 3) and the correlation between any two of three proteins was analyzed by Spearman's rank correlation coefficient method (Table 2) and presented in the right panel. The expression of total hXBP1s reversely correlates with that of either p-JNK or p-hXBP1s$^{S288}$, while the expression of p-hXBP1s$^{S288}$ positively correlates with that of p-JNK. The results were produced in three independent experiments, each with three replicates. The scale bars from panel A and B indicate ±SD.

Representative images are shown in FIG. 4G. It was found that p-hXBP1s$^{S288}$ and p-JNKs were co-expressed in the specimens (FIG. 4G; Tables 2 and 3); and their expressions were significantly positively correlated with each other (r=0.931; p<0.01) (FIG. 4G, right upper panel). In contrast, the steady state protein level of the total hXBP1s is significantly reversely correlated with p-JNKs ($r^2$=-0.615:p<0.01) (FIG. 4G, right middle panel) and p-hXBP1s$^{S288}$ (r=-0.717; p<0.01) (FIG. 4G, right lower panel). Taken together, these observations highlighted the pathophysiological significance of JNKs-mediated phosphorylation in regulating protein level of endogenous hXBP1s in human bone marrow.

Figure 5A:
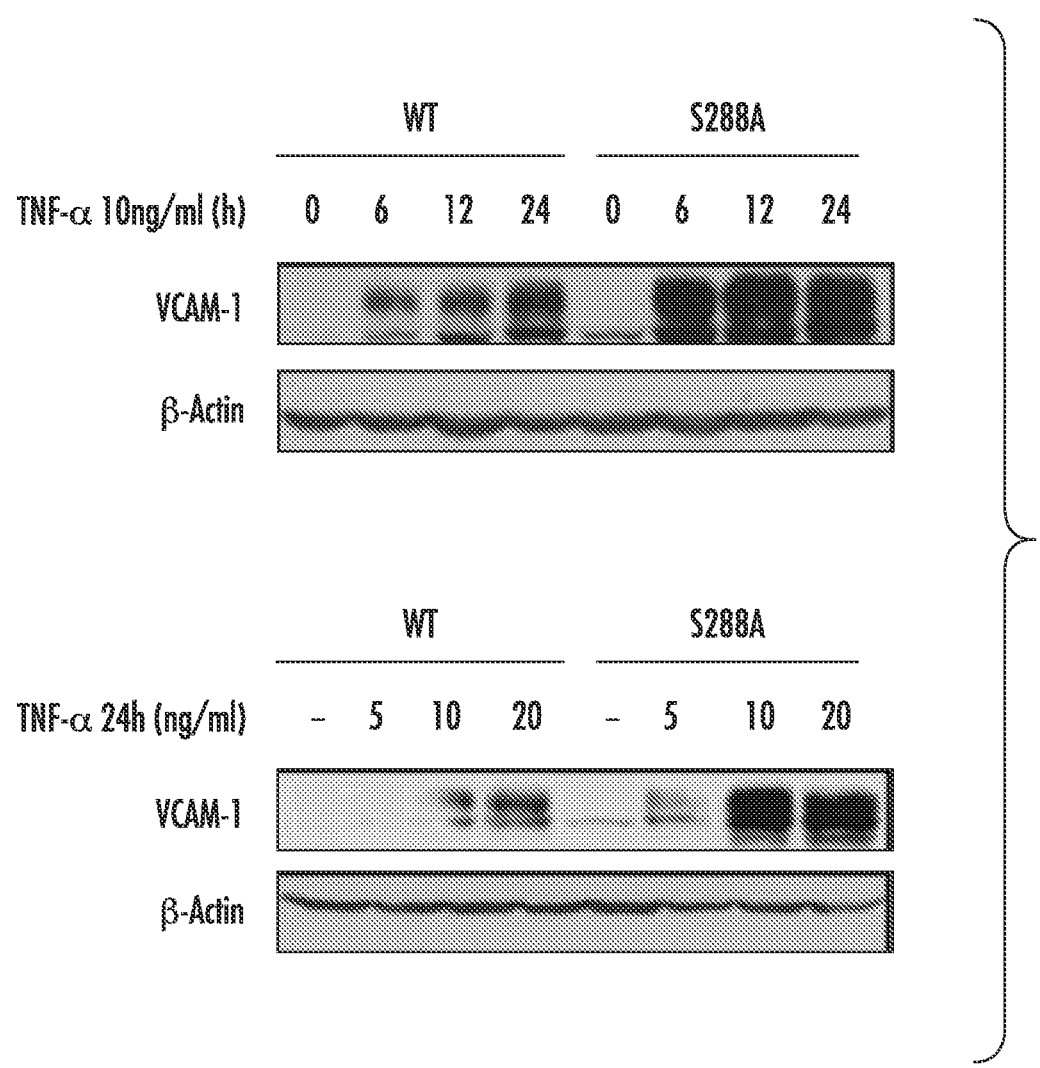
FIGS. 5A, 5B, and 5C: Compared with hXBP1s WT, overexpression of hXBP1s S288A mutant in BMSCs led to enhanced induction of VCAM-1 (FIG. 5A), IL-6 (FIG. 5B) and RANKL (FIG. 5C) by TNFα.
Figure 5B:
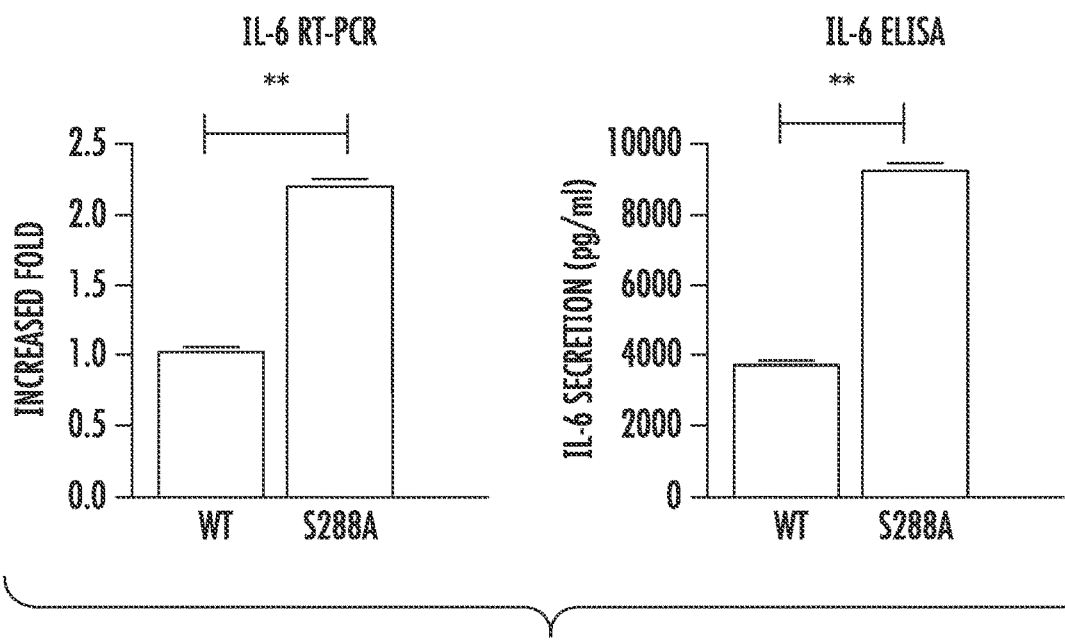
Figure 5C:
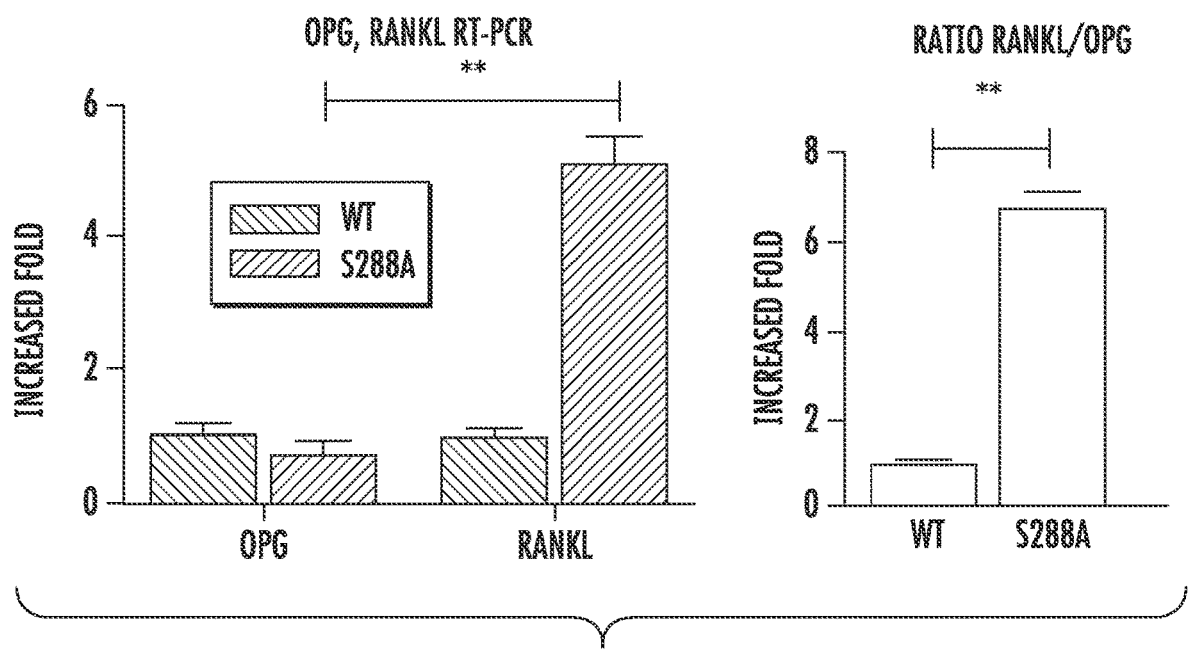

Deregulation of Ser288 phosphorylation of hXBP1s in BMSCs facilitated the stromal support of MM growth and osteoclastogenesis both in vitro and in vivo. hXBP1s expression in BMSCs is a potent pathogenic factor that promotes their support of MM growth and osteoclast (OCL) formation in MMBD. It does so via stimulating the gene expression of many inflammatory cytokines and cell adhesion molecules required for MM cell growth and osteoclast differentiation, such as VCAM-1, IL-6 and RANKL (Xu et al., *Blood*, 119:4205-4214 (2012)). Therefore, the pathophysiological role of phosphorylation at S288 of hXBP1s in regulating hXBP1s-mediated stromal support of MM cell growth and OCL formation was determined. VCAM-1 is a cell adhesion molecule highly expressed by BMSCs and required for MM cell adhesion to BMSCs and MM cell growth (Michigami et al., *Blood*, 96:1953-1960 (2000), Feuerbach et al., *FEBS Lett.*, 402:21-24 (1997)). Here, it was found that the S288A mutant was more efficient than WT hXBP1s in stimulating both basal and TNFα-induced protein expression of VCAM-1 in human BMSCs KM101 (FIG. 5A). Interleukin-6 (IL-6) is a key inflammatory cytokine required for osteoclast differentiation and growth and survival of MM cells (Xu et al., *Blood*, 92:241-251 (1998)). Similarly, compared with WT hXBP1s-overexpressing KM101 cells, the S288 mutant-overexpressing KM101 cells displayed an even significantly greater sensitivity to TNFα-induced gene expression of IL-6 (FIG. 5B, upper panel) and had significantly increased IL-6 protein levels in the conditioned medium (FIG. 5B, lower panel). RANKL is an ultimate regulator for osteoclastogenesis and highly expressed in BMSCs (Yasuda et al., *Proc. Natl. Acad. Sci.* 95:3597-3602 (1998)). The ratio of RANKL to osteoprotegerin (OPG), an important inhibitor of osteoclastogenesis, is a critical indicator of BMSC capacity to support osteoclastgenesis and predicts MM patient 5-yr survival rate (Terpos et al., *Blood*, 102:1064-1069 (2003)). Again, compared with WT hXBP1s-overexpressing KM101 cells, the mutant-overexpressing KM101 cells had a significantly greater gene expression of RANKL in the presence of TNFα (FIG. 5C upper panel). By contrast, the two cell types had comparable gene expression of the osteoprotegerin (OPG) under the identical experimental conditions (FIG. 5C lower panel), resulting in a 6.7-fold increase in RANKL/OPG ratio in the mutant-overexpressing KM101 cells, compared with WT-overexpressing counterparts.

Figure 5D:
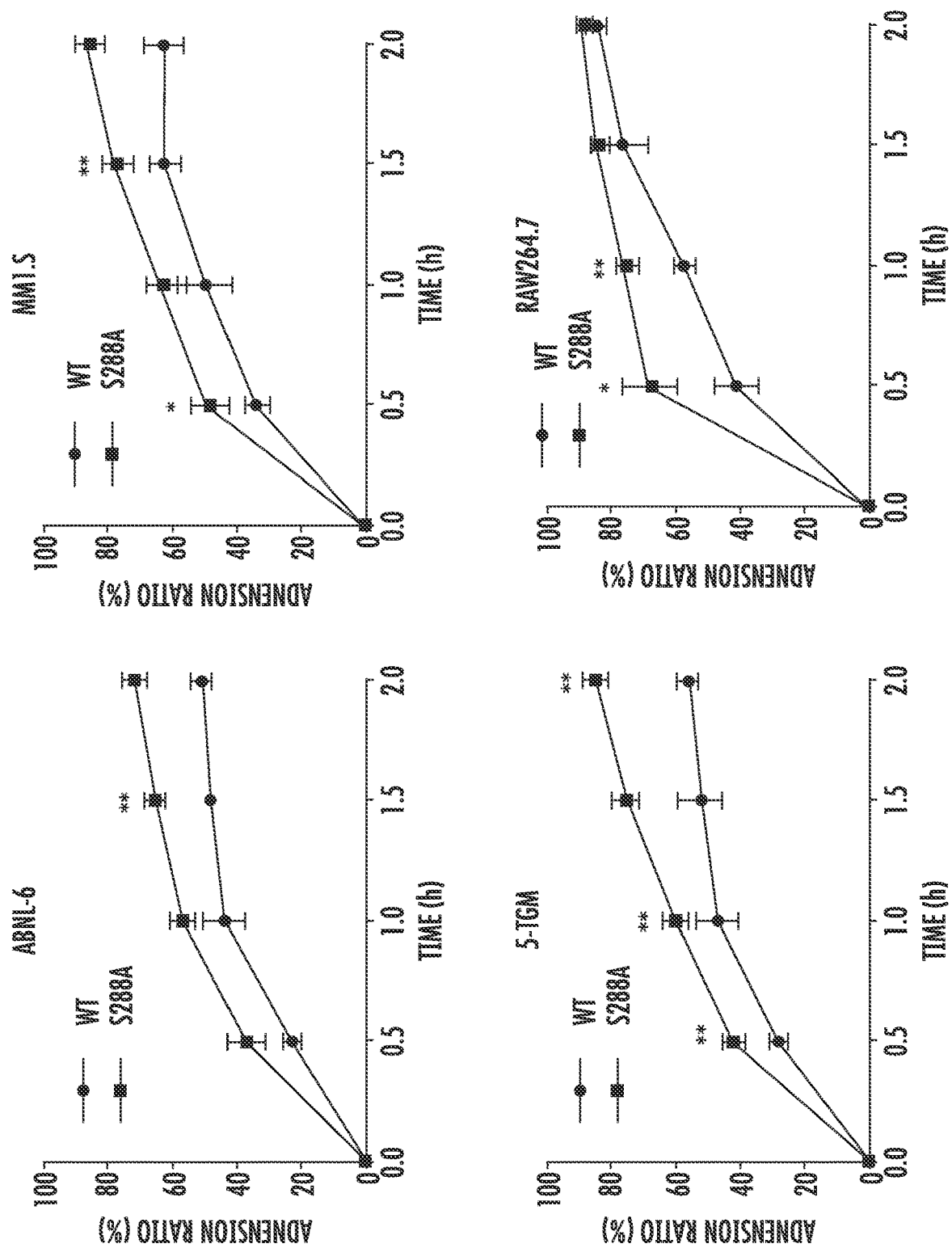
FIGS. 5D, 5E, and 5F: Compared with hXBP1s WT-overexpressing KM101 cells, the S288A mutant-expressing cells showed greater capacity to support MM and osteoclast adhesion (FIG. 5D), MM growth (FIG. 5E) as well as osteoclast (OCL) formation (FIG. 5F). The cell lines used include human multiple myeloma cells ABNL-6, MM.1s, mouse multiple myeloma cell 5-TGM and mouse macrophage cell RAW264.7.
Figure 5E:
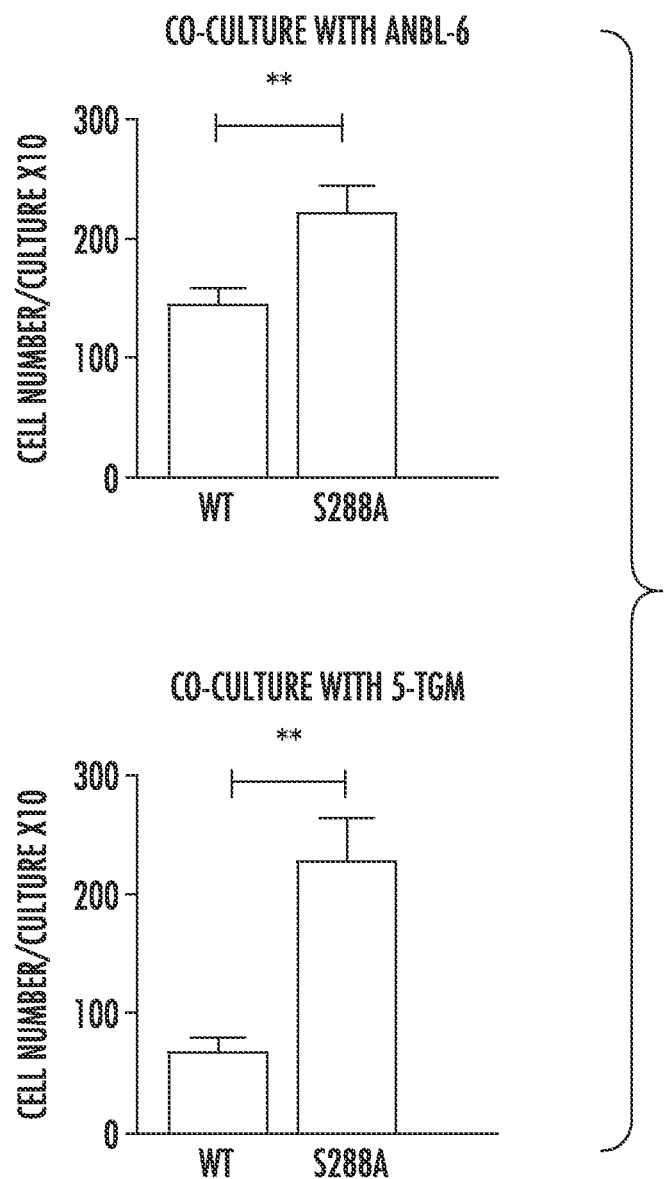
Figure 5F:
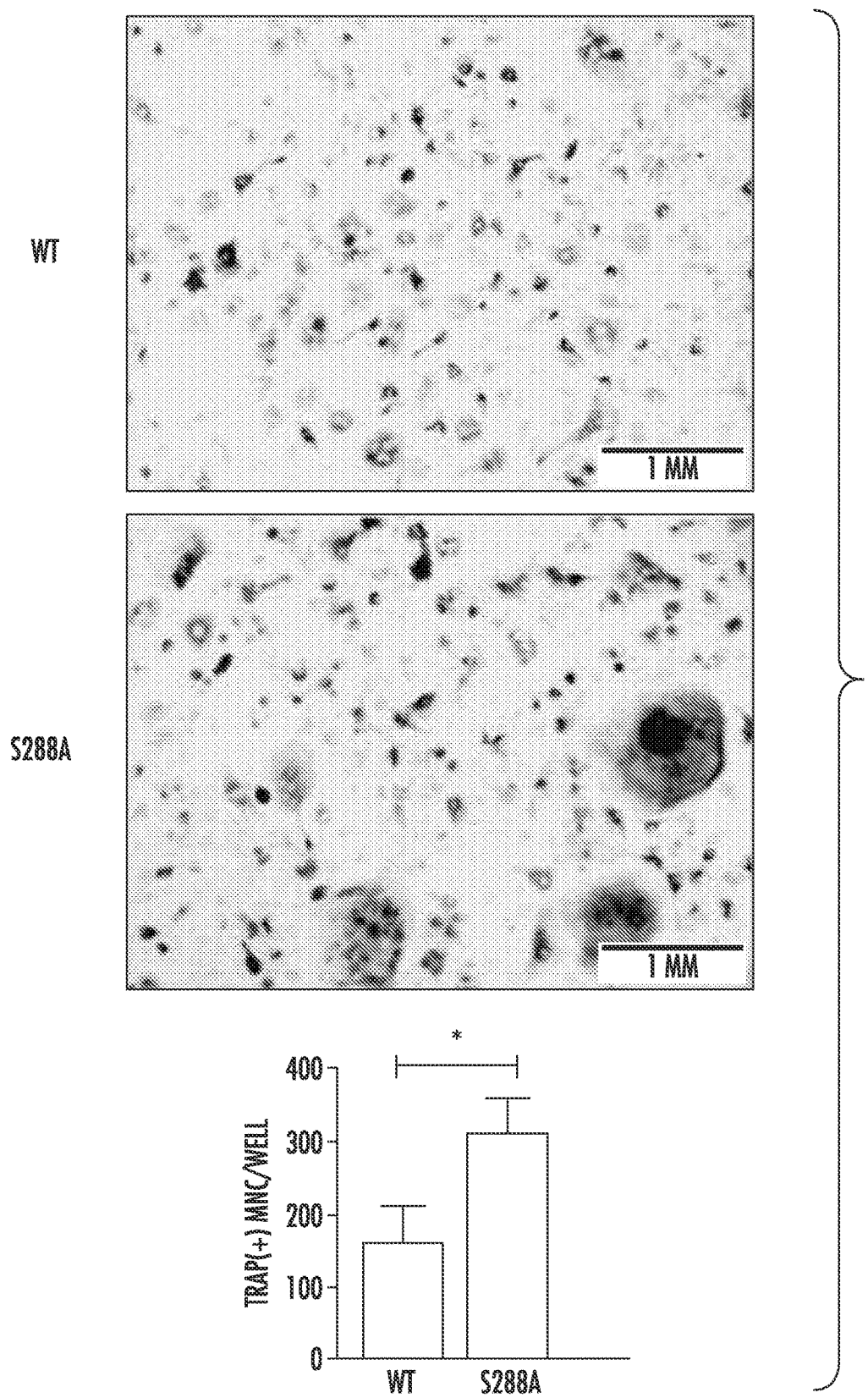

Consistent with these observations and the essential roles of VCAM-1, IL-6 and RANKL in tumor cells' adhesion, growth, and osteoclast differentiation, it was further found that compared with the WT hXBP1s-overexpressing KM101 cells, the S288A mutant-expressing KM101 cells were more efficient in supporting MM and osteoclast adhesion (FIG. 5D), MM growth (FIG. 5E) and OCL formation (FIG. 5F), as shown by cell-adhesion, growth and OCL formation assays, respectively. Taken together, these results demonstrate Ser288-mediated phosphorylation of hXBP1s decreases the stromal inflammatory signature and capacity to support MM cells growth and OCL formation in vitro.

Figure 6A:
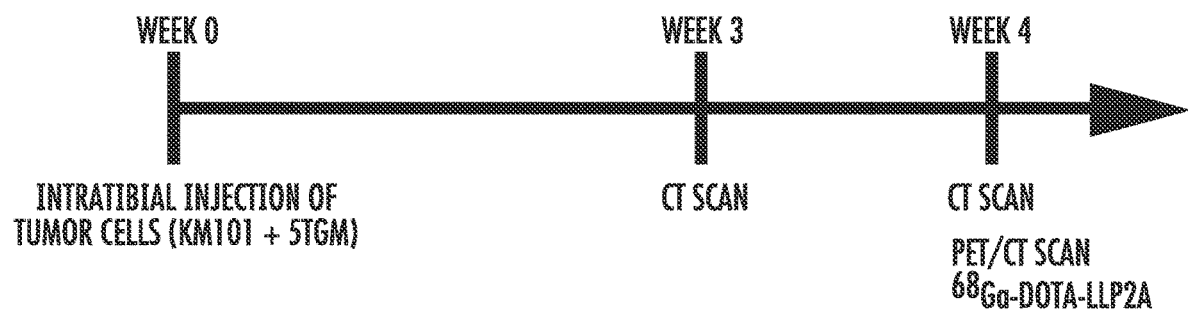
FIG. 6A: Schematic diagram of experimental design. MM line 5TGM cells were mixed with hXBP1 WT or S288A-overexpressing KM101 cells and then intratibially injected into left legs of mice. $^{68}$Ga-DOTA-PEG$_4$-LLP2A probe, a high affinity conjugate for VLA that is highly expressed on cell surface of 5TGM, was used for PET/CT imaging at 4 weeks post-injection.
Figure 6B:
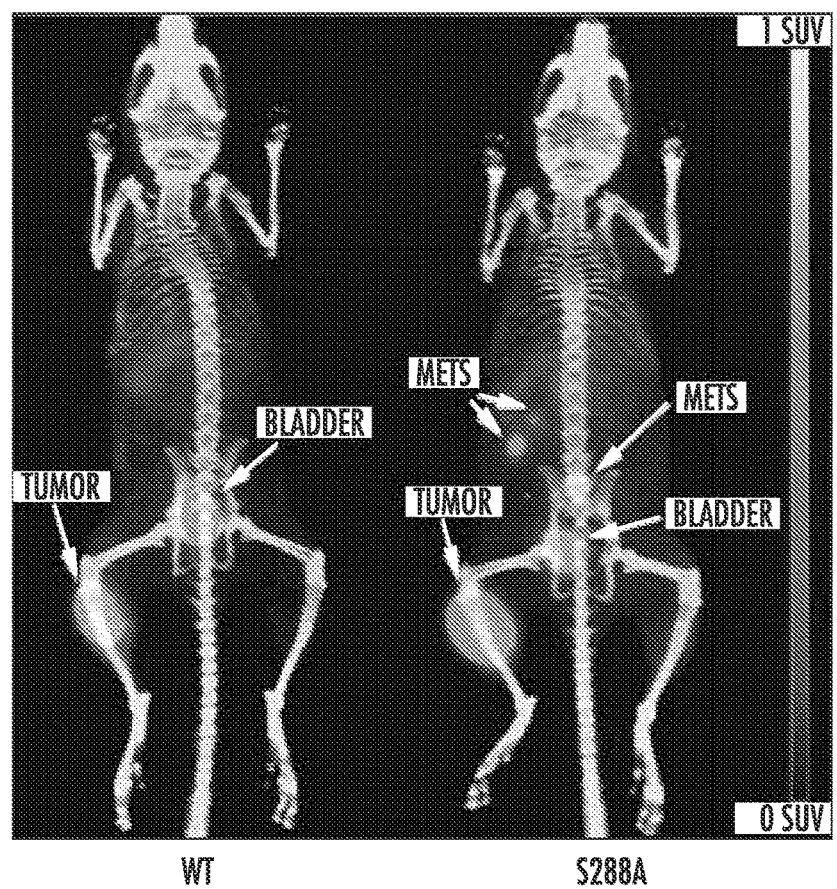
FIG. 6B: Representative images from PET/CT scanning of mice showing tumor formation at both the site of intra-tibial injection and metastatic sites. Greater tumor mass at injection sites and greater total number of tumor masses formed in hXPB1s S288A-carring mice than hXBP1 WT-carrying mice.
Figure 6C:
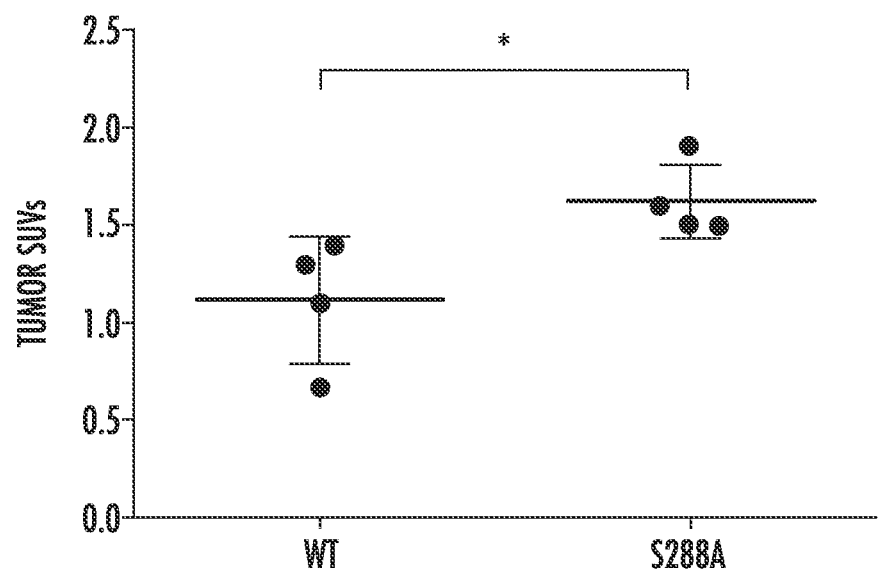
FIG. 6C: 3D image quantification SUV (standard uptake value) in mice. SUV values reflect the accumulation of $^{68}$Ga-LLP2A probe in tibia and are indicative of VLA-4 expression. The hXBP1s S288A group of mice showed higher SUV than the WT group.
Figure 6D:
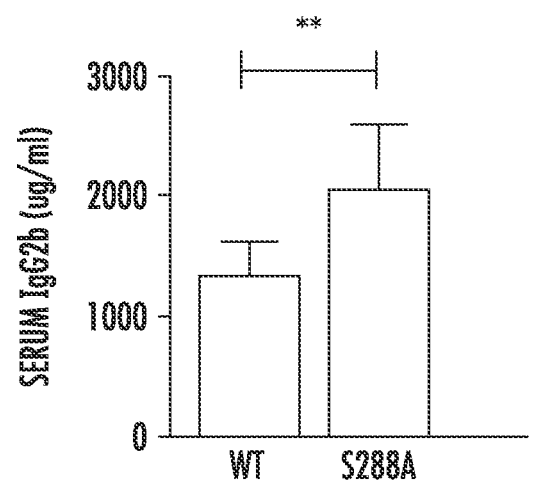
FIG. 6D: ELISA analysis of serum IgG2b, protein marker secreted by MM cells. The hXBP1s S288A group of mice showed increased level of serum IgG2b than the WT group.
Figure 13:
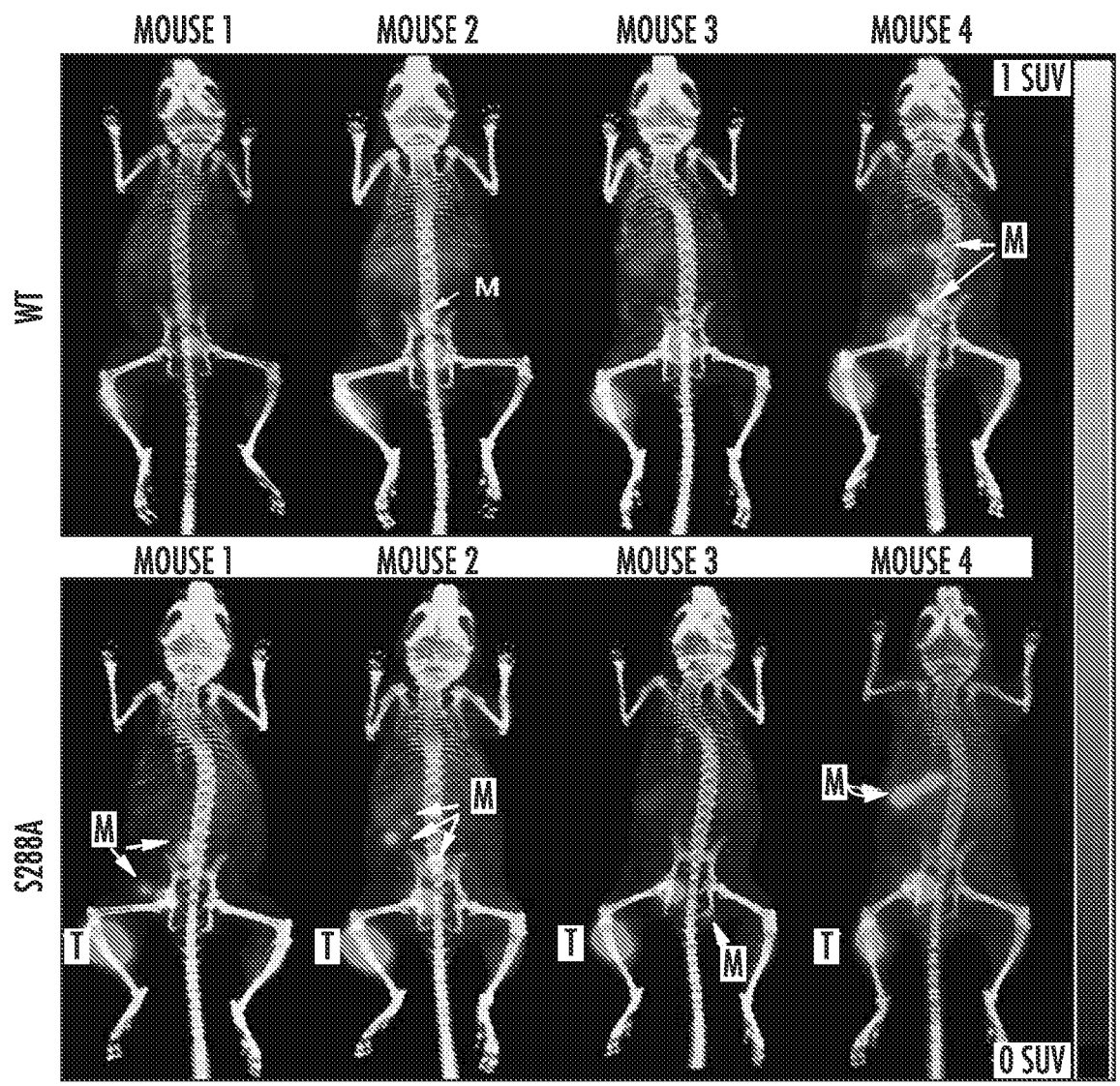
FIG. 13 shows deregulation of phosphorylation of hXBP1 on Ser288 in BMSCs facilitates its support of MM growth and metastasis. PET/CT imaging of mice using $^{68}$Ga-DOTA-PEG4-LLP2A. MM line 5TGM cells were mixed with hXBP1 WT (upper panel) or S288A (lower panel)-overexpressing KM101 cells and then intratibially injected into left legs of mice. The tumor growth was assessed using PEC/CT imaging. In the images, M refers to a metastasized tumor mass and T refers to the initial tumor injection site in the tibia.

The pathophysiological significance of Ser288-mediated hXBP1s phosphorylation in bone marrow stromal support of myeloma cell growth and osteoclastogenesis in vivo was next investigated. For this purpose, the co-cultured murine multiple myeloma line 5TGM1 cells and KM101 cells stably expressing either the WT or S288A mutant hXBP1s were intratibially injected into NIH III female mice. Tumor growth was assessed using Positron Emission Tomography—Computed Tomography (PET/CT) imaging 4 weeks post tumor cells injection (FIG. 6A). Since 5-TGM1 cells highly express VLA-4 (very late antigen 4, also called integrin α4β1), a trans-membrane non-covalent heterodimer and a cell surface marker for multiple myeloma (Miyake et al., *J. Cell. Biol.*, 119:653-662 (1992)), $^{68}$Ga-DOTA-PEG$_4$-LLP2A was used, a high affinity conjugate for VLA-4 successfully used for PET imaging of VLA-4 expression in melanoma, to visualize 5TGM1 cell growth with high specificity and sensitivity (Beaino et al., *Mol. Pharm.* 12:1929-1938 (2015)). Another LLP2A-based imaging agent, $^{64}$Cu-CB-TE1A1P-PEG$_4$-LLP2A, has very high uptake in 5TGM1 MM cells in KaLwRij mice in vivo (Soodgupta et al., *PLoS One*, 8:e55841 (2013); Soodgupta et al., *J. Nucl. Med.*, 57:640-645 (2016)). For this study, the more recently developed Ga-68 tracer was chosen, which given the short radionuclide half-life (68 min) has significant potential for translation to humans with MM. As shown by PET/CT imaging, the hXBP1s S288A-carrying mice experienced greater tumor burden at the local injection sites as well as a greater total number of tumor masses formed in vivo compared with the WT hXBP1s-carrying counterparts (FIG. 6B and FIG. 13A). In addition, the hXBP1s S288A-expressing group had a greater number of MM metastasis in distal organs, such as proximal femur heads, pelvis, lymph nodes and liver, than the wide-type control (FIG. 6B and FIG. 13A). Further, 3D imaging quantification revealed that the S288A group had higher uptake of the LLP2A tracer in the tumors, as reflected by a significantly higher standard uptake values (SUVs) compared with the WT group (FIG. 6C). Consistent with the macroscopic visualization of a greater tumor burden in the S288A group, this group of mice also had significantly increased levels of serum IgG2b (FIG. 6D), a monoclonal protein marker secreted 5TGM1 by MM cells (Garrett et al., *Bone*, 20:515-520 (1997)) compared with the counterparts. These data are consistent with data from another study showing that increased IgG2b levels correlated with higher SUV of $^{64}$Cu-CB-TE1A1P-PEG$_4$-LLP2A in 5TGM1 MM-bearing mice (Soodgupta et al., *J. Nucl. Med.*, 57:640-645 (2016)).

Figure 6E:
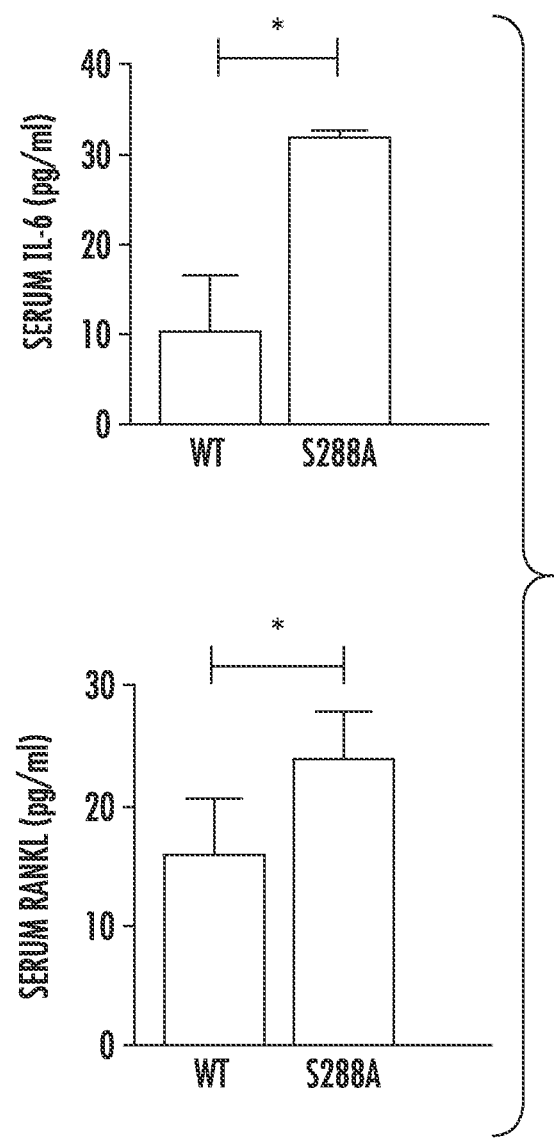
FIG. 6E: ELISA analysis of serum IL-6 and RANKL, two osteoclastogenic inflammatory cytokines. The hXBP1s S288A group of mice showed increased level of serum IL-6 and RANKL than the WT group.
Figure 6F:
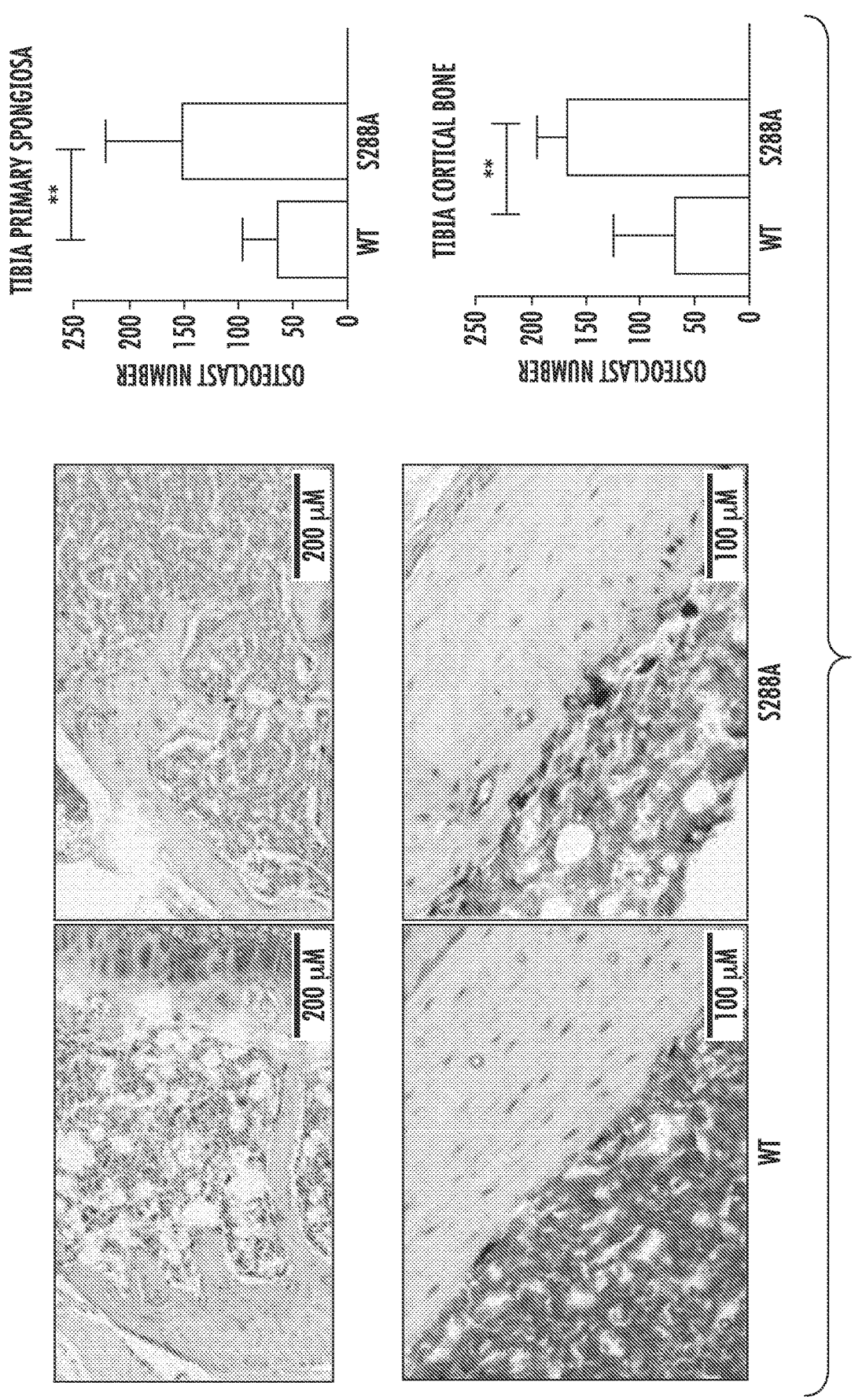
FIG. 6F: TRAP staining for osteoclast formation on the longitudinal sections of primary spongiosa and cortical bone of tibia (left panel). The hXBP1s S288A group of mice showed enhanced osteoclastogenesis (left panel) and number of osteoclast (right panel) compared with the WT group.
Figure 6G:
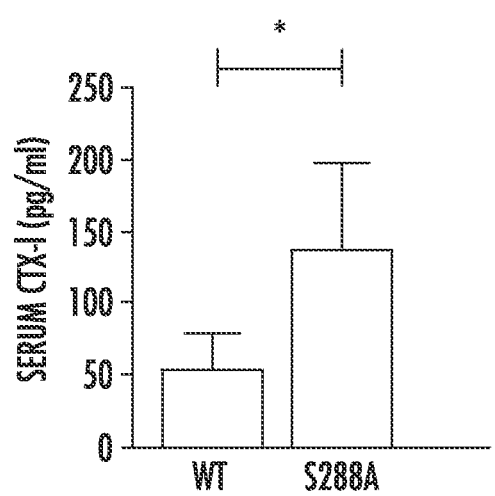
FIG. 6G: ELISA analysis of serum C-telopeptide of type I collagen (CTX-1), the type I collage breakdown product used as serum biomarker for bone turnover. The hXBP1s S288A group of mice showed higher level of serum CTX-1 than the WT group.
Figure 6H:
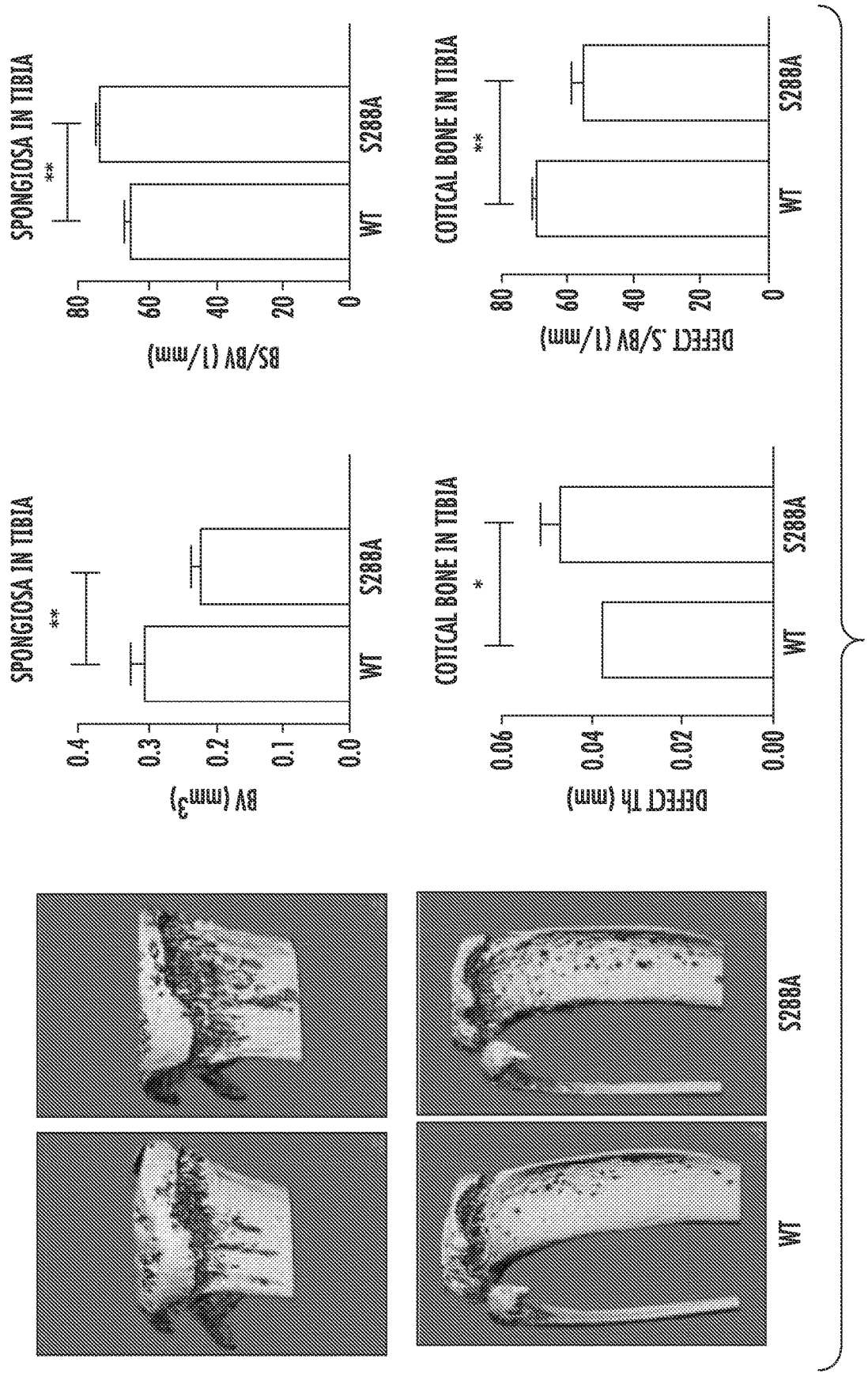
FIG. 6H: Micro-computed tomography (ΔCT) analysis of bone destruction in tibias. Compared with the WT group, the S288A group of mice displayed reduced three dimensional (3D) in tibia (left panel), cancellous bone volume (BV) in primary spongiosa, defect surface/volume ratio (Defect S/BV) in cortical bone, but increased bone surface/volume ratio (BS/BV) in primary spongiosa and defect thickness (Defect.Th) in cortical bone, indicating a more severe osteolysis (right panel). The results of FIGS. 6C, 6D and 6F were produced in independent samples, each with three replicates; the results of FIG. 6H were produced in independent samples; the results of FIGS. 6E and 6G were produced in pooled samples, each with three replicates. The scale bars from FIGS. 6C, 6D. 6E, 6F, 6G and 6H indicate SD. *P<0.05: **P<0.01 are produced by 2-tailed Student t-test.

Having observed that the S288A mutant-mediated increased the capacity of BMSCs to support OCL formation m vitro (FIG. 5F), it was next determined whether osteolysis was increased in the S288A-harboring mice in comparison with WT hXBP1s-carrying counterparts. ELISA analysis demonstrated approximately 2.3- and 1.5-fold increases in the serum levels of osteoclastogenic inflammatory cytokines IL-6 and RANKL in the S288A mice, compared with the WT hXBP1s animal group (FIG. 6E). Consistently, histological evaluation of the tibias showed that S288A mice exhibited a significantly increased number of tartrate-resistant acid phosphatase (TRAP)-positive, multinucleated osteoclasts in both the spongiosa and cortical bones, compared with the WT hXBP1s animals (FIG. 6F right panels), indicating enhanced osteoclastogenesis in S288A mice. Consequently, S288A mice displayed significantly more bone erosions in the spongiosa area and cortical bones, and an approximately 2.6-fold increase in the serum level of the C-terminal telopeptide (CTX-1) of type I collagen (COL I) (FIG. 6G), a breakdown product of COL I and a serum biomarker for bone turnover (Rosen et al., *Calcif. Tissue Int.*, 66:100-103 (2000)), compared with WT hXBP1s mice (FIG. 6F, left panels), shown by the histological examination and ELISA analysis, respectively. These latter observations indicated increased osteolysis in S288A mice compared with WT hXBP1s mice. Finally, micro-computed tomography (ΔCT) analyses on the tibias of WT control and S288A experimental groups (FIG. 6H left panels) showed that in the area of spongiosa. S288A mice displayed significantly reduced cancellous bone volume (BV), and a significant increased bone surface/volume ratio (BS/BV) (FIG. 6H, right upper panels) compared with WT mice, resulting from increased bone destruction in S288A mice. Similarly, S288A mice also exhibited a significantly increased defect thickness (Defect.Th) and a decreased defect surface/volume ratio (Defect.S/BV) in cortical bone (FIG. 6H, right lower panels), indicating a greater bone erosion and damage in S288A cortical bones. Taken together, these results demonstrated that S288-mediated phosphorylation compromises hXBP1s-mediated BMSC support of MM growth and osteoclastogenesis in vivo.

Ser288 phosphorylation of hXBP1s mediates JNKs' inhibition of the BMSC inflammatory signature and is required for the therapeutic response to JNKs-activating drugs. Activation of JNKs has therapeutic benefits in treating MM, including inducing MM apoptosis and repressing inflammatory signature of MM stromal cells (Singh et al., *Blood*, 117:5692-5700 (2011); Saha et al., *PLoS One*, 7:e30215 (2012); Xu et al., *Blood*, 92:241-251 (1998)). Having found that S288 is a direct JNKs' phosphorylation site of hXBP1s, and that dephosphorylation of hXBP1s at the S288 residue potentiates hXBP1s-mediated BMSC support of MM cell growth and osteoclast formation and thus bone destruction both in vitro and in vivo, it was hypothesized that JNKs can act through phosphorylating, and thus repressing hXBP1s to inhibit the stromal inflammatory response.

Figure 7A:
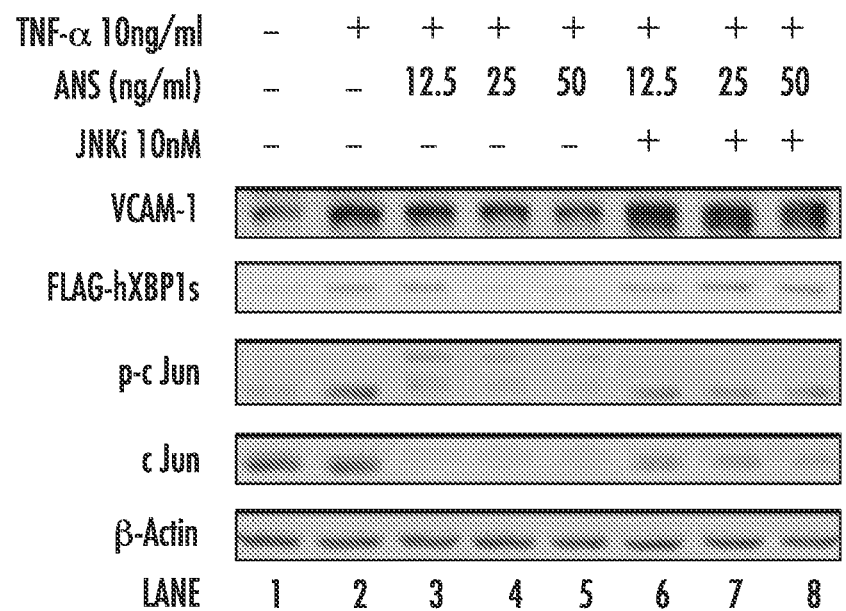
FIG. 7A: ANS dose-dependently compromised TNFα-induced up-regulation of protein expression of VCAM-1 in KM101 cells; and such inhibitory effect by ANS was blocked by JNKi. KM101 cells that stably express hXBP1s were used.
Figure 7B:
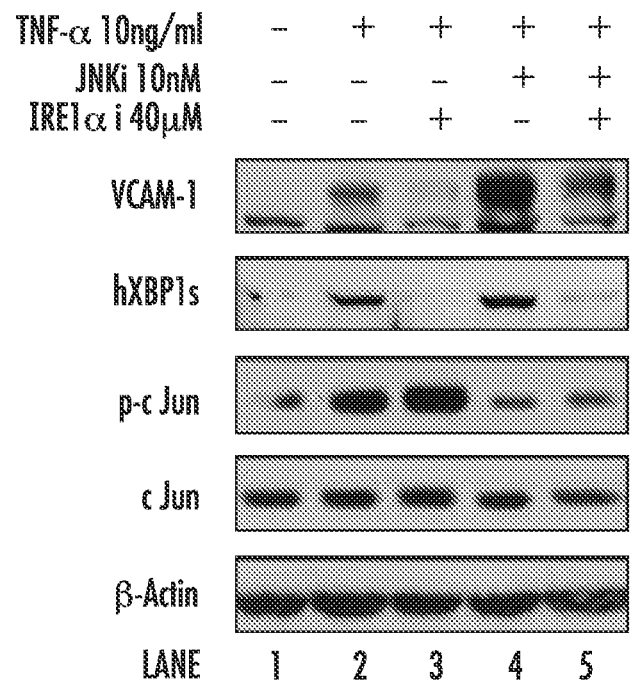
FIGS. 7B and 7C: Effects of TNFα, JNKi and IRE1α inhibitor (IRE1αi) on stromal inflammatory signature and support to MM cell adhesion. JNKi potentiated TNFα-induced VCAM-1 protein expression (FIG. 7B), adhesion of 5TGM cells to KM101 cells (FIG. 7C, upper panel), and IL-6 production in KM101 cells (FIG. 7C, lower panel). However, those inhibitory effects of JNKi were compromised in the presence of IRE1αi.
Figure 7C:
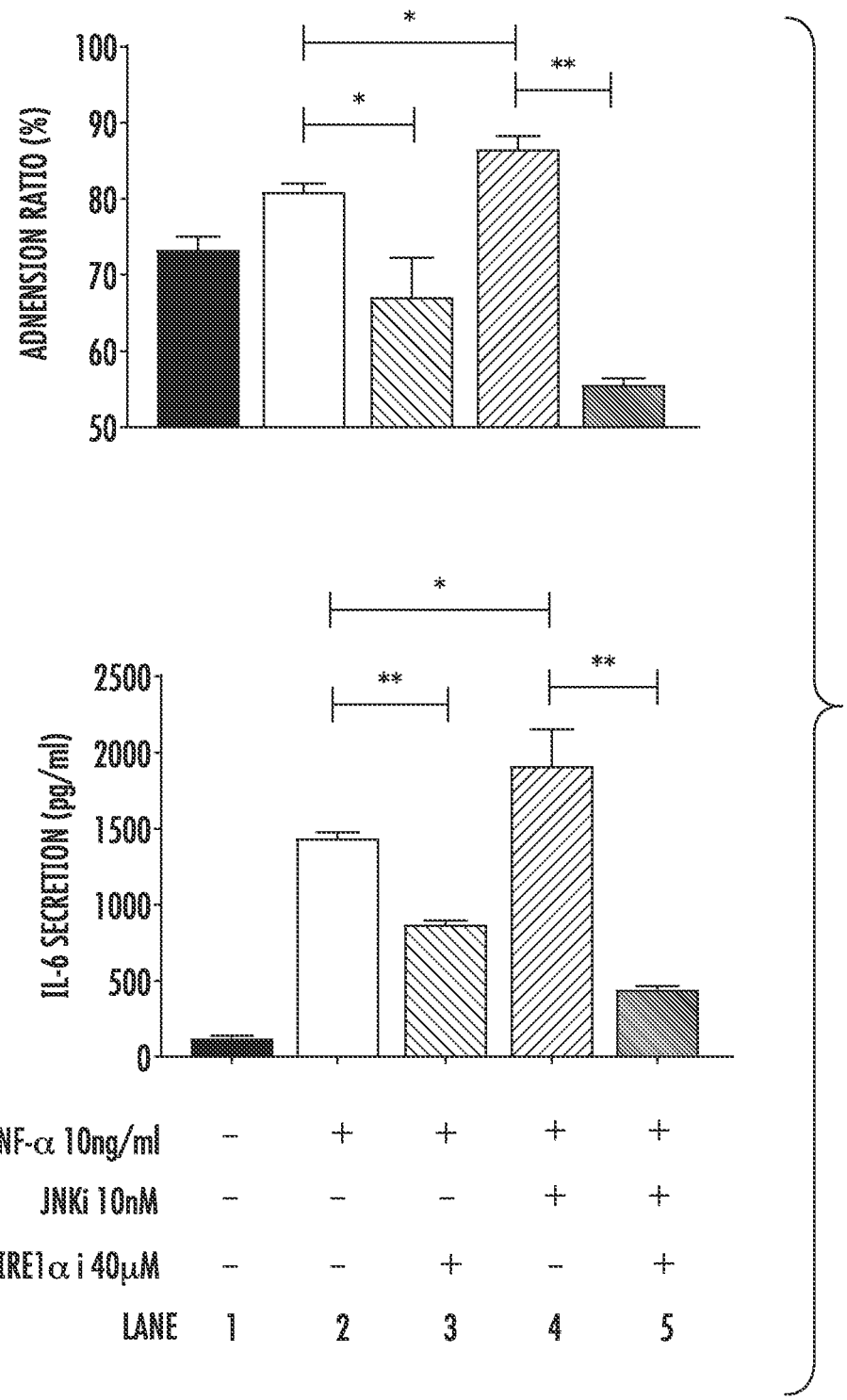

To test this hypothesis, it was confirmed that JNKs were negative regulators for the stromal inflammatory signature. TNFα, an inflammatory cytokine that is known to induce the inflammatory signature of MM BMSCs, also activates JNKs in human BMSCs KM101 cells (FIGS. 5A and 5B). It was observed that ANS-induced JNKs activation dose-dependently repressed TNFα-induced up-regulation of protein expression of VCAM-1 in KM101 cells (FIG. 7A, lanes 2-5), and this inhibition was compromised by JNKi (FIG. 7A, lanes 6-8). Conversely, JNKi potentiated TNFα-induced up-regulation of the stromal expression of VCAM-1 (FIG. 7B, lanes 1, 2, and 4), and consequently the stromal support of the adhesion of 5-TGM cells (FIG. 7C, upper panel, lanes 1, 2 and 4). Similarly, JNKi also potentiated TNFα-induced up-regulation of stromal production of IL-6 (FIG. 7C, lower panel, lanes 1, 2 and 4).

Second, it was determined whether JNKs act through repressing hXBP1s to inhibit the stromal inflammatory signature induced by TNFα. STF-083010 is a pharmacological inhibitor of the IRE1α, which specifically represses its endoribonuclease activity and thus the generation of hXBP1s (Papandreou et al., *Blood,* 117:1311-1314 (2011)). It was found that pretreatment of KM101 cells with STF-083010 repressed TNFα-induced stromal expression VCAM-1 (FIG. 7B, lanes 1, 2 and 3), stromal support of 5-TGM adhesion (FIG. 7C, upper panel, lanes 1, 2 and 3), and production of IL-6 (FIG. 7C, lower panel, lanes 1, 2 and 3), echoing the previous finding that hXBP1s is important in promoting TNFα-induced stromal inflammatory signature (Xu et al., *Blood,* 119:4205-4214 (2012)). More importantly, it was found that STF-083010 compromised JNKi's promotion of the TNFα-induced stromal induction of VCAM-1 (FIG. 7B, lanes 4-5), stromal support to 5-TGM cells' adhesion (FIG. 7C, upper panel, lanes 4-5) and stromal production of IL-6 (FIG. 7C, lower panel, lanes 4-5). The latter results demonstrated that hXBP1s is a downstream effector of JNKs that mediates JNKs' regulation of the stromal inflammatory signature.

Figure 7D:
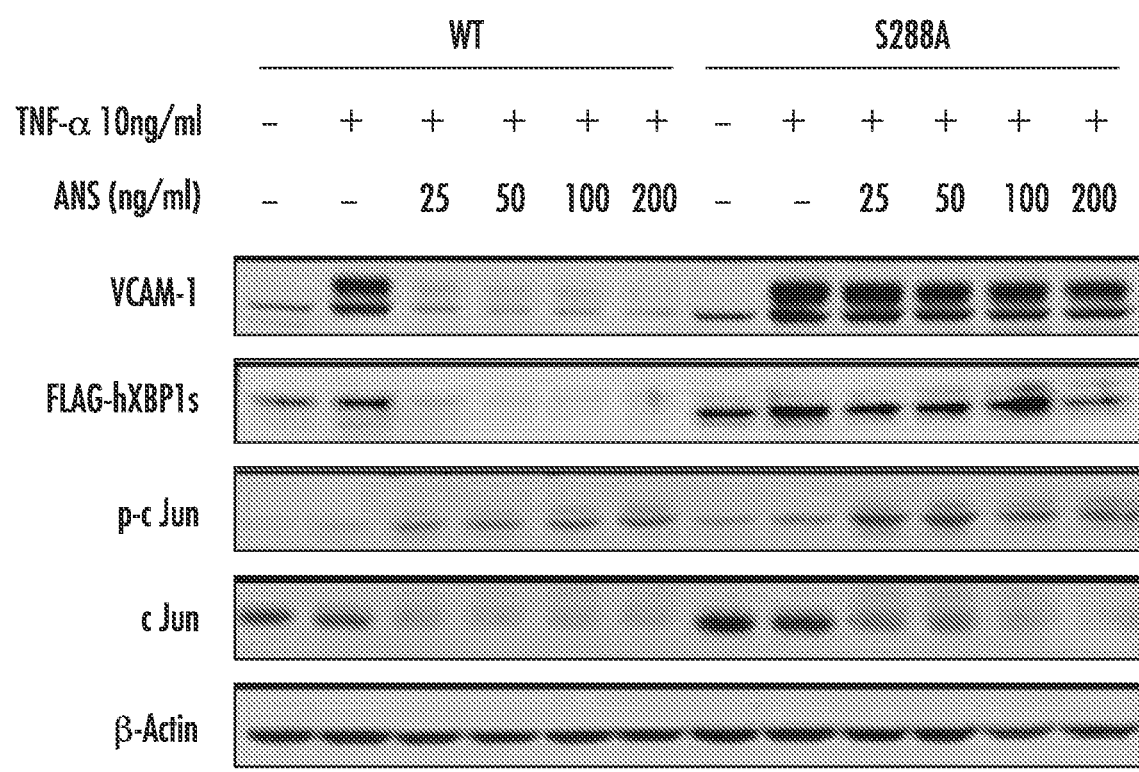
FIG. 7D: ANS dose-dependently blocked TNFα-induced VCAM-1 protein expression in hXBP1s WT-overexpressing KM101 cells, but lost its inhibitory effect in S288A mutant-overexpressing KM101 cells.

Third, it was determined whether JNKs-induced S288 phosphorylation of hXBP1s is required for JNKs' inhibitory effects on the stromal inflammatory signature. KM101 cells that stably express either the WT FLAG-hXBP1s or the S288A mutant were used for this purpose. As shown in FIG. 7D, ANS-induced activation of JNKs dose-dependently blocked TNFα-induced VCAM-1 protein expression in the WT FLAG-hXBP1s-overexpressing KM01 cells, whereas the inhibitory effect of ANS on the TNFα-induced VCAM-1 protein expression was largely abolished in the S288A mutant-overexpressing cells. These results demonstrated that JNKs largely acted through inducing S288 phosphorylation of hXBP1s to repress stromal VCAM-1 protein expression. These results demonstrate that the JNKs-mediated hXBP1s phosphorylation is a novel molecular mechanism by which JNKs repress the stromal inflammatory signature.

Figure 7E:
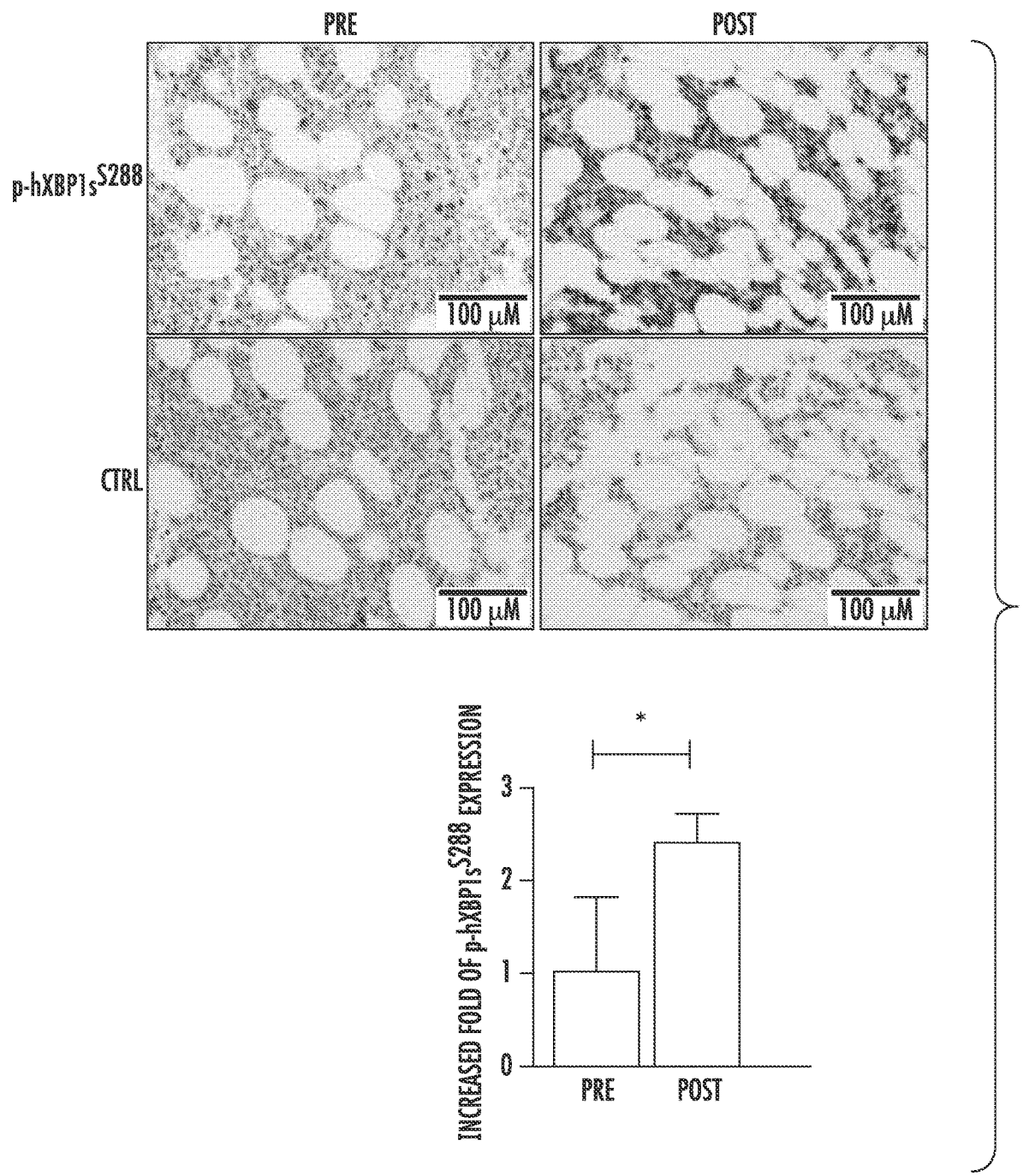
FIG. 7E: IHC analysis of p-hXBP1s$^{S288}$ expression in bone marrow tissues adjacent to MM cells of 10 MM patients before and after 3-combination or 2-combination of bortezomib, thalidomide and dexamethasone's treatment. Drugs targeting JNKs' treatment caused an increase of p-hXBP1s$^{S288}$ expression. Representative images of IHC staining were shown in the upper panel. The staining was scored, and quantification of data was presented in the lower panel.
Figure 14:
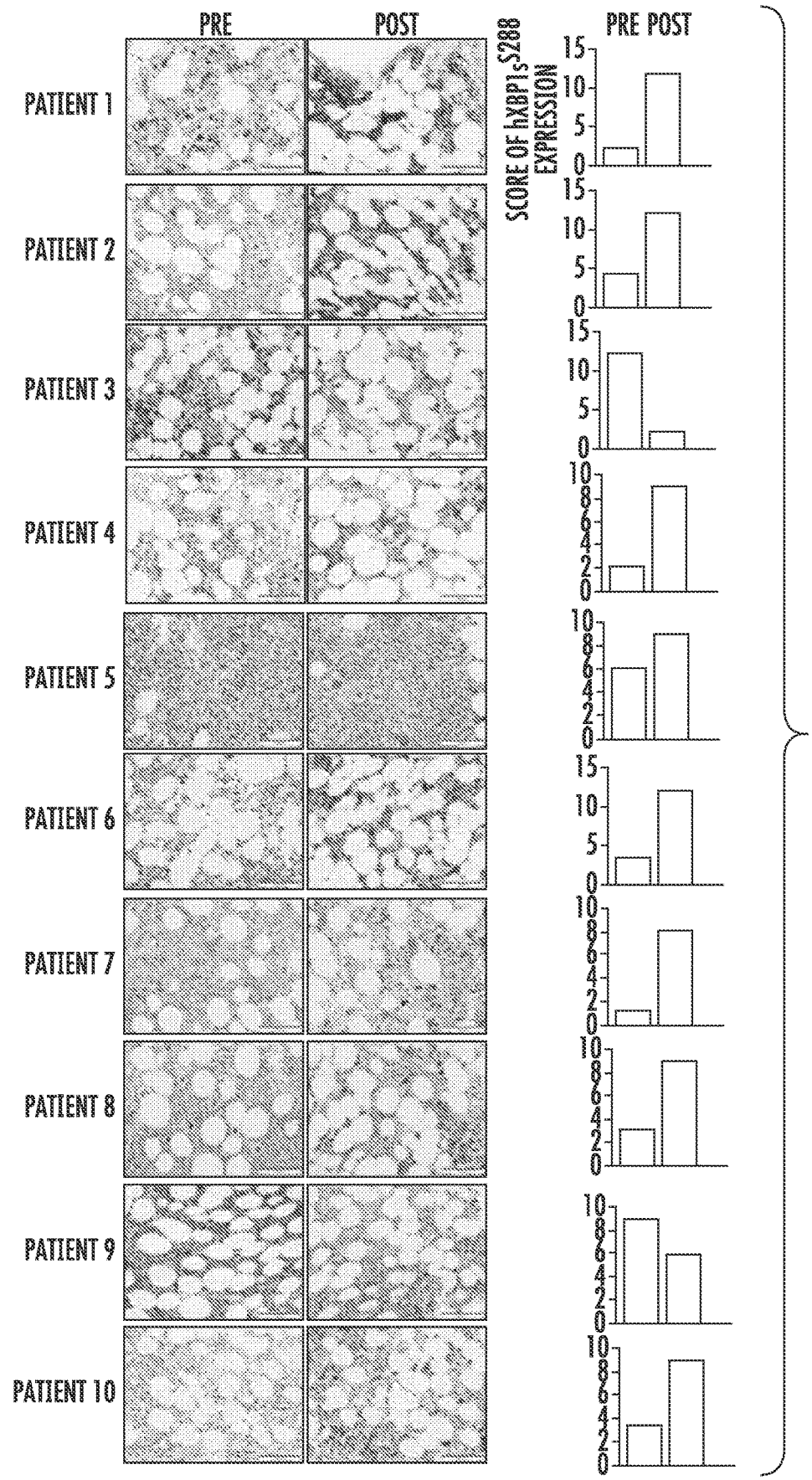
FIG. 14 shows expression of p-hXBP1s$^{S288}$ is increased in bone marrow tissues adjacent to MM from patients after treatment with a drug combination. IHC staining for p-hXBP1s$^{S288}$ expression in bone marrow tissues adjacent to MM from 10 patients before (left panel of micrographs) and after (right panel of micrographs) treatment with a combination of drugs (bortezomib, thalidomide and dexamethasone). Representative pictures are shown. Quantification and statistical analysis of the corresponding scores of IHC staining of p-hXBP1s$^{S288}$ are shown in the right panel of graphs which correspond to adjacent micrographs.

Several MM drugs, such as bortezomib, thalidomide, and dexamethasone, are potent activators of JNKs (Chauhan et al., *Oncogene,* 15:837-843 (1997); Goranov et al., *Folia. Med.,* 47:11-19 (2005); Hideshima et al., *Blood,* 101:1530-1534 (2003); Yang et al., *Cancer Sci.,* 95:176-180 (2004); Anderson et al., *Semin. Hematol.,* 42:S3-8 (2005); Pei et al., *Leukemia,* 17:2036-2045 (2003)). Besides their cytotoxic effects on MM cells, bortezomib and thalidomide repress the stromal inflammatory signature, e.g., the stromal expression of VCAM-1 (Goranov et al., *Folia. Med.,* 47:11-19 (2005); Hideshima et al., *Cancer Res.,* 61:3071-3076 (2001): Curran et al., *Drugs,* 69:859-888 (2009); Geitz et al., *Immunopharmacology,* 31:213-221 (1996)). The combination of bortezomib, thalidomide, and dexamethasone is a primary and initial therapy for both newly-diagnosed and relapsed and/or refractory MM (Rajkumar et al., *Mayo Clin. Proc.,* 91:101-119 (2016); Shen et al., *Leuk. Res.,* 35:147-151 (2011)). Thus, it was hypothesized that the JNKs/XBP1s axis constitutes a novel molecular mechanism that mediates the therapeutic effects of the JNKs-activating MM drugs on the stromal inflammatory signature. To test this hypothesis, immunohistochemistry staining for the S288 phosphorylation with antibody p-hXBP1s$^{S288}$ was used to determine and compare S288-mediated hXBP1s phosphorylation in bone marrow stromal tissues adjacent to MM from ten MM patients before and after treatment with bortezomib-containing triplet or doublet regimens (FIG. 7E: Table 4). It was found that the treatment induced the phosphorylation of hXBP1s at S288 in seven out often patients (FIG. 7E and FIG. 14). The remaining three patients displayed either no change or a moderate decrease in Ser288 phosphorylation (FIG. 14). Representative IHC staining images showing increased phosphorylation are presented in FIG. 7E. Further quantification of S288 phosphorylation changes in all ten patients demonstrated that the drug treatment significantly increased p-hXBP1s$^{S288}$ expression in the patients (Table 4; FIG. 14 and FIG. 7E, lower panel). These results demonstrated that the JNKs-p-hXBP1s signaling cascade was activated in bone marrow microenvironment in MM patients in response to the MM drugs.

Further, it was observed that that seven out of the ten patients showed a prominent increase (greater than 2-fold increase with post-treatment vs. pre-treatment) in the protein expression of p-hXBP1s$^{S288}$ in response to the drugs. Intriguingly, these patients all displayed good quality responses to the drugs, e.g., either a complete response (CR) or very good partial response (VGPR) (FIG. 14; Tables 1 and 4). By contrast, the other three patients who showed a minimal increase (less than 2-fold increase) or even a decrease in S288-mediated hXBP1s phosphorylation in response to the drugs exhibited an unfavorable partial response (PR), stable disease (SD) or even progressive disease (PD) to the treatment (FIG. 14; Tables 1 and 4). Fisher exact test analysis of the results demonstrated that up-regulation of p-hXBP1s expression in bone marrow stromal tissues adjacent to MM cells was significantly correlated (P=0.008, Table 1) with patient responses to the drugs (Table 1). These results show that S288 phosphorylation status of hXBP1s can be used as a biomarker to predict MM patient responses to JNKs-activating MM drugs.

Figure 7F:
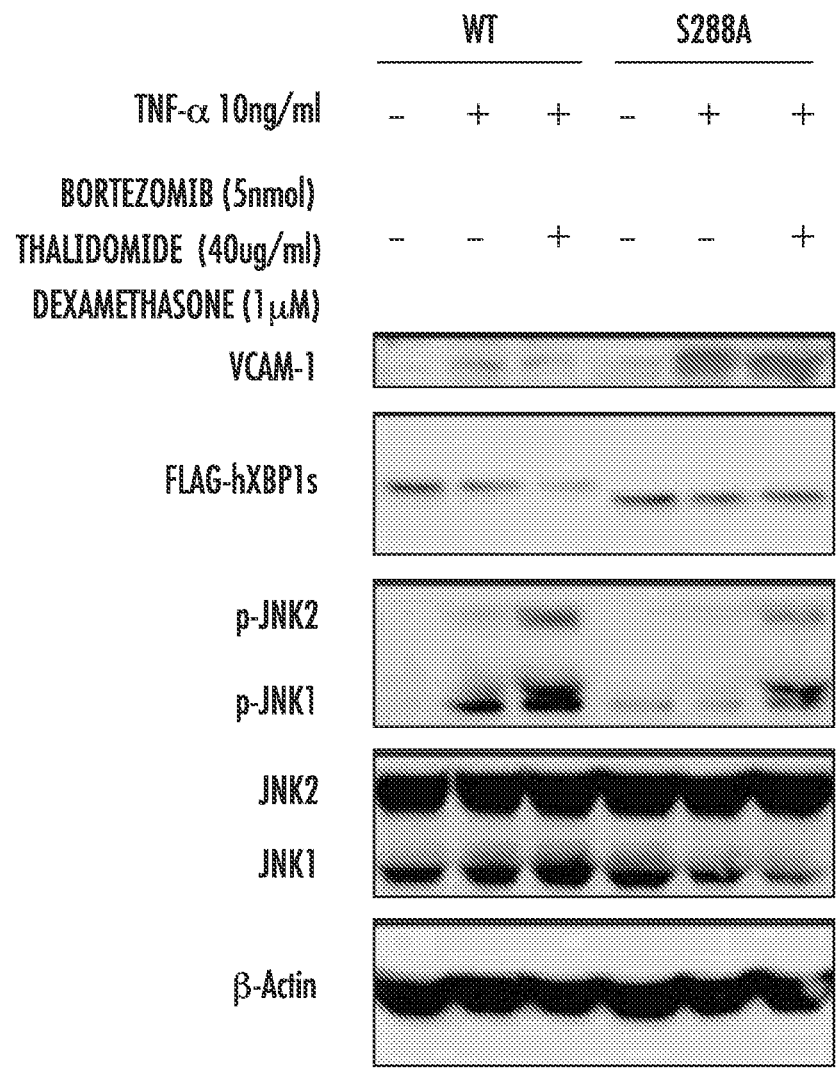
FIG. 7F: 3-drug combination of bortezomib, thalidomide and dexamethasone blocked TNFα-induced and VCAM-1 protein expression in hXBP1s WT-overexpressing KM101 cells, but lost its inhibitory effect in S288A mutant-overexpressing KM101 cells. The results were produced in three independent experiments, each with three replicates. The scale bars from FIGS. 7C and 7E indicate SD. *P<0.05; **P<0.01 in FIG. 7C were produced by 2-tailed Student t-test and * P<0.05 in FIG. 7E was produced by paired t-test.
Figure 8:
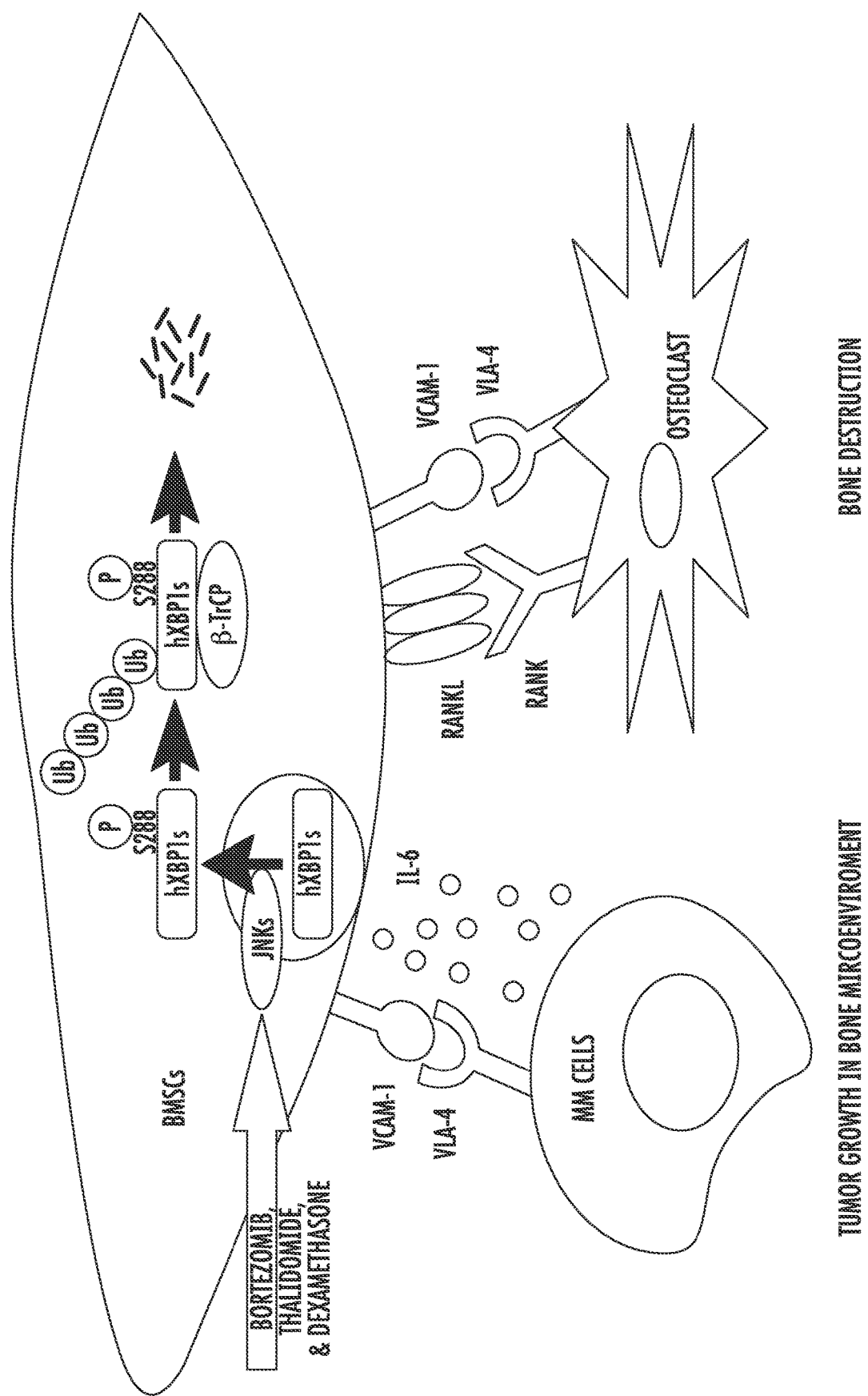
FIG. 8 is a schematic showing stromal hXBP1s protein homeostasis regulates BMSC support of MM growth and MM-induced bone destruction. The stromal hXBP1s is an essential regulator for stromal inflammatory signature and BMSC support of MM cell growth and osteoclast formation, via controlling VCAM-1, IL-6 and RANKL production, respectively. The stromal hXBP1s is subjected to JNKs-mediated phosphorylation at S288, which, in turn, promotes its ubiquitination by E3 ubiquitin ligase β-TrCP for protein degradation. MM drugs activating JNKs, e.g., bortezomib, thalidomide, and dexamethasone, induce hXBP1s phosphorylation at S288 to disrupt the stromal inflammatory signature. Phosphorylation positively correlates with the therapeutic outcome of MM patients to the drugs, demonstrating p-hXBP1s$^{S288}$ is a biomarker for MM patient responses to the bortezomib-containing drugs that activate INKs.

Next, it was determined whether the JNKs-activating MM drugs act at least partially through inducing S288 phosphorylation of hXBP1s to inhibit the stromal cell inflammatory signature. To mimic the clinic setting in vitro, the effects of the triplet regimen containing bortezomib, thalidomide and dexamethasone were tested on WT and mutant FLAG-hXBP1s-overexpressing KM101 cells. Western blot analysis demonstrated that the triplet drug regimen repressed TNFα-induced VCAM-1 protein expression in WT FLAG-hXBP1s-overexpressing KM101 cells; however, the inhibitory effects of these drugs was largely compromised in the S288A mutant-overexpressing KM101 cells (FIG. 7F). These data confirmed that the triplet drug combination can repress the stromal inflammatory signature. And, more importantly, these data indicated that S288 phosphorylation of hXBP1s is required for the therapeutic impact of this triplet drug combination on the stromal cell inflammatory signature. This finding also implies that host resistance to JNKs-mediated phosphorylation of hXBP1s, as modeled by S to A mutation at the Ser288 site, could compromise the therapeutic effectiveness of the combined drugs on the stromal inflammatory signature, thus providing a possible mechanistic explanation for the clinical observation that induction of S288 phosphorylation of hXBP1s positively correlates with favorable outcomes of the MM patients in response to the drugs.

DISCUSSION

It is disclosed herein that hXBP1s is a direct and physiological substrate of JNKs. The JNKs phosphorylate hXBP1s at the S288 residue, and the phosphorylation triggers the physical interaction of hXBP1s with β-TrCP, an SCF E3 ligase (Fuchs et al., Oncogene, 23:2028-2036 (2004)), and consequently promotes the ubiquitination and degradation of hXBP1s. These results have multiple biological, pathological, and clinical significance.

XBP1s is an evolutionarily conserved effector of ER stress signaling and maintaining XBP1s protein levels is essential for maintaining healthy organ/tissue homeostasis (Byrd et al., Cells, 1:738-753 (2012)). Since XBP1s is a short-lived protein and undergoes constant turnover (Yoshida et al., J. Cell. Biol., 172:565-575 (2006)), the proteolysis of XBP1s can serve as an essential molecular mechanism underlying the regulation of the steady-state protein levels of XBP1s in response to various pathophysiological stimuli. However, it had remained essentially unknown which E3 ligase was responsible for catalyzing the ubiquitination of hXBP1s. Here, provided for the first-time is experimental evidence that β-TrCP is the E3 ligase responsible for hXBP1s proteolysis via the 26S proteasome degradation pathway. First, it is shown that modulating $SCF^{\beta-TrCP}$ protein levels led to reversible changes in hXBP1s protein level (FIGS. 2A and 2B). Second, β-TrCP physically binds hXBP1s and induces its ubiquitination (FIG. 2E). Third, JNKs phosphorylates hXBP1s at S288 to enhance its interaction with β-TrCP and potentiate P-TrCP-mediated ubiquitination and thus proteolysis of hXBP1s (FIGS. 2F, 2G and 2H), confirming that the requirement of the β-TrCP's substrates to be phosphorylated by a kinase(s) for their recognition by O-TrCP (Cardozo et al., Nat. Rev. Mol. Cell. Biol., 5:739-751 (2004)). Fourth, it was found that hXBP1s use a PEST motif for $SCF^{\beta-TrCP}$ mediated ubiquitination of hXBP1s, which is reminiscent of the ubiquitination of the Mdm2 oncoprotein (Inuzuka et al., Cancer Cell, 18:147-159 (2010)), another substrate of $SCF^{\beta-TrCP}$ ubiquitin ligase. Taken together, these findings provide a conceptual framework to deepen the understanding of the molecular mechanisms underlying protein homeostasis of XBP1s. There are several molecular events that alter XBP1s protein stability, such as the P300/SIRT1-mediated acetylation/deacetylation (Wang et al., Biochem. J., 433:245-252 (2011)), the SUMO-conjugating independent activity of UBC9 (Uemura et al., Cell. Struct. Funct., 38:67-79 (2013)), the unspliced form of XBP1 (XBP1u)-mediated degradation mechanism (Yoshida et al., J. Cell. Biol., 172:565-575 (2006)), as well as IKKβ-mediated phosphorylation of XBP1s (Liu et al., Cell, 167:1052-1066 (2016)).

Upon ER stress, IRE1 activates JNKs and generates XBP1s mRNA to dictate opposite cell fates, for instance apoptosis or survival, respectively (Lin et al., Science, 318:944-949 (2007); Chan et al., Mol. Cell. Endocrinol., 413:189-201 (2015)). It was observed that the levels of JNK activation and hXBP1s protein expression reversely correlate with each other in response to ER stress challenge (FIG. 1A), indicating possible mutual inhibition between JNKs and XBP1s. While XBP1s reportedly contributes to the resolution of JNKs activation and JNKs-mediated cell apoptosis during ER stress via enhancing the overall cellular capacity to cope with ER stress (Pei et al., Leukemia, 17:2036-2045 (2003)), it remained unknown whether a reciprocal inhibition of XBP1s by JNKs exists in ER stress responses. As results shown herein demonstrated that INKs are a physiological upstream kinase of hXBP1s; such phosphorylation promotes its interaction with, ubiquitination and degradation by β-TrCP, it was therefore speculated that JNKs play an active role in returning the heightened hXBP is protein expression to its basal level during ER stress via JNKs-phosphorylation-induced proteolysis of hXBP1s. In this capacity, JNKs could act as an essential molecular "brake" to modulate both the intensity and duration of the XBP1s signaling branch in response to ER stress in humans.

As a first-line therapeutic choice for both newly-diagnosed and refractory MM (Rajkumar et al., Mayo Clin. Proc., 91:101-119 (2016); Shen et al., Leuk. Res., 35:147-151 (2011)), the combination of bortezomib, thalidomide and dexamethasone (and/or the derivatives) not only induces MM cell apoptosis but also inhibits the stromal inflammatory responses and support to MM growth (Chauhan D et al., Oncogene, 15:837-843 (1997); Goranov et al., Folia. Med., 47:11-19 (2005): Hideshima et al., Blood, 101:1530-1534 (2003); Yang et al., Cancer Sci., 95:176-180 (2004); Roccaro et al., Curr. Pharm. Biotechnol., 7:441-448 (2006); Anderson et al., Semin. Hematol., 42:S3-8 (2005); Hideshima et al., Cancer Res., 61:3071-3076 (2001); Geitz et al., Immunopharmacology, 31:213-221 (1996); Gupta et al., Leukemia, 15:1950-1961 (2001): Sampaio et al., J. Exp. Med., 173:699-703 (1991)). These anti-stroma effects are largely ascribed to the drug's inhibitory effects on the stromal NF-kB signaling (Goranov et al., Folia. Med., 47:11-19 (2005): Hideshima et al., Blood, 101:1530-1534 (2003): Yang et al., Cancer Sci., 95:176-180 (2004): Bai et al., Int. J. Mol. Sci., 13:4831-4838 (2012)). In the current study, a previously unknown biochemical and functional link was discovered between JNKs and hXBP1s in regulating the stromal inflammatory signature and mediating the impacts of the anti-MM drugs on stromal cells in MMBD. First, it was observed that JNKs require XBP1s to repress the stromal inflammatory signature, as IRE1 inhibitor significantly blunted JNK inhibitor's activating effects on the stromal expression of VCAM-1 and IL-6 (FIGS. 7B and 7C). Second, JNKs induce the S288 phosphorylation of hXBP1s to promote its proteolysis (FIGS. 2, 3 and 4). Third, the triplet drug combination of bortezomib, and/or thalidomide, and/or dexamethasone induced S288 phosphorylation of hXBP1s in the bone microenvironment of MM patients (FIG. 7E). Intriguingly, this phosphorylation was significantly and positively associated with good quality drug responses of the patients, e.g., a complete response (CR), or very good partial response (VGPR) (FIG. 14, Tables 1 and 4). This showed that S288 phosphorylation of hXBP1s can serve as a novel biomarker for predicting MM patients' responses to the bortezomib-containing drug regimen(s) that activate JNKs. Fourthly, both ANS (FIG. 7D) and the triplet MM drug combination (FIG. 7F) acted through inducing JNKs-phosphorylation of hXBP1s to inhibit the stromal inflammatory signature. The latter observation provides a possible molecular mechanism to explain the positive correlation between S288 phosphorylation levels and patient good quality responses to JNKs-activating drugs. Taken together, these results show that JNKs-induced XBP1s phosphorylation is a novel molecular mediator underlying the therapeutic effects of the triplet MM drug combinations on the stromal inflammatory signature. As the heightened XBP1s protein expression also occurs in MM cells (Bagratuni et al., Blood, 116:250-253 (2010); Leung-Hagesteijn et al., Cancer Cell, 24:289-304 (2013)) as well as in tumor bone marrow-resident immune cells, such as tumor-associated dendritic cells (Cubillos-Ruiz et al., Cell, 161:1527-1538 (2015)), to confer MM cell-intrinsic growth (Carrasco et al., Cancer Cell, 11:349-360 (2007); Nakamura et al., Leuk. Lymphoma, 47:531-539 (2006)), and drug sensitivity (Bagratuni et al., Blood, 116:250-253 (2010); Leung-Hagesteijn et al., Cancer Cell. 24:289-304 (2013)), and sustain cancer-extrinsic immune escape (Cubillos-Ruiz et al., Cell, 161:1527-1538 (2015)), respectively, it would be important to determine whether the JNKs-activating MM drugs also repress the MM- and/or BM immune cell-intrinsic XBP1s signaling. And if so, what the cell-specific consequences may be. Such information would provide novel insights into the molecular mechanisms underlying the therapeutic benefits of the current MM treatment and/or drug resistance of MM patients to the treatment. Finally, these results provide critical information to enhance the understanding of pathogenesis and improve the treatment of other cancers, in which constitutively activated XBP1s signaling is implicated, including but not limited to breast cancer (Chen, et al., Nature 508:103-107 (2014); Davies et al., Int. J. Cancer, 123:85-88 (2008); Fujimoto et al., Breast Cancer, 10:301-306 (2003): Hu et al., Mol. Cell. Biol., 35:379-390 (2015); Gupta et al., Oncogene. 35:5860-5871 (2016)), chronic lymphocytic leukemia (Tang et al., J. Clin. Invest., 124: 2585-2598 (2014)), and glioma (Auf et al., Proc. Natl. Acad. Sci., 107:15553-15558 (2010)).

TABLE 1

Fisher Exact test analysis of up-regulation expression of p-hXBP1s$^{S288}$ after treatment with triple or double drug combination (bortezomib, thalidomide and dexamethasone) and the therapeutic response.

| #Therapeutic response | *Notable increased p-hXBP1s$^{288}$ expression | | |
|---|---|---|---|
| | + | − | Total |
| Good | 7 | 0 | 7 |
| Fair | 0 | 1 | 1 |
| Poor | 0 | 2 | 2 |
| Total | 7 | 3 | 10 |

Statistical significance P = 0.008
*Notable increased p-hXBP1s$^{S288}$ expression: Ratio of p-hXBP1s$^{S288}$ expression (post/pre-treatment with the combination drugs) >2
Therapeutic response: Good (CR and VGRP), Fair (PR), and Poor response (SD and PD).

TABLE 2

Spearnian's rank correlation (two tailed test) analysis of expression level of p-JNK, p-hXBP1s$^{S288}$ and hXBP1s in human Bone Marrow specimens by IHC staining (36 cases).

| X vs Y | r | P |
|---|---|---|
| p-JNK vs p-hXBP1s$^{S288}$ | 0.931 | **<0.01 |
| p-JNK vs hXBP1s | −0.615 | **<0.01 |
| p-hXBP1s$^{S288}$ vs hXBP1s | −0.717 | **<0.01 |

**Correlation is significant at the 0.01 level.

TABLE 3

Semi-quantification for IHC staining of p-JNK, p-hXBP1s$^{S288}$ and hXBP1s in human bone marrow specimens (36 cases).

| Case | n-JNK | | | p-hXBP1s$^{S288}$ | | | hXBP1s | | |
|---|---|---|---|---|---|---|---|---|---|
| | Percentage | Intensity | Score | Percentage | Intensity | Score | Percentage | Intensity | Score |
| d2 | 1 | 2 | 2 | 1 | 2 | 2 | 3 | 3 | 9 |
| c3 | 1 | 1 | 1 | 1 | 1 | 1 | 4 | 2 | 8 |
| b2 | 1 | 2 | 2 | 2 | 1 | 2 | 4 | 2 | 8 |
| b4 | 1 | 2 | 2 | 1 | 1 | 1 | 4 | 7 | 8 |
| a7 | 1 | 2 | 2 | 1 | 7 | 2 | 4 | 2 | 8 |
| e2 | 1 | 2 | 2 | 1 | 2 | 2 | 1 | 2 | 6 |
| f2 | 1 | 4 | 4 | 3 | 2 | 6 | 1 | 7 | 2 |
| c9 | 4 | 2 | 8 | 4 | 2 | 8 | 1 | 1 | 1 |
| c5 | 4 | 2 | 8 | 4 | 2 | 8 | 1 | 1 | 1 |
| c4 | 3 | 1 | 3 | 3 | 1 | 3 | 1 | 1 | 1 |
| a2 | 1 | 2 | 2 | 1 | 2 | 2 | 1 | 1 | 1 |
| a6 | 1 | 2 | 2 | 1 | 2 | 2 | 1 | 1 | 1 |
| c1 | 2 | 3 | 6 | 2 | 3 | 6 | 2 | 1 | 2 |
| b10 | 4 | 1 | 4 | 4 | 1 | 4 | 1 | 1 | 1 |
| a10 | 4 | 3 | 12 | 4 | 3 | 12 | 1 | 1 | 1 |
| a4 | 4 | 2 | 8 | 4 | 2 | 8 | 1 | 1 | 1 |
| b6 | 4 | 1 | 4 | 4 | 1 | 4 | 2 | 1 | 2 |
| e10 | 4 | 1 | 4 | 4 | 1 | 4 | 1 | 2 | 2 |
| c4 | 1 | 1 | 1 | 4 | 1 | 4 | 1 | 1 | 1 |
| e7 | 1 | 3 | 3 | 2 | 2 | 4 | 1 | 1 | 1 |
| d3 | 4 | 1 | 4 | 4 | 1 | 4 | 1 | 1 | 1 |
| d8 | 3 | 2 | 6 | 3 | 2 | 6 | 1 | 1 | 1 |
| c7 | 4 | 2 | 8 | 4 | 2 | 8 | 1 | 1 | 1 |
| e5 | 4 | 2 | 8 | 4 | 2 | 8 | 1 | 1 | 1 |
| d10 | 4 | 2 | 8 | 4 | 2 | 8 | 1 | 1 | 1 |
| D4 | 1 | 3 | 3 | 1 | 3 | 3 | 1 | 4 | 4 |
| D6 | 1 | 2 | 2 | 1 | 2 | 2 | 2 | 4 | 8 |
| D1 | 1 | 2 | 2 | 2 | 1 | 2 | 2 | 2 | 4 |
| B5 | 1 | 3 | 3 | 1 | 3 | 3 | 2 | 3 | 6 |
| C3 | 2 | 2 | 4 | 2 | 2 | 4 | 1 | 2 | 2 |
| C2 | 3 | 1 | 3 | 3 | 1 | 3 | 2 | 2 | 4 |
| A3 | 3 | 2 | 6 | 2 | 2 | 4 | 1 | 2 | 2 |
| A5 | 3 | 2 | 6 | 3 | 2 | 6 | 1 | 1 | 1 |
| A1 | 3 | 2 | 6 | 3 | 2 | 6 | 1 | 1 | 1 |
| C5 | 4 | 2 | 8 | 4 | 2 | 8 | 1 | 1 | 1 |
| B3 | 2 | 2 | 4 | 3 | 1 | 3 | 1 | 2 | 2 |

TABLE 4

Semi-quantification for IHC staining of p-hXBP1s$^{S288}$ in bone marrow specimens pre/post treatment with combination drugs (bortezotnib, thalidomide and dexamethasone) and the drug responses in the MM patients (10 cases).

| Case | Treatment | Percentage | Intensity | Score | Relative fold | *Response to therapy |
|---|---|---|---|---|---|---|
| 1 | PRE | 1 | 2 | 2 | 6 | CR |
| | POST | 4 | 3 | 12 | | |
| 2 | PRE | 2 | 2 | 4 | 3 | CR |
| | POST | 4 | 3 | 17 | | |
| 3 | PRE | 4 | 3 | 12 | 0.25 | PR |
| | POST | 1 | 3 | 3 | | |
| 4 | PRE | 1 | 2 | 2 | 4 | VGPR |
| | POST | 4 | 2 | 8 | | |
| 5 | PRE | 2 | 3 | 6 | 1.5 | SD |
| | POST | 3 | 3 | 9 | | |
| 6 | PRE | 3 | 1 | 3 | 4 | CR |
| | POST | 4 | 3 | 17 | | |
| 7 | PRE | 1 | 1 | 1 | 8 | VGPR |
| | POST | 4 | 4 | 8 | | |
| 8 | PRE | 1 | 3 | 3 | 3 | CR |
| | POST | 3 | 3 | 9 | | |
| 9 | PRE | 3 | 3 | 9 | 0.666666667 | PD |
| | POST | 2 | 3 | 6 | | |
| 10 | PRE | 1 | 2 | 2 | 4.5 | CR |
| | POST | 3 | 3 | 9 | | |

*Therapeutic Response Criteria for multiple myeloma:
Complete Response (CR),
Very Good Partial Response (VGPR),
Partial Response (PR),
Stable Disease (SD) and
Progressive Disease (PD).

Methods

Biochemical Reagents.

Anti-XBP1 (M-186: 1:1000: Santa Cruz), Anti-hXBP1s (Clone 143F; 1:100 for IHC; Millipore), anti-VCAM-1 (sc-1504; 1:1000; Santa Cruz), and (sc-9073; 1:1000; Santa Cruz); anti-β-actin (A5316: 1:1000, Sigma-Aldrish); HRP-conjugated anti-Flag (A8592; 1:1000; Sigma-Aldrich); anti-Myc (MMS-150P; 1:1000; Covance); anti-HA (PRB-101P: 1:1000; Covance); anti-phospho-JNK (4668 81E11; 1:1000 for immunoblot, 1:50 for IHC; Cell Signalling), anti-JNK (9252; 1:1000: Cell Signalling), anti-phospho-c-Jun (54B3 2361; 1:1000; Cell Signalling), anti-c-Jun (60AB 9165; 1:1000; Cell Signalling); β-TrCp (D13F10 4394; 1:1000; Cell Signalling). Cy3 labelled goat anti-mouse IgG (A 10522, 1:200, Life Technology) and HRP-conjugated IgG secondary Abs (1:2000; GE Healthcare Life Sciences). Mouse IgG2a was from Stemcell Technologies Inc (Vancouver. Canada); Rabbit Negative Control IgG was from (Daka): Rabbit polyclonal anti-phospho-hXBP1s Ser288 were raised against CKIEEAPLS(p)PSEND by Covance (Denver, Pa.). JNK1 siRNA (SIHK1220 and SIHK1221, Sigma-Aldrish); JNK2 siRNA (SIHK1223 and SIHK1224, Sigma-Aldrish): MISSION® siRNA Universal Negative Control (SIC001, Sigma-Aldrish). β-TRCP1/β-TRCP2 siRNA (sense, 5'-AAGUGGAAUUUGUGGAACAUC-3' (Jin et al., *Genes Dev.,* 17:3062-3074 (2003)), synthesized by Sigma-Aldrish); Protein IgG Agarose and Amicon® Ultra 0.5 mL Centrifugal Filters were from Millipore (Rd Billerica, Mass.); TNFα and polybrene cycloheximide, anisomycin Glutathione-Agarose were from Sigma Aldrich (St. Louis, Mo.). JNK inhibitor VIII and IRE1 Inhibitor I, STF-083010 were from Calbiochem (La Jolla, Calif.), bortezomib (CAS 179324-69-7, Sigma-Aldrish), thalidomide (T144, Sigma-Aldrish), dexamethasone (D4902, Sigma-Aldrish). Fetal bovine serum, Dulbecco's Modified Eagle Medium, Opti-MEM, RPMI 1640 medium streptomycin, penicillin, Lipofectamine 2000, and Trizol were from Invitrogen (Carlsbad, Calif.). Restriction endonucleases were from New England Biolabs (Ipswich, Mass.), BCA protein assay reagent and T4 DNA ligase were from Thermo Fisher Scientific. cDNA Synthesis Kit was from Promega (Madison, Wis.), SYBR Green master mix was from ABI (Foster City, USA), and Avidin/Biotin Blocking kit, Imm PACT DAB, Normal goat/rabbit serum and Biotinylated anti Rabbit IgG(H+L) were from Vector laboratories Inc (Burlingame, Calif.).

Cell Culture.

Human kidney 297T cells, human BM stromal cell lines KM101 cells, mouse MM cell line 5-TGM1, human MM cell lines ANBL-6 and MM1.S were cultured as described. Mouse macrophage cell line RAW264.7 were cultured in DMEM supplemented with 10% FBS. Isolation of primary hBMSCs was performed as described. These studies were approved by the University of Pittsburgh institutional review board and by the VA Pittsburgh Healthcare System institutional animal care and use committee. MM cell growth assay, cell adhesion assays, OCL formation assay were performed as described (Xu et al., *Blood,* 119:4205-4214 (2012)).

Constructs, Transfection and Infection Studies.

The pCMV10-Flag-hXBPs (Ser288) and FUGW-Flag-hXBP1s (Ser288)-CMV-GFP plasmids were constructed as their WT plasmids, and the procedure was described as previously. PCDNA3 Flag MKK7B2Jnk1a1, pCDNA3 Flag MKK7B2Jnk2a2 and pCDNA3 Flag MKK7B2Jnk3a2 were purchased from Addgene (Cambridge, Mass.). Lipofectamine reagent (Invitrogen) was used for transfection according to the manufacturer's instructions, and lentiviral systems infection was performed as described.

Real-Time PCR.

Real-time PCR was performed as described previously. B-Actin was used as an internal control. The primer sequences used were (5'-3'):

hXBP1s forward: SEQ ID NO:2
hXBP1s reverse: SEQ ID NO:3
RANKL forward: SEQ ID NO:4
RANKL reverse: SEQ ID NO:5
OPG forward: SEQ ID NO:6
OPG reverse: SEQ ID NO:7
IL-6 forward: SEQ ID NO:8
IL-6 reverse: SEQ ID NO:9
B-Actin forward: SEQ ID NO: 10
B-Actin reverse: SEQ ID NO: 11

Immunoblot and Immunoprecipitation Assay.

Total cell lysates were prepared with RIPA buffer containing protease inhibitor cocktail and phosphatase inhibitor cocktails I/II (Sigma-Aldrich). After centrifugation, total cell lysates then were separated by 10% sodium dodecyl sulfate polyacrylamide gel electrophoresis and analyzed by immunoblot analysis as described previously. Signals were detected with ECL reagents (GE Healthcare Life Sciences). Semi-quantification of data was performed using Image J. For immunoprecipitation assay, Cells were washed with ice-cold PBS and lysed with lysis buffer (50 mM Tris-HCl, pH 7.5; 150 mM NaCl, 0.1% (wt/vol) Nondiet P40, 1 mM Ethylenediaminetetraacetic acid (EDTA); 100 mM PMSF; protease inhibitor cocktail and phosphatase inhibitor cocktails I/II (Sigma-Aldrich). After overnight incubation with Anti-HA-agarose beads (Roche) or anti-hXBP1s antibody at 4° C. on a rotator, following by addition of Protein G Agarose to the reaction containing anti-hXBP1s antibody for 2 h at 4° C. Immunoprecipitates were washed three times with cold lysis buffer and boiled for 5 min in 2× Laemmli buffer for elution of immunoprecipitated HA-hXBP1s or Flag-hXBP1s complex. Samples were resolved in SDS-PAGE (Bio-Rad) and immunoblotted with corresponding antibody.

ELISA.

To determine hIL-6 secretion by BMSCs, supernatants from cell cultures were collected and analyzed with hIL-6 ELISA read-set go kits (eBioscience) according to the manufacturer's instructions, the mice's serum concentration of IgG2b, RANKL, IL-6 and CTX-I were measured with their respectively ELISA kit (Quidel, Roche, Roche and MyBioSource).

Immunochemistry.

The 293T cells grown on glass chamber slides (BD Biosciences) were transfected with pEGFP-C1-hXBP1s and MYC-f-TrCP. Forty-eight hours after transfection, cells were rinsed briefly in PBS and then were fixed with 4% paraformaldehyde in PBS for 10 min and rendered permeable by further treatment with 0.2% Triton X-100 for 5 min. Mouse anti-MYC antibody (1:100) was diluted in PBSB (1% BSA in PBS) and incubated with cells for 1 h in room temperature. After three washes with PBSB, cells were incubated with Cy3 labelled goat anti-mouse IgG diluted in PBSB for 1 h. Cells were washed, mounted with ProLong Gold Antifade Mountant with DAPI (Life Technology), viewed, and photographed under a FluoView 1000 confocal microscope (Olympus).

In Vitro Kinase Assay.

Transform pGEX-6P-1-hXBP1s WT and mutant plasmids and express these GST fusion proteins in BL21 *E. coli* (Invitrogen), and then the GST fusion proteins were purified by Glutathione-Agarose and concentrated with Amicon Ultra-0.5 centrifugal filter (Millipore). In vitro kinase assay: 90 ng active recombinant human JNK1α1, JNK2α2 and JNK3 (Millipore) were respectively incubated with indicated 200 ng GST-hXBP1s WT and mutant proteins in the presence of γ-$^{32}$P-ATP in kinase action buffer (5 mM Tris/HCl pH7.4, 1.07 mM MgCl$_2$, 0.78 mM MnCl$_2$, and 0.1 mM DDT). Kinase reaction products were resolved by SDS-PAGE, and phosphorylation was detected by autoradiography. Total hXBP1s and JNK protein levels were detected by immunoblotting.

Osteoclast Formation and TRAP Staining.

For in vitro TRAP staining, flush bone marrow from fresh mouse leg, and culture the cells for overnight in MEM with 10% FBS, then absorb supernatant for centrifugation 1200 rpm for 5 min. Keep the bone marrow monocytes (BMM) cells in the precipitate and re-suspend BMM with conditional medium (MEM with 10% FBS+MCSF 10 pg/ml. RANKL 160 pg/ml). Then plate 20×10$^4$ BMM cells in 96-wells plates with KM101 cells. Change medium every 3 days. Observe OLC and do TRAP staining with Acid Phosphatase, Leukocyte (TRAP) Kit (387A-1KT; Sigma-Aldrich) on the 6$^{th}$ day.

For bone marrow osteoclast staining, fix mouse whole legs in 4% Paraformaldehyde at 4° C. for 3 days. Decalcification in 10% EDTA solution (pH7.0) at 4° C. for 3 months (change fresh 10% EDTA solution every 3 day). Wash in PBS for 2 hours, and then dehydrated and paraffin embedded tissue was cut at 5 μm thick sections for TRAP staining with Acid Phosphatase, Leukocyte (TRAP) Kit (387A-1KT: Sigma-Aldrich).

Immunohistochemical Staining.

Tissue array of human bone marrow (BM) tissues were purchased from US Biomax and MM patients bone marrow sections were provided by Dr. Nicola Giuliani. Tissues were dewaxed with xylene and rehydrated through gradient ethanol into water. For antigen retrieval, sections were heated in citrate buffer (pH6.0) for 8 min at 95° C. in a water bath. Endogenous peroxidase activity was quenched with 0.3% H$_2$O$_2$ for 5 min at room temperature. After TBS/TBS+Triton 0.25% washes, nonspecific antibody binding was blocked by 10% normal goat/Rabbit non-immune serum at 37° for 60 min. After blotting off the blocking serum. Sections were further blocked endogenous biotin or biotin-binding activity with kit, and then incubated with primary antibody against p-JNK (1:50), hXBP1s (1:200) or p-hXBP1s$^{S288}$ (1:5000) at 4° C. overnight. After TBS/TBS+Triton 0.25% washes, sections were incubated with biotinylated secondary antibody at 1:250 for 30 min. After incubating with Vectastain ABC reagent (Vector Laboratories, Inc., Burlingame, Calif.) for 45 min, the sections were developed with DAB (3,3-Diaminobenzidine). Sections were counterstained with hematoxylin, followed by coverslip mounting. Negative controls were obtained by Rabbit/Mouse IgG antibody.

To evaluate the expression of p-JNK, hXBP1s and p-hXBP1s$^{S288}$, the percentage of positive BM cells were determined semi-quantitatively by assessing the entire BM section. Each sample was assigned to one of the following categories: 0 (0-4%). 1 (5-24%), 2 (25-49%), 3 (50-74%), or 4 (75-100%). The intensity of immunostaining was determined as 0 (negative), 1+ (weak), 2+ (moderate), or 3+ (strong). A final immunoreactive score between 0 and 12 was calculated by multiplying the percentage of positive cells with the staining intensity score. All slides were blind evaluated for immunostaining without any knowledge of the clinical outcome or other clinical or pathological data.

Nano-Liquid Chromatography Tandem Mass Spectrometry Analysis (nLC-MS/MS). The HEK293T were transfected with HA-tagged hXBP1s expressing constructs and co-transfection with mixture of MKK7-JNK1, MKK7-JNK2 and MKK7-JNK3 constructs. Immunoprecipitation assay was performed as described previously. Samples were resolved in SDS-PAGE (Bio-Rad) and stained with Simpleblue Safe Stain (Invitrogen).

Protein from Coomassie-stained gel bands was digested with trypsin similarly as described (Fang et al., Nat. Commun., 5:5513 (2014); Shevchenko et al., Nat. Protoc., 1:2856-2860 (2006)). In brief, gel bands containing HA tagged-hXBP1s were destained with 50% acetonitrile (ACN)/25 mM ammonium bicarbonate until no visible staining. Gel pieces were dehydrated with 100% ACN, reduced with 10 mM dithiothreitol (DT) at 56° C. for 1 hour, followed by alkylation with 55 mM iodoacetamide (IAA) at room temperature for 45 min in the dark. Gel pieces were then again dehydrated with 100% ACN to remove excess DTT and IAA, and rehydrated with 20 ng/l trypsin in 25 mM ammonium bicarbonate and digested overnight at 37° C. The resultant tryptic peptides were extracted with 70% ACN/5% formic acid, vacuum dried and re-constituted in 18 μl 0.1% formic acid.

The resultant complex mixture of tryptic peptides was analyzed using nLC-MS/MS as previously described (Fang et al., Nat. Commun., 5:5513 (2014): Miedel et al., Methods, 68:536-541 (2014)). In brief, samples were loaded with a nanoAcquity autosampler (Waters, Waltham Mass.) onto a capillary sample trap column, separated using a reversed phase gradient on a 0.075×100 mm PicoChip™C18 column (New Objective, Inc. Woburn Mass.), and ionized via electrospray ionization. Mass analysis was performed on a hybrid LTQ Orbitrap Velos mass spectrometer (Thermo Fisher Scientific, Waltham Mass.). Data dependent acquisition was used to acquire a high-resolution full scan mass spectrum followed by 13 low resolution tandem mass spectra, with dynamic exclusion enabled to minimize redundant selection of precursor ions.

Peptide sequence identification was achieved by submitting the resulting MS/MS spectra to the MASCOT data base search engine. The MS/MS spectra were matched to amino acid sequences contained in the UniProt human proteome database (December 2013 release) from the European Bioinformatics Institute (www.ebi.ac.uk/integr8). The following amino modifications were used: static modification of cysteine (carboxyamidomethylation, +57.05 Da), variable modification of methionine (oxidation, +15.99 Da) and variable modification of serine/threonine/tyrosine (phosphorylation, +79.97 Da). The mass tolerance was set at 20 ppm for the precursor ions and 0.8 Da for the fragment ions. Peptide identifications were further filtered using PeptideProphet™ and ProteinProphet® algorithms with a protein threshold cutoff of 99% and peptide threshold cutoff of 95% implemented in Scaffold™ (Proteome Software, Portland, Oreg., USA).

In Vivo MM Cell Growth.

NIH III female mice (4 weeks old) were intratibially injected with cell mixture of KM101 transfected with Flag-hXBP1s WT or Flag-hXBP1s S288A (5×10$^4$) and 5TGM1-GFP-TK cells (1×105) (vol. 20 μl). All animal studies were performed under the Guide for the Care and Use of Laboratory Animals under the auspices of Division of Laboratory Animal Resources (DLAR) under a protocol approved by the University of Pittsburgh Institutional Animal Care and Use Committee (IACUC). Tumor growth, metastases, and bone destruction was assessed 4 weeks post-tumor injection using PET/CT imaging. At the end of the experiment (week 4) tumors and both tibias were dissected for further analysis. Serum was collected for analysis of tumor and bone destruction markers.

PET/CT Imaging.

NIH III nude mice bearing MM tumors (n=4) were injected intravenously (lateral tail vein) with $^{68}$Ga-DOTA-PEG4-LLP2A (7.4 MBq, 370 ng). Imaging was performed at 2 h post-injection. Mice were anaesthetized with 2% isoflurane and small animal PET/CT was performed. Static images were collected for 15 min using a small animal Inveon PET/CT scanner (Siemens Medical Solution, Knoxville, Tenn.). Tangential and radial full width at half-maximum are 1.5 mm at the center of field of view (FOV) and 1.8 mm at the edge of FOV. PET and CT images were co-registered with Inveon Research Workstation (IRW) software (Siemens Medical Solutions, Knoxville, Tenn.). PET images were reconstructed with the Ordered-Subsets Expectation Maximization 3D/maximum a-posteriori probability (OSEM-3D) algorithm, and the analysis of images was done using IRW software. Regions of interest (ROI) were drawn based on the CT and the associated PET activities were calculated. Standard uptake values (SUVs) were calculated based on the following formula: SUV=([Bq/mL]×[animal weight (g)]/[injected dose (Bq)]).

Microct Assay.

Tibiae from nude mice bearing MM tumors were imaged by a microCT 35 (Scanco, Bassersdorf, Switzerland) microCT scanner with a six-micron voxel size and a 55 Kvp beam energy (400 millisecond exposure time, 1 frame captured per view) in holders provided by the manufacturer and a 70% ethanol environment. 3D volumes were automatically reconstructed from the lateral projections using the Scanco software. Processing of the 3D tibiae volumes was performed using the Scanco 3D morphometry and densitometry software. The volumes were first reoriented to a standardized orientation to best align the scanned bone segments along the scan z axis, after which cortical, secondary and primary spongiosa regions of interest were user-defined as follows: for the cortical bone the periosteal and endosteal boundary was traced from 1.55 mm from the end of the growth plate and extending 4.5 mm towards the mid diaphysis. For the secondary spongiosa, the region of interest was the endosteal envelope (including cancellous bone inside the growth plate) extending to 1 mm from the end of the growth plate towards the mid diaphysis and the whole area of the ephiphysis proximal to the growth plate containing cancellous bone. Cortical and cancellous bone morphometry of the tibiae volumes was performed in a 3D mode, with calculated parameters for the secondary and primary spongiosa bone volume fraction (BVF-accounting for porosity and bone lost to the tumor progress) and relative surface (BS/BV), The equivalent parameters for cortical bone were defect thickness (Defect.Th) and relative surface (Defect.S/BV).

Statistical Analysis.

Each experiment was performed at least three times and results are presented as means SD. Statistical significance was determined by test statistical analysis was performed using SPSS statistical software (SPSS Inc., Chicago, Ill.). Spearman correlation coefficients were used to evaluate the correlation between expression levels of different proteins. Descriptive statistics were (means±S.D) used to summarize the data distribution. T tests were used to compare the means between different experimental groups. Paired t tests were used to compare the pre- and post-treatment expression level of p-hXBP1s S288p. All tests are 2-sided and p<0.05 was considered statistically significant.

Study Approval.

The current studies utilized de-identified, existing clinical bone marrow tissue sections for the IHC staining for mapping out the protein expression of the phosphorylated hXBP1s. Patient samples were obtained after informed consent, according to the Declaration of Helsinki, for a separate and unrelated project on patients with monoclonal gammopathies, approved by the Institutional Ethical Review Board of University of Parma (Italy), and the Institutional Review Board of the University of Pittsburgh (USA). All animal-related protocols were approved by the University of Pittsburgh's Institutional Animal Care and Use Committee.

Example 2: Sequences

```
A hXBP1s Amino Acid Sequence (Ser288 is highlighted in shading).
                                                              SEQ ID NO: 1
  1 mvvvaaapnp adgtpkvlll sgqpasaaga pagqalplmv paqrgaspea asgglpqark 61 rqrlthlspe ekalrrklkn rvaaqtardr kkarmseleq qvvdleeenq klllenqllr 121 ekthglvven qelrqrlgmd alvaeeeaea kgnevrpvag saesaagagp vvtppehlpm 181 dsggidssds esdillgild nldpvmffkc pspepaslee lpevypegps slpaslslsv 241 gtssakleai nelirfdhiy tkplvleips etesqanvvv kieeaplsps endhpefivs 301 vkeepveddl vpelgisnll ssshcpkpss clldaysdcg yggslspfsd mssllgvnhs 361 wedtfanelf pqlisv
```

```
                                                              SEQ ID NO: 2
AAA CAG AGT AGC AGC TCA GAC TGC
```

```
                                                              SEQ ID NO: 3
TCC TTC TGG GTA GAC CTC TGG GAG
```

```
                                                              SEQ ID NO: 4
ACA TAT CGT TGG ATC ACA GCA CAT
```

```
                                                              SEQ ID NO: 5
CAA AAG GCT GAG CTT CAA GCT T
```

-continued

GGA ACC CCA GAG CGA AAT ACA

SEQ ID NO: 6

CCT GAA GAA TGC CTC CTC ACA

SEQ ID NO: 7

GGT ACA TCC TCG ACG GCA TCT

SEQ ID NO: 8

GTG CCT CTT TGC TGC TTT CAC

SEQ ID NO: 9

GGC GGC ACC ACC ATG TAC CCT

SEQ ID NO: 10

AGG GGC CGG ACT CGT CAT ACT

SEQ ID NO: 11

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is intended that the appended claims cover all such equivalent variations as fall within the true spirit and scope of the invention.

I claim:

1. A method for predicting responsiveness of a subject with a cancer to an activator of JNK kinase activity, the method comprising:
    a) obtaining a sample from the subject with cancer;
    b) determining in the sample the level of phosphorylation of XBP1s at position Ser288 of the amino acid sequence; wherein the level of phosphorylation is determined using an antibody that specifically binds to XBP1s phosphorylated at position Ser288 of the amino acid sequence; and
    c) comparing the level of a phosphorylation of XBP1s at position Ser288 of the amino acid sequence in the sample to a control sample, wherein an increase in the level of a phosphorylation of XBP1s at position Ser288 of the amino acid sequence as compared to the control sample indicates the responsiveness of a subject with cancer to an activator of JNK kinase activity.

2. The method of claim 1, wherein the cancer is multiple myeloma.

3. The method of claim 1, wherein the control sample is from a healthy subject or a subject without cancer.

4. The method of claim 1, further comprising administering to the subject an activator of JNK kinase activity.

5. The method of claim 4, wherein the activator of JNK kinase activity comprises one or more of bortezomib, dexamethasone, or thalidomide.

6. A method of monitoring the effectiveness of an activator of JNK kinase activity, the method comprising:
    a) administering to a subject a compound that is an activator of JNK kinase activity;
    b) obtaining a sample from the subject;
    c) determining in the sample the level of phosphorylation of XBP1s at position Ser288 of the amino acid sequence; wherein the level of a phosphorylation is determined using an antibody that specifically binds to XBP1s phosphorylated at position 288 of the amino acid sequence; and
    d) comparing the level of a phosphorylation of XBP1s at position 288 of the amino acid sequence in the sample to a control sample, wherein an increase in the level of a phosphorylation of XBP1s at position 288 of the amino acid sequence as compared to the control sample indicates the effectiveness of the activator of JNK kinase activity.

7. The method of claim 6, wherein the subject is suffering from a cancer.

8. The method of claim 7, wherein the cancer is multiple myeloma.

9. The method of claim 6, wherein the control sample is from the subject prior to administration of the activator of JNK kinase activity.

10. The method of claim 6, further comprising administering one or more additional doses of the activator of JNK kinase activity to the subject if the method indicates the activator of JNK kinase activity is effective.

11. The method of claim 6, wherein the activator of JNK kinase activity comprises one or more of bortezomib, dexamethasone, or thalidomide.

12. A method for treating a subject with a cancer, the method comprising:
    a) obtaining a sample from the subject with a cancer;
    b) determining in the sample the level of phosphorylation of XBP1s at position Ser288 of the amino acid sequence; wherein the level of phosphorylation is determined using an antibody that specifically binds to XBP1s phosphorylated at position Ser288 of the amino acid sequence;
    c) comparing the level of a phosphorylation of XBP1s at position Ser288 of the amino acid sequence in the sample to a control sample; and
    d) administering to the subject a therapeutically effective amount of an activator of JNK kinase activity if an increase in the level of a phosphorylation of XBP1s at position Ser288 of the amino acid sequence is detected.

13. The method of claim 12, wherein the cancer is multiple myeloma.

14. The method of claim 12, wherein the control sample is from a healthy subject or a subject without cancer.

15. The method of claim 12, wherein the activator of JNK kinase activity comprises one or more of bortezomib, dexamethasone, or thalidomide.

16. The method of claim 12, further comprising administering to the subject an additional therapeutic agent.

17. A method for screening for a modulator of phosphorylation of XBP1s at position Ser288 of the amino acid sequence, the method comprising:
    a) contacting a cell with at least one candidate therapeutic agent;
    b) determining in the cell the level of phosphorylation of XBP1s at position Ser288 of the amino acid sequence; wherein the level of phosphorylation is determined using an antibody that specifically binds to XBP1s phosphorylated at position Ser288 of the amino acid sequence;
    c) comparing the level of a phosphorylation of XBP1s at position Ser288 of the amino acid sequence in the cell to a control cell; and
    d) wherein an increase or decrease in the level of a phosphorylation of XBP1s at position Ser288 of the amino acid sequence as compared to a control cell indicates the at least one candidate therapeutic agent is a modulator of phosphorylation of XBP1s at position Ser288 of the amino acid sequence.

18. The method of claim 17, wherein the control cell is a cell that has not been treated with the candidate therapeutic agent.

19. The method of claim 17, wherein the method is performed in a 96-well microtiter plate or 384-well microtiter plate.

* * * * *

SEQUENCE LISTING

```
<160> NUMBER OF SEQ ID NOS: 11

<210> SEQ ID NO 1
<211> LENGTH: 376
<212> TYPE: PRT
<213> ORGANISM: Artificial Sequence
<220> FEATURE:
<223> OTHER INFORMATION: Synthetic construct

<400> SEQUENCE: 1

Met Val Val Val Ala Ala Ala Pro Asn Pro Ala Asp Gly Thr Pro Lys
 1               5                  10                  15

Val Leu Leu Leu Ser Gly Gln Pro Ala Ser Ala Ala Gly Ala Pro Ala
             20                  25                  30

Gly Gln Ala Leu Pro Leu Met Val Pro Ala Gln Arg Gly Ala Ser Pro
         35                  40                  45

Glu Ala Ala Ser Gly Gly Leu Pro Gln Ala Arg Lys Arg Gln Arg Leu
     50                  55                  60

Thr His Leu Ser Pro Glu Glu Lys Ala Leu Arg Arg Lys Leu Lys Asn
 65                  70                  75                  80

Arg Val Ala Ala Gln Thr Ala Arg Asp Arg Lys Lys Ala Arg Met Ser
                 85                  90                  95

Glu Leu Glu Gln Gln Val Val Asp Leu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
    130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Asp Ser Glu Ser
            180                 185                 190
```

```
Asp Ile Leu Leu Gly Ile Leu Asp Asn Leu Asp Pro Val Met Phe Phe
            195                 200                 205

Lys Cys Pro Ser Pro Glu Pro Ala Ser Leu Glu Glu Leu Pro Glu Val
210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
            260                 265                 270

Glu Ser Gln Ala Asn Val Val Val Lys Ile Glu Glu Ala Pro Leu Ser
        275                 280                 285

Pro Ser Glu Asn Asp His Pro Glu Phe Ile Val Ser Val Lys Glu Glu
    290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
        355                 360                 365

Leu Phe Pro Gln Leu Ile Ser Val
    370                 375

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
aaacagagta gcagctcaga ctgc                                          24

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
tccttctggg tagacctctg ggag                                          24

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
acatatcgtt ggatcacagc acat                                          24

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct
```

```
<400> SEQUENCE: 5
caaaaggctg agcttcaagc tt                                          22

<210> SEQ ID NO 6
<211> LENGTH: 21
<212> TYPE: DNA
<213> ORGANISM: Artificial Sequence
<220> FEATURE:
<223> OTHER INFORMATION: Synthetic construct

<400> SEQUENCE: 6
ggaaccccag agcgaaatac a                                           21

<210> SEQ ID NO 7
<211> LENGTH: 21
<212> TYPE: DNA
<213> ORGANISM: Artificial Sequence
<220> FEATURE:
<223> OTHER INFORMATION: Synthetic construct

<400> SEQUENCE: 7
cctgaagaat gcctcctcac a                                           21

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
ggtacatcct cgacggcatc t                                           21

<210> SEQ ID NO 9
<211> LENGTH: 21
<212> TYPE: DNA
<213> ORGANISM: Artificial Sequence
<220> FEATURE:
<223> OTHER INFORMATION: Synthetic construct

<400> SEQUENCE: 9
gtgcctcttt gctgctttca c                                           21

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
ggcggcacca ccatgtaccc t                                           21

<210> SEQ ID NO 11
<211> LENGTH: 21
<212> TYPE: DNA
<213> ORGANISM: Artificial Sequence
<220> FEATURE:
<223> OTHER INFORMATION: Synthetic construct

<400> SEQUENCE: 11
aggggccgga ctcgtcatac t                                           21
```